US012679851B2

(12) United States Patent
Chen

(10) Patent No.: US 12,679,851 B2
(45) Date of Patent: Jul. 14, 2026

(54) METHYL-SUBSTITUTED BENZOBISOXAZOLE COMPOUND AND USE THEREOF

(71) Applicant: TONGHUA DONGBAO PHARMACEUTICAL CO., LTD., Jilin (CH)

(72) Inventor: Shuhui Chen, Shanghai (CN)

(73) Assignee: TONGHUA DONGBAO PHARMACEUTICAL CO., LTD., Jilin (CN)

( * ) Notice: Subject to any disclaimer, the term of this patent is extended or adjusted under 35 U.S.C. 154(b) by 711 days.

(21) Appl. No.: 18/009,481

(22) PCT Filed: Jun. 10, 2021

(86) PCT No.: PCT/CN2021/099432

§ 371 (c)(1),
(2) Date: Dec. 9, 2022

(87) PCT Pub. No.: WO2021/249492

PCT Pub. Date: Dec. 16, 2021

(65) Prior Publication Data

US 2023/0234968 A1 Jul. 27, 2023

(30) Foreign Application Priority Data

Jun. 10, 2020 (CN) ......................... 202010524591.8
Aug. 27, 2020 (CN) ......................... 202010878829.7
May 25, 2021 (CN) ......................... 202110573980.4

(51) Int. Cl.
*C07D 513/04* (2006.01)
*A61P 3/10* (2006.01)
*C07D 519/00* (2006.01)

(52) U.S. Cl.
CPC .............. *C07D 513/04* (2013.01); *A61P 3/10* (2018.01); *C07D 519/00* (2013.01)

(58) Field of Classification Search
CPC ... C07D 513/04; C07D 519/00; C07D 495/04
See application file for complete search history.

(56) References Cited

U.S. PATENT DOCUMENTS

2019/0225604 A1 7/2019 Yoshino et al.
2022/0204510 A1 6/2022 He et al.

FOREIGN PATENT DOCUMENTS

CN 110325530 A 10/2019
CN 111247151 A 6/2020
WO WO-2018109607 A1 6/2018
WO WO-2019239319 A1 12/2019
WO WO-2019239371 A1 12/2019
WO WO-2022135572 A1 * 5/2022 ............. C07D 95/04
WO WO-2022228490 A1 * 11/2022 ........... A61K 31/496

OTHER PUBLICATIONS

Patani et al., (Chem. Rev., 1996, 96, 3147-3176).*
May 28, 2024 The extended European search report issued in European Patent Application No. 21822762.7.
Jan. 19, 2024 Chinese Office Action issued in Chinese Patent Application No. 202180041386.9.
Sep. 9, 2023 Chinese Office Action issued in Chinese Patent Application No. 202180041386.9.
Sep. 8, 2023 Chinese Search Report issued in Chinese Patent Application No. 202180041386.9.
Sep. 8, 2021 International Search Report issued in International Patent Application No. PCT/CN2021/099432.
Sep. 8, 2021 Written Opinion of the International Searching Authority issued in International Patent Application No. PCT/CN2021/099432.

* cited by examiner

*Primary Examiner* — Susanna Moore
(74) *Attorney, Agent, or Firm* — Harness, Dickey & Pierce, P.L.C.

(57) ABSTRACT

Provided are a new methyl-substituted benzobisoxazole compound and the use thereof in the preparation of drugs for treating related diseases. Specifically disclosed is a compound represented by formula (P) or a pharmaceutically acceptable salt thereof.

(P)

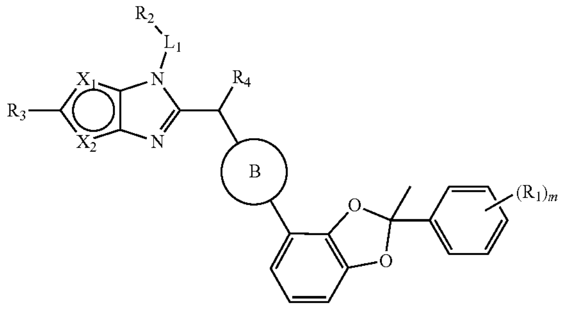

7 Claims, 3 Drawing Sheets

METHYL-SUBSTITUTED BENZOBISOXAZOLE COMPOUND AND USE THEREOF

CROSS-REFERENCE TO RELATED APPLICATIONS

The present application is a U.S. National Phase Application under 35 U.S.C. 371 of International Application No. PCT/CN2021/099432, filed on Jun. 10, 2021, which claims the benefit of Chinese Patent Application No. 202010524591.8, filed on Jun. 10, 2020, Chinese Patent Application No. 202010878829.7, filed on Aug. 27, 2020, and Chinese Patent Application No. 202110573980.4, filed on May 25, 2021. The entire disclosures of the above applications are incorporated herein by reference.

TECHNICAL FIELD

The present disclosure relates to a class of methyl-substituted benzodioxazole compounds and a use thereof in the manufacture of a medicament for the treatment of related diseases, and specifically relates to a compound represented by formula (P) or a pharmaceutically acceptable salt thereof.

BACKGROUND

The latest data released in the 9th edition of the IDF Global Diabetes Overview show that 463 million adults (20-79 years old) are currently living with diabetes. Three out of every four people with diabetes (352 million) are of working age (i.e., 20-64 years old). That number is expected to rise to 478 million by 2030 and to 700 million by 2045. Furthermore, 1.1 million children and adolescents under the age of 20 have type I diabetes. The 2017 guideline for the prevention and treatment of type II diabetes in China mentioned that the prevalence rate of type II diabetes in the national survey in 2013 was 10.4%, which was higher in males than in females (11.1% vs. 96%), and the undiagnosed diabetes patients accounted for 63% of the total.

Glucagon-like peptide-1 (GLP-1) receptor belongs to the G-protein-coupled glucagon receptor family, which is a peptide hormone secreted by intestinal L cells, widely distributed in the mucosa of the pancreas, stomach and small intestine, as well as the heart, lung and central nervous system. GLP-1 specifically binds to its receptor to activate the cyclic adenosine monophosphate (cAMP) and mitogen-activated protein kinase (MAPK) pathways in the cytoplasm membrane. After the activation of cAMP, cAMP synergizes with glucose stimulate insulin synthesis and secretion, and inhibit glucagon secretion. At the same time, activation of the protein kinase, phosphatidylinositol-3-kinase (PI3K) and MAPK pathway can slow down the apoptosis of β cells and promote the differentiation and proliferation of islet β cells. Thus, GLP-1 can produce a variety of physiological functions, such as: inhibiting the apoptosis of islet β cells, improving the function of islet β cells; inhibiting the secretion of glucagon; delaying the emptying of gastric contents, suppressing appetite and food intake, etc. Since Exenatide was approved for marketing in 2005, GLP-1 receptor agonists have mild adverse reactions (mainly gastrointestinal symptoms (such as nausea, vomiting, etc.)), and have clinical benefits such as cardiovascular benefits, renal benefits, improvement of heart failure, weight reduction, and improvement of liver fibrosis/liver function indicators in addition to glucose decline, and have gradually become the priority recommended drug for diabetes guidelines at home and abroad. However, the GLP-1 receptor agonists currently on the market are all polypeptide macromolecule drugs, which need to be administered by injection, so the patient compliance is poor. The technical conditions of polypeptide macromolecule drugs also lead to expensive drugs and high storage requirements.

The development of small molecule GLP-1 receptor agonists with oral activity can facilitate the use of patients, reduce medical burden, and improve compliance. Small molecule GLP-1 receptor agonists are expected to become safer and more effective new hypoglycemic drugs to meet the therapeutic needs of diabetes.

CONTENT OF THE PRESENT INVENTION

The present disclosure provides a compound represented by formula (P) or a pharmaceutically acceptable salt thereof,

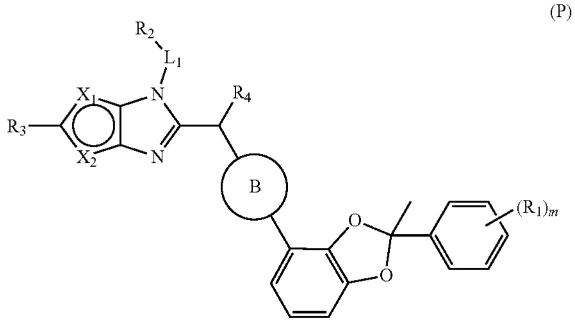

(P)

wherein,
ring B is selected from

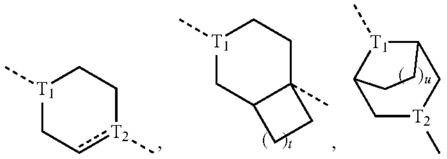

and

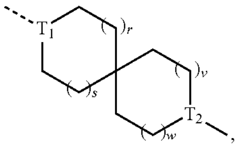

, and the

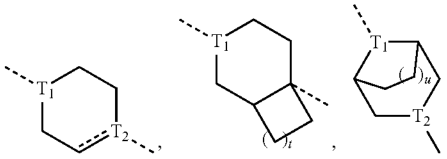

and

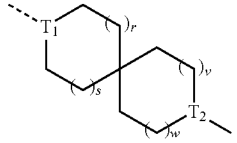

are optionally substituted by 1, 2 or 3 $R_5$;

═ is selected from a single bond and a double bond, and when $T_2$ is selected from N, ═ is selected from the single bond;

$T_1$ and $T_2$ are selected from N and CH;

$X_1$ and $X_2$ are each independently selected from CH, N, O and S, and the CH is optionally substituted by one F, Cl, Br and $CH_3$;

$L_1$ is selected from a single bond and —$C_{1-3}$ alkyl-;

$R_1$ is selected from F, Cl, Br, I, OH, $NH_2$ and CN;

u, v, w, r, s and t are each independently 0 or 1;

m is selected from 0, 1, 2, 3, 4 and 5;

$R_2$ is selected from

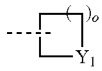

and

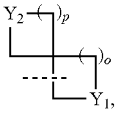

, and the

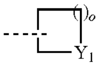

and

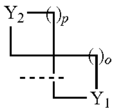

are optionally substituted by 1, 2 or 3 $R_a$;

$Y_1$ and $Y_2$ are each independently selected from CH, $CH_2$, N, NH and O;

o and p are each independently selected from 0, 1, 2 and 3;

$R_3$ is selected from —C(═O)—NH—$R_b$, —C(═O)—$R_b$, —C(═O)—NH—S(═O)$_2$—$R_b$, —S(═O)$_2$—NH—$R_b$, —S(═O)$_2$—$R_b$, —P(═O)($R_b$)$_2$, $C_{1-3}$ alkyl, tetrazolyl, isoxazolyl,

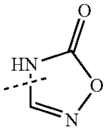

and

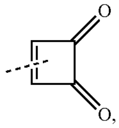

, and the $C_{1-3}$ alkyl, tetrazolyl, isoxazolyl,

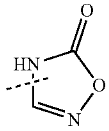

and

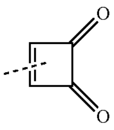

are optionally substituted by 1, 2 or 3 $R_b$;

$R_5$ is selected from F, Cl, Br, I and $C_{1-3}$ alkyl;

$R_4$ is selected from H, F, Cl, Br, I and $CH_3$;

$R_a$ is selected from F, Cl, Br and I;

$R_b$ is selected from OH, CN, $C_{1-3}$ alkyl, $C_{1-3}$ alkoxy, $C_{1-3}$ alkylamino and oxazolyl, and the $C_{1-3}$ alkyl, $C_{1-3}$ alkoxy and oxazolyl are optionally substituted by 1, 2 or 3 R;

R is selected from F, Cl and Br.

In some embodiments of the present disclosure, the $R_2$ is selected from

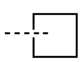

and

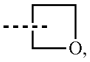

, and the

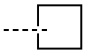

and

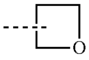

are optionally substituted by 1, 2 or 3 $R_a$, and the other variables are as defined in the present disclosure.

In some embodiments of the present disclosure, the $R_2$ is selected from

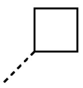

and

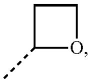

, and the other variables are as defined in the present disclosure.

In some embodiments of the present disclosure, the $L_1$ is selected from the single bond and —$CH_2$—, and the other variables are as defined in the present disclosure.

In some embodiments of the present disclosure, the m is selected from 0, 1 and 2, and the other variables are as defined in the present disclosure.

In some embodiments of the present disclosure, the $R_b$ is selected from OH, CN, $CH_3$, $CF_3$ and $OCH_3$, and the other variables are as defined in the present disclosure.

In some embodiments of the present disclosure, the $R_3$ is selected from —COOH, —C(═O)—NH—CN, —C(═O)—NH—OH, —C(═O)—NH—$OCH_3$, —C(═O)—$CF_3$, —S(═O)$_2$—NH—$CH_3$ and —S(═O)$_2$—OH, and the other variables are as defined in the present disclosure.

In some embodiments of the present disclosure, the ring B is selected from

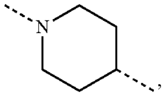

,

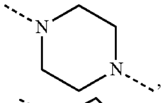

,

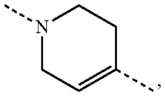

,

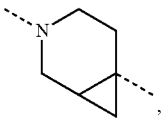

,

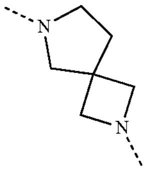

and

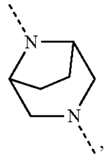

, and the other variables are as defined in the present disclosure.

In some embodiments of the present disclosure, the structural moiety

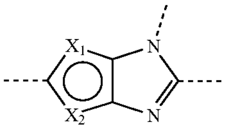

is selected from

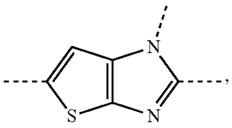, 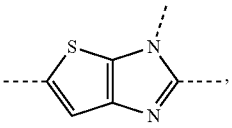,

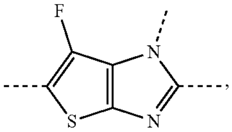, 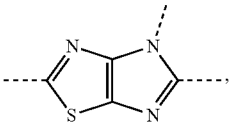 and

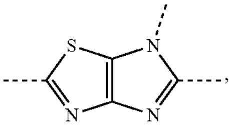, and the other variables are as defined in the present disclosure.

The present disclosure provides a compound represented by formula (III) or a pharmaceutically acceptable salt thereof, (III)

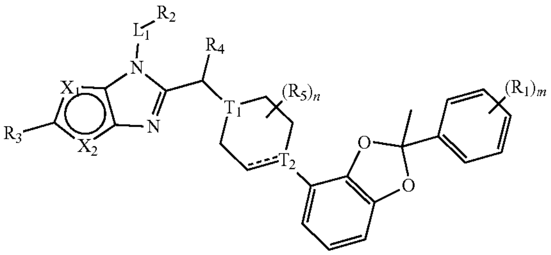

wherein,

═ is selected from a single bond and a double bond, and when $T_2$ is selected from N, ═ is selected from the single bond;

$T_1$ and $T_2$ are selected from N and CH;

$X_1$ and $X_2$ are each independently selected from CH, N, O and S, and the CH is optionally substituted by one F, Cl, Br and $CH_3$;

$L_1$ is selected from a single bond and —$C_{1-3}$ alkyl-;

$R_1$ is selected from F, Cl, Br, I, OH, $NH_2$ and CN;

m is selected from 0, 1, 2, 3, 4 and 5;

$R_2$ is selected from

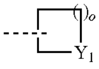 and

-continued

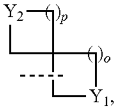, and the

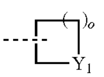 and 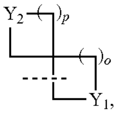, are optionally substituted by 1, 2 or 3 $R_a$;

$Y_1$ and $Y_2$ are each independently selected from CH, $CH_2$, N, NH and O;

o and p are each independently selected from 0, 1, 2 and 3;

$R_3$ is selected from —C(═O)—NH—$R_b$, —C(═O)—$R_b$, —C(═O)—NH—S(═O)$_2$—$R_b$, —S(═O)$_2$—NH—$R_b$, —S(═O)$_2$—$R_b$, —P(═O)($R_b$)$_2$, $C_{1-3}$ alkyl, tetrazolyl, isoxazolyl

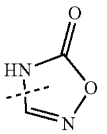 and

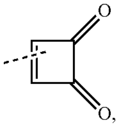, and the $C_{1-3}$ alkyl, tetrazolyl, isoxazolyl,

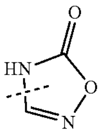 and

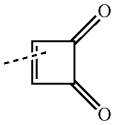

are optionally substituted by 1, 2 or 3 $R_b$;

$R_5$ is selected from F, Cl, Br, I and $C_{1-3}$ alkyl;

n is selected from 0, 1 and 2;

alternatively, two adjacent $R_5$ together form a $C_{3-5}$ cycloalkyl;

$R_4$ is selected from H, F, Cl, Br, I and $CH_3$;

$R_a$ is selected from F, Cl, Br and I;

$R_b$ is selected from OH, CN, $C_{1-3}$ alkyl, $C_{1-3}$ alkoxy, $C_{1-3}$ alkylamino and oxazolyl, and the $C_{1-3}$ alkyl, $C_{1-3}$ alkoxy and oxazolyl are optionally substituted by 1, 2 or 3 R;

R is selected from F, Cl and Br.

The present disclosure provides a compound represented by formula (I) or a pharmaceutically acceptable salt thereof, (I)

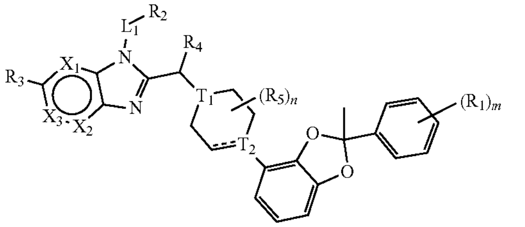

wherein,

=== is selected from a single bond and a double bond, and when $T_2$ is selected from N, === is selected from the single bond;

$T_1$ and $T_2$ are selected from N and CH;

$X_1$ and $X_2$ are each independently selected from CH, N, O and S;

$X_3$ is selected from a single bond, CH and N;

$L_1$ is selected from a single bond and —$C_{1-3}$ alkyl-;

$R_1$ is selected from F, Cl, Br, I, OH, $NH_2$ and CN;

m is selected from 0, 1, 2, 3, 4 and 5;

$R_2$ is selected from

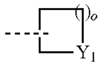 and

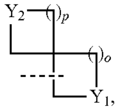, and the

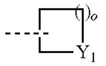 and

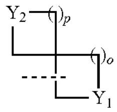

are optionally substituted by 1, 2 or 3 $R_a$;

$Y_1$ and $Y_2$ are each independently selected from CH, $CH_2$, N, NH and O;

o and p are each independently selected from 0, 1, 2, and 3;

$R_3$ is selected from —C(=O)—NH—$R_b$, —C(=O)—$R_b$, —C(=O)—NH—S(=O)$_2$—$R_b$, —S(=O)$_2$—NH—$R_b$, —S(=O)$_2$—$R_b$, —P(=O)($R_b$)$_2$, $C_{1-3}$ alkyl, tetrazolyl, isoxazolyl,

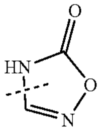 and

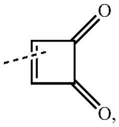, and the $C_{1-3}$ alkyl, tetrazolyl, isoxazolyl,

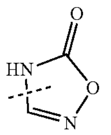 and

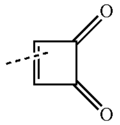

are optionally substituted by 1, 2 or 3 $R_b$;

$R_5$ is selected from F, Cl, Br, I and $C_{1-3}$ alkyl;

n is selected from 0, 1 and 2;

alternatively, two adjacent $R_5$ together form a $C_{3-5}$ cycloalkyl;

$R_4$ is selected from H, F, Cl, Br, I and $CH_3$;

$R_a$ is selected from F, Cl, Br and I;

$R_b$ is selected from OH, CN, $C_{1-3}$ alkyl, $C_{1-3}$ alkoxy, $C_{1-3}$ alkylamino and oxazolyl, and the $C_{1-3}$ alkyl, $C_{1-3}$ alkoxy and oxazolyl are optionally substituted by 1, 2 or 3 R;

R is selected from F, Cl and Br;

when $X_3$, $X_4$ and $X_5$ are simultaneously selected from CH or at least one of $X_3$, $X_4$ and $X_5$ is selected from N, then === is selected from the double bond or two adjacent $R_5$ together === form the $C_{3-5}$ cycloalkyl.

The present disclosure provides a compound represented by formula (I) or a pharmaceutically acceptable salt thereof, (I)

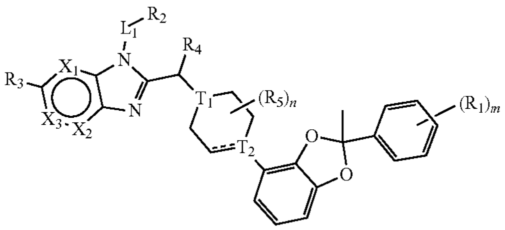

wherein,

=== is selected from a single bond and a double bond, and when $T_2$ is selected from N, === is selected from the single bond;

$T_1$ and $T_2$ are selected from N and CH;

$X_1$ and $X_2$ are each independently selected from CH, N, O and S;

$X_3$ is selected from a single bond, CH and N;

$L_1$ is selected from a single bond and —$C_{1-3}$ alkyl-;

$R_1$ is selected from F, Cl, Br, I, OH, $NH_2$ and CN;

m is selected from 0, 1, 2, 3, 4 and 5;

$R_2$ is selected from

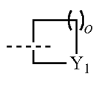 and 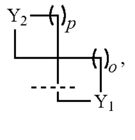, and the

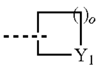 and

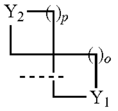

are optionally substituted by 1, 2 or 3 $R_a$;

$Y_1$ and $Y_2$ are each independently selected from CH, $CH_2$, N, NH and O;

o and p are each independently selected from 0, 1, 2 and 3;

$R_3$ is selected from —C(═O)—NH—$R_b$, —C(═O)—$R_b$, —S(═O)$_2$—NH—$R_b$ and —S(═O)$_2$—$R_b$;

$R_5$ is selected from F, Cl, Br, I and $C_{1-3}$ alkyl;

n is selected from 0, 1 and 2;

alternatively, two adjacent $R_5$ together form a $C_{3-5}$ cycloalkyl;

$R_4$ is selected from H, F, Cl, Br, I and $CH_3$;

$R_a$ is selected from F, Cl, Br and I;

$R_b$ is selected from OH, CN, $C_{1-3}$ alkyl and $C_{1-3}$ alkoxy, and the $C_{1-3}$ alkyl and $C_{1-3}$ alkoxy are optionally substituted by 1, 2 or 3 R;

R is selected from F, Cl and Br;

when $X_3$, $X_4$ and $X_5$ are simultaneously selected from CH or at least one of $X_3$, $X_4$ and $X_5$ is selected from N, then ═══ is selected from the double bond or two adjacent $R_5$ together form the $C_{3-5}$ cycloalkyl.

In some embodiments of the present disclosure, the $R_2$ is selected from and

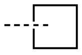 and

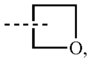

and the

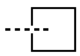 and 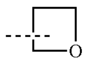

are optionally substituted by 1, 2 or 3 $R_a$, and the other variables are as defined in the present disclosure.

In some embodiments of the present disclosure, the $R_2$ is selected from

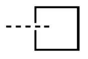 ,

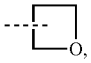

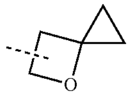 and

-continued

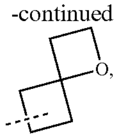

and the

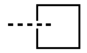 ,

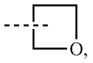

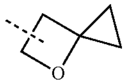 and

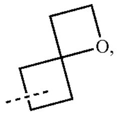

are optionally substituted by 1, 2 or 3 $R_a$, and the other variables are as defined in the present disclosure.

In some embodiments of the present disclosure, the $R_2$ is selected from

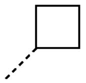 and 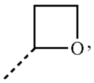

and the other variables are as defined in the present disclosure.

In some embodiments of the present disclosure, the $R_2$ is selected from

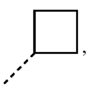 , 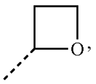 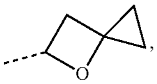 , 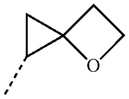 and

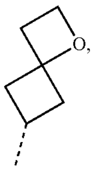

and the other variables are as defined in the present disclosure.

In some embodiments of the present disclosure, the $L_1$ is selected from the single bond and —$CH_2$—, and the other variables are as defined in the present disclosure.

In some embodiments of the present disclosure, the m is selected from 0, 1 and 2, and the other variables are as defined in the present disclosure.

In some embodiments of the present disclosure, the $R_b$ is selected from OH, CN, $CH_3$, $CF_3$ and $OCH_3$, and the other variables are as defined in the present disclosure.

In some embodiments of the present disclosure, the $R_3$ is selected from —COOH, —C(═O)—NH—CN, —C(═O)—NH—OH, —C(═O)—NH—$OCH_3$, —C(═O)—$CF_3$, —S(═O)$_2$—NH—$CH_3$ and —S(═O)$_2$—OH, and the other variables are as defined in the present disclosure.

In some embodiments of the present disclosure, the structural moiety

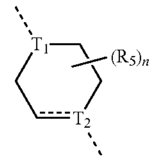

is selected from

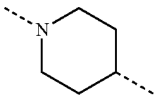, 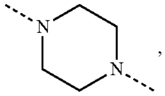, 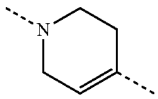, and

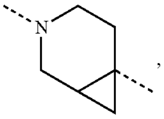, and the other variables are as defined in the present disclosure.

In some embodiments of the present disclosure, the structural moiety

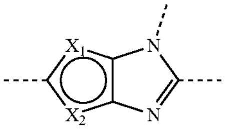

is selected from

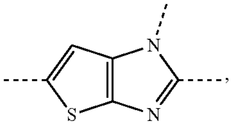, 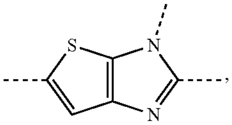, 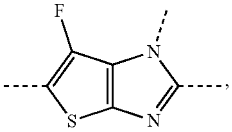, 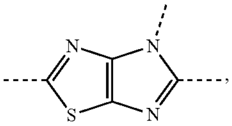, and

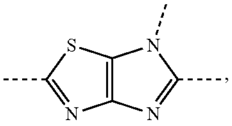, and the other variables are as defined in the present disclosure.

In some embodiments of the present disclosure, the structural moiety

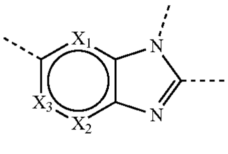

is selected from

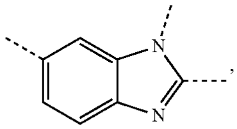, 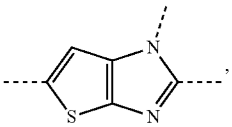, 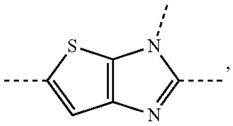, 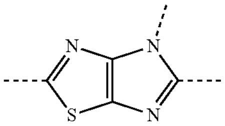 and

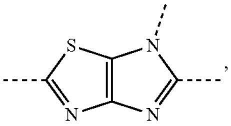, and the other variables are as defined in the present disclosure.

There are still some embodiments of the present disclosure which are obtained by any combination of the above variables.

In some embodiments of the present disclosure, the compound or the pharmaceutically acceptable salt thereof is selected from:

(P-1)

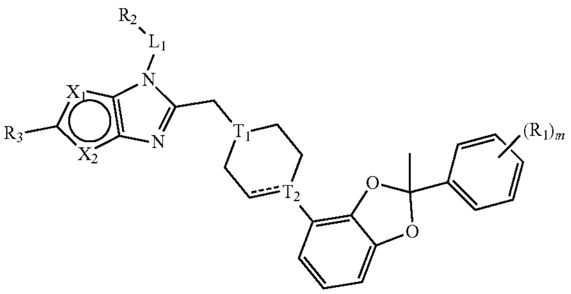

(P-2)

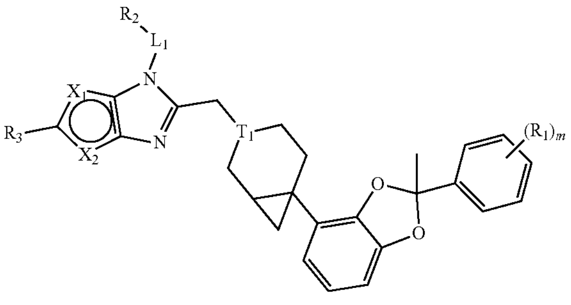

(P-3)

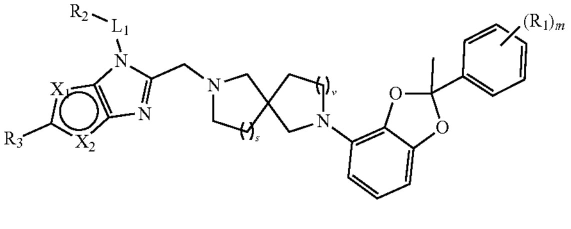

-continued (P-4)

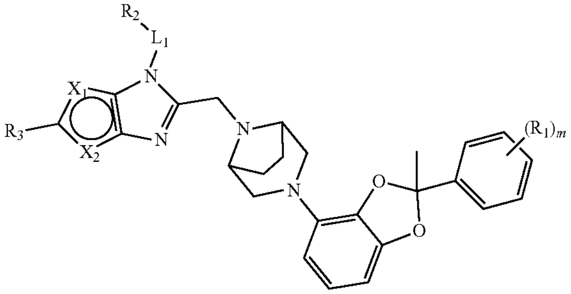

wherein,

=== is selected from a single bond and a double bond, and when $T_2$ is selected from N, === is selected from the single bond;

s and v are each independently 0 or 1;

$R_1$, $R_2$, $R_3$, $L_1$, $T_1$, $T_2$, $X_1$, $X_2$ and m are as defined in the present disclosure.

In some embodiments of the present disclosure, the compound or the pharmaceutically acceptable salt thereof is selected from:

(I-3)

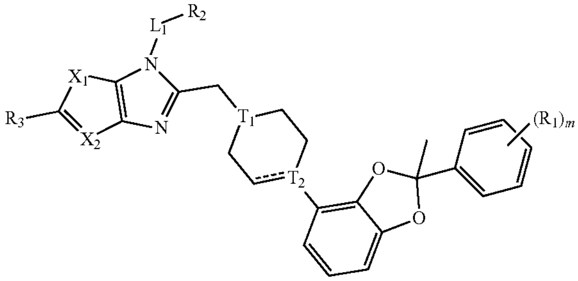

(I-4)

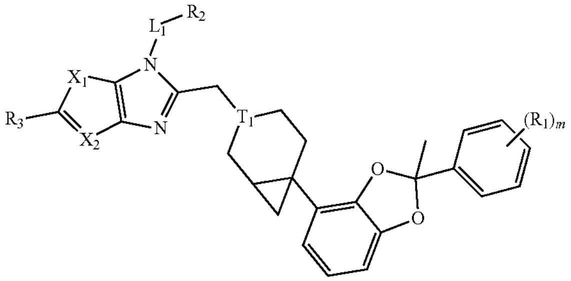

wherein,

=== is selected from a single bond and a double bond, and when $T_2$ is selected from N, === is selected from the single bond;

$R_1$, $R_2$, $R_3$, $L_1$, $T_1$, $T_2$, $X_1$, $X_2$ and m are as defined in the present disclosure.

In some embodiments of the present disclosure, the compound or the pharmaceutically acceptable salt thereof is selected from:

(III-1)

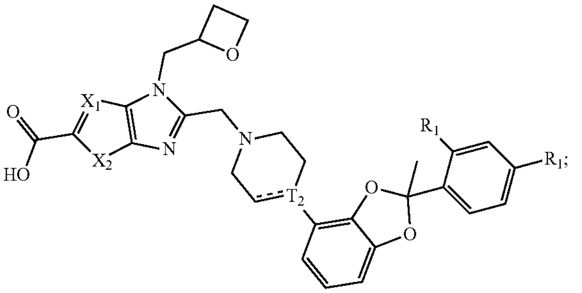

wherein,

=== is selected from a single bond and a double bond, and when $T_2$ is selected from N, === is selected from the single bond;

$R_1$, $T_2$, $X_1$ and $X_2$ are as defined in the present disclosure.

The present disclosure also provides a compound represented by the following formula or a pharmaceutically acceptable salt thereof,

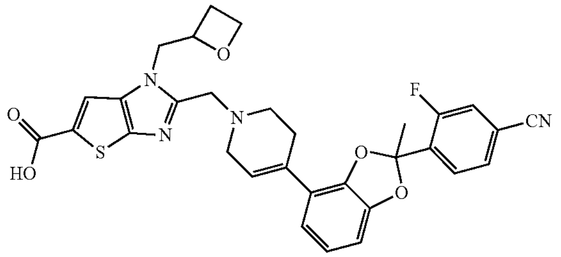

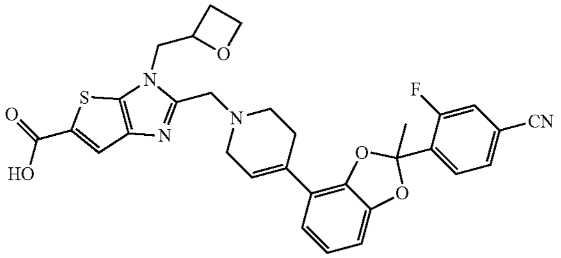

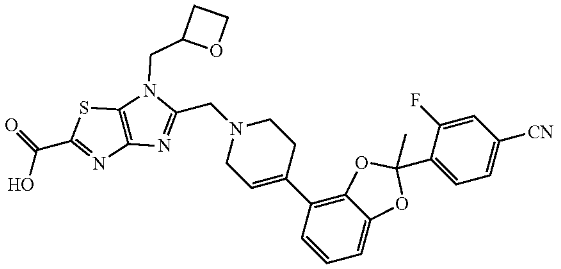

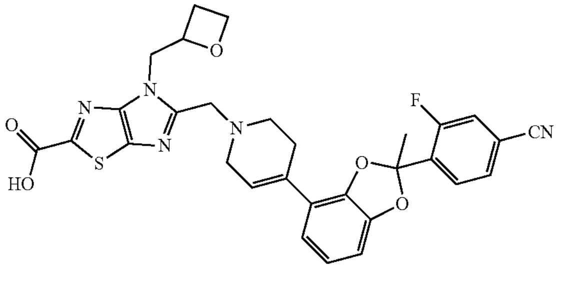

-continued
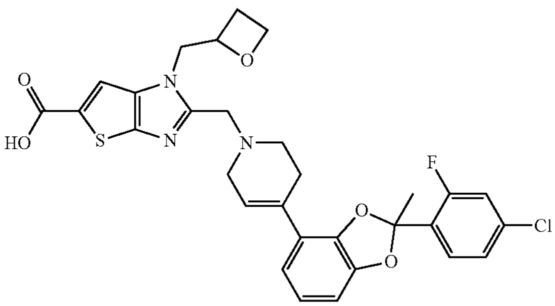
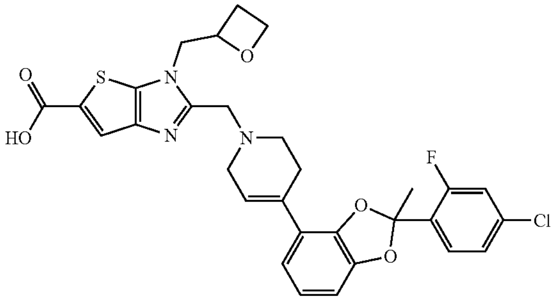
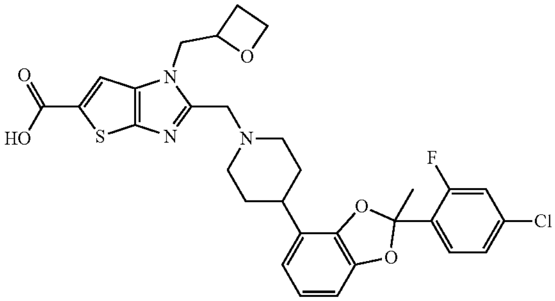
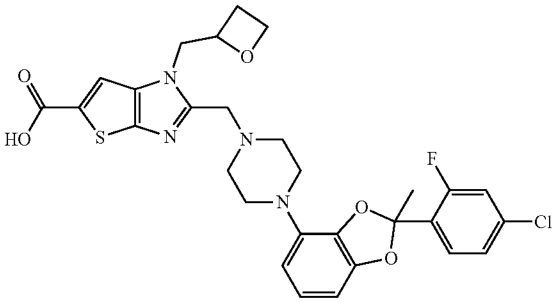
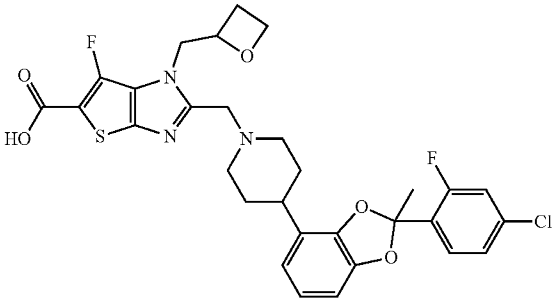
-continued
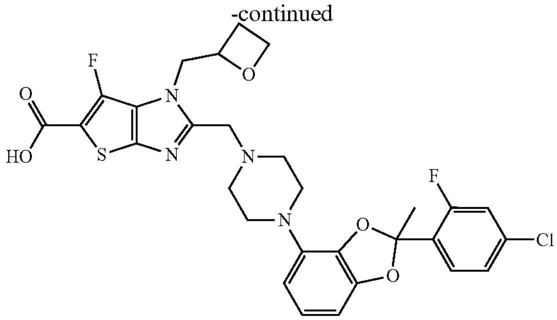
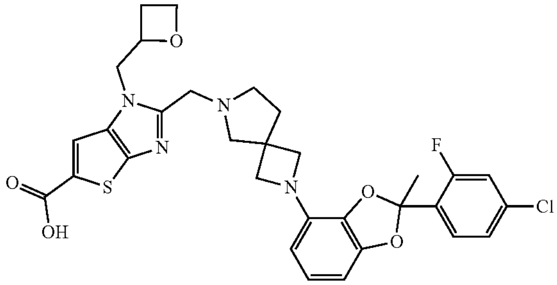
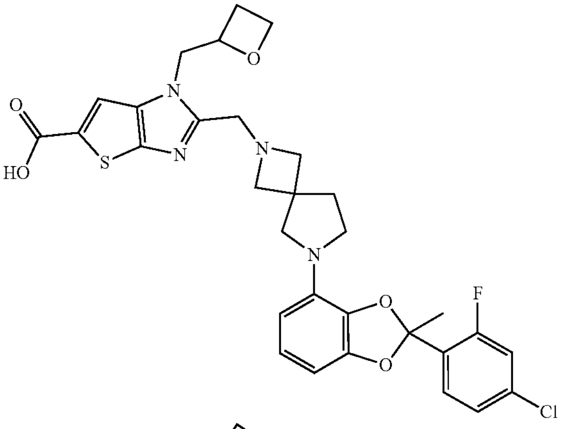
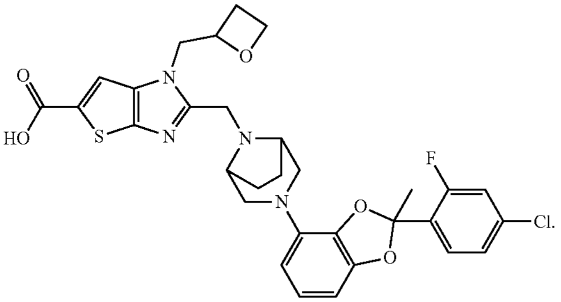
In some embodiments of the present disclosure, the compound or the pharmaceutically acceptable salt thereof is selected from:
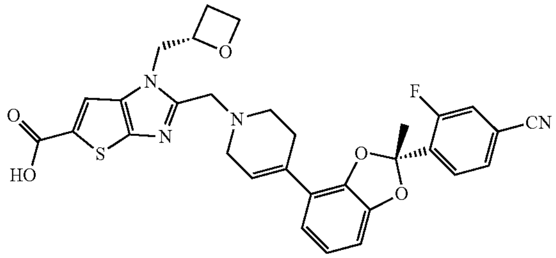

-continued
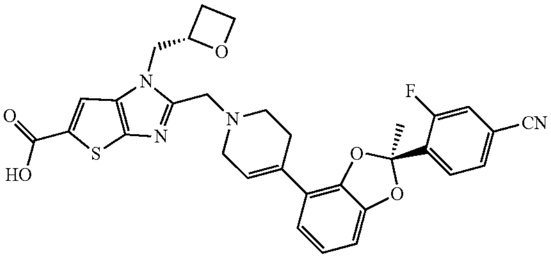
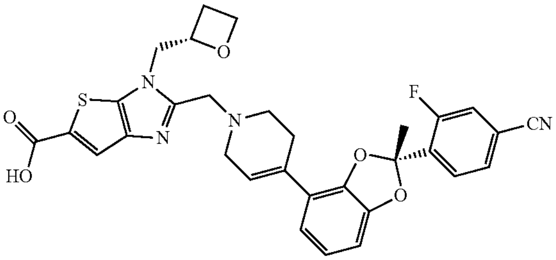
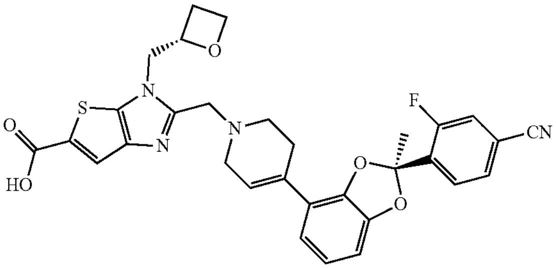
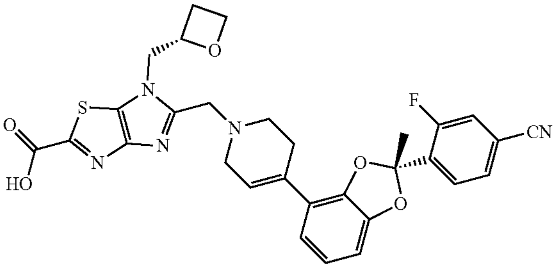
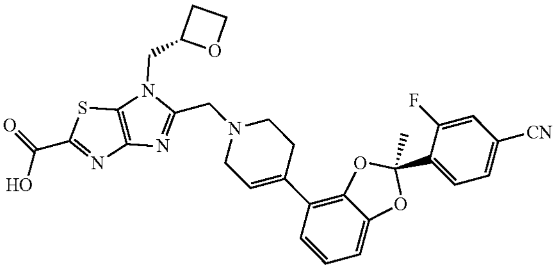
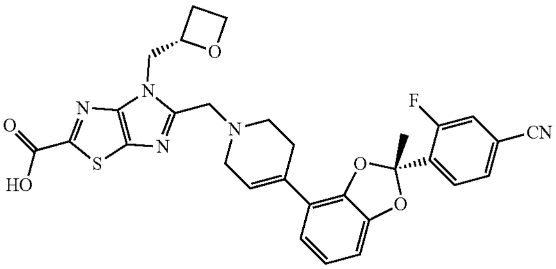
-continued
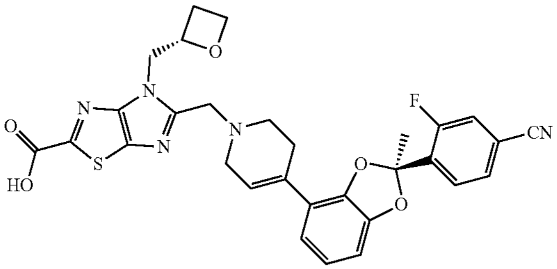
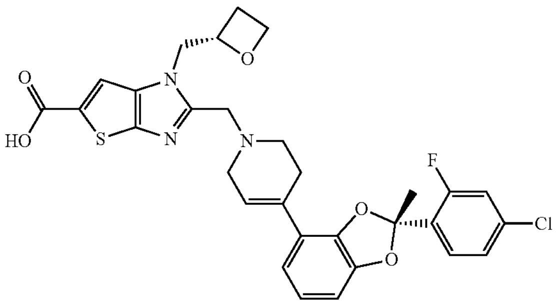
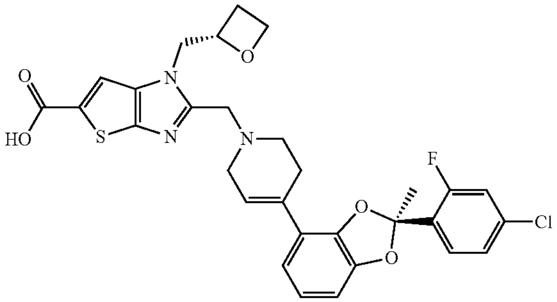
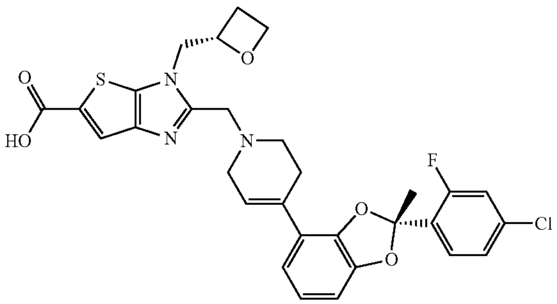
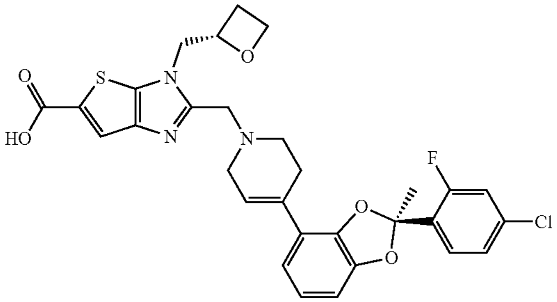

-continued
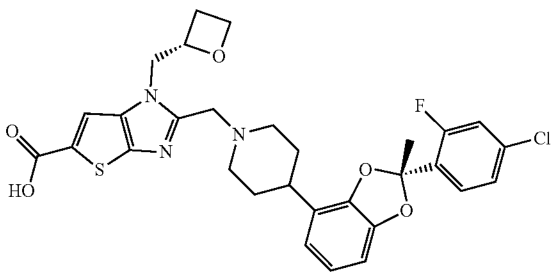
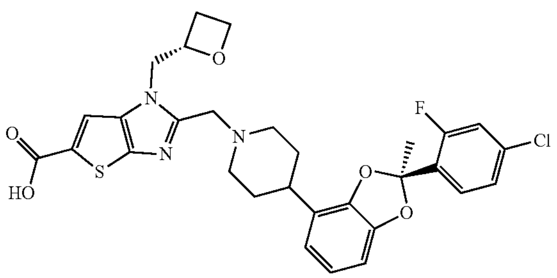
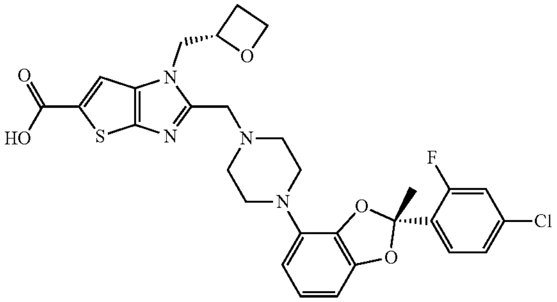
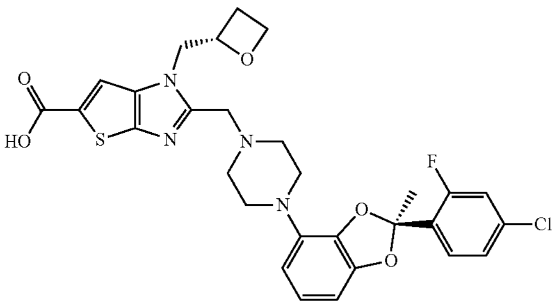
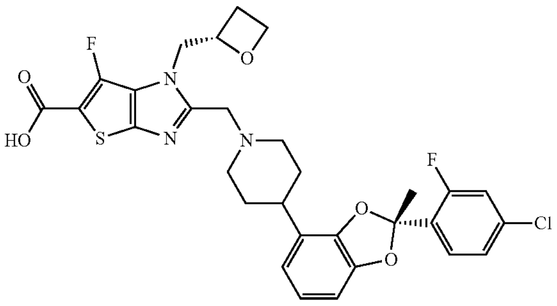
-continued
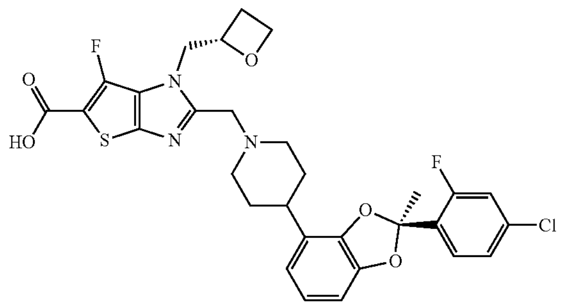
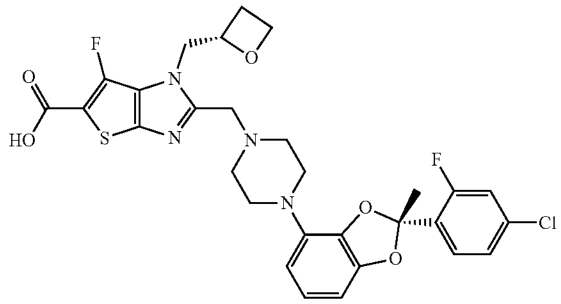
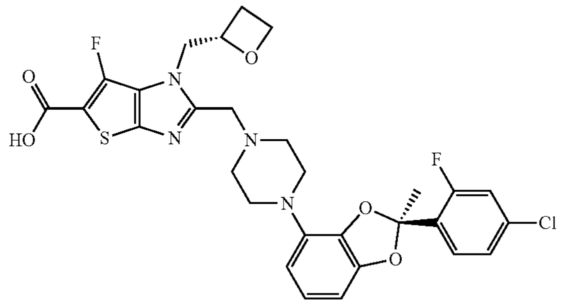
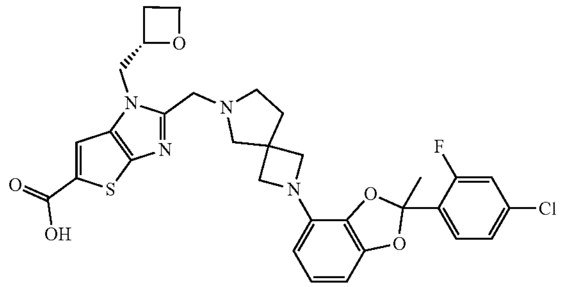
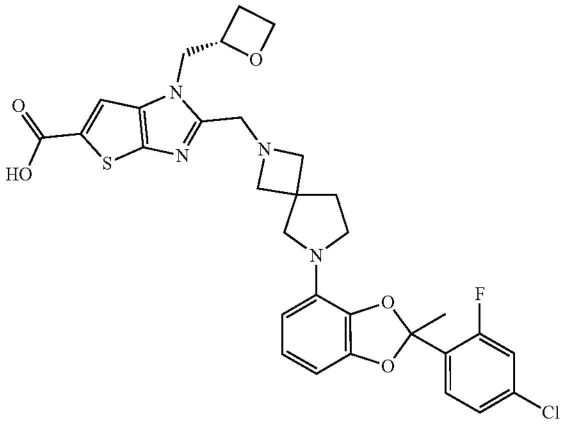

-continued

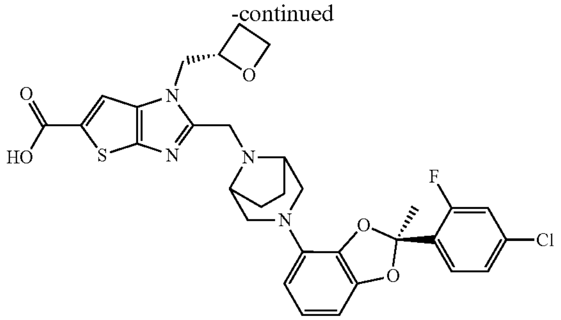

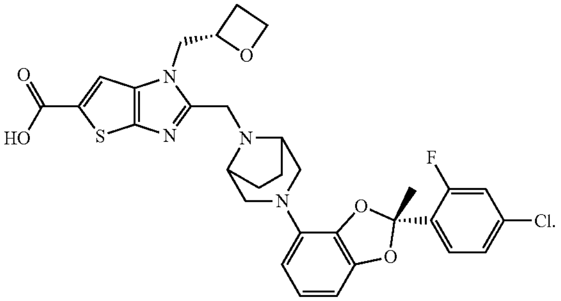

In some embodiments of the present disclosure, disclosed is a use of the compound or the pharmaceutically acceptable salt thereof in the manufacture of a medicament for the treatment of a disease related to a GLP-1 receptor agonist.

In some embodiments of the present disclosure, the use is characterized in, that the medicament related to the GLP-1 receptor agonist is a medicament for the treatment of diabetes.

Technical Effects

The compounds of the present disclosure show a better agonistic ability to GLP-1 receptor; the compounds of the present disclosure have a weak inhibitory effect on human liver microsomal cytochrome P450 isoenzymes and a low risk of "drug-drug interaction", and have no time-dependent inhibitory effect on P450 isoenzyme 2C19; the compounds of the present disclosure show a higher oral exposure in cynomolgus monkeys in vivo and have good pharmacokinetic properties.

Definition and Description

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt may be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt may be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

Unless otherwise specified, the term "isomer" is intended to include geometric isomer, cis-trans isomer, stereoisomer, enantiomer, optical isomer, diastereomer and tautomer.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, or "(−)" refers to levorotation, and or "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ), a wave line ( ) is used to represent a wedged solid bond ( ) or a wedged dashed bond ( ), or the wave line ( ) is used to represent a straight solid bond ( ) or a straight dashed bond ( ).

Unless otherwise specified, the terms “enriched in one isomer”, “enriched in isomers”, “enriched in one enantiomer” or “enriched in enantiomers” refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term “isomer excess” or “enantiomeric excess” refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers, as well as D and L isomers can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure.

The term “optional” or “optionally” means that the subsequent event or condition may occur but not requisite, that the term includes the instance in which the event or condition occurs and the instance in which the event or condition does not occur.

The term “substituted” means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term “optionally substituted” means an atom can be substituted with a substituent or not, unless otherwise specified, the type and number of the substituent may be arbitrary as long as is chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When the number of a substituent is 0, it means that the substituent does not exist, for example, $-A-(R)_0$ means that the structure is actually -A.

When a substituent is vacant, it means that the substituent does not exist, for example, when X is vacant in A-X, the structure of A-X is actually A.

When one of the variables is selected from a single bond, it means that the two groups linked by the single bond are connected directly. For example, when L in A-L-Z represents a single bond, the structure of A-L-Z is actually A-Z.

When a bond of a substituent can be cross-linked to two or more atoms on a ring, such a substituent can be bonded to any atom on the ring, for example, a structural moiety

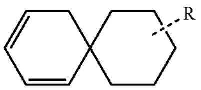 or 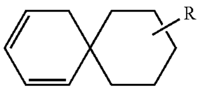

or means that a substituent R can be substituted at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

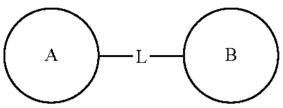

is -M-W-, then -M-W- may link ring A and ring B to form

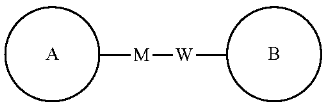

in the direction same as left-to-right reading order, and form

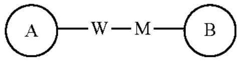

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (), a straight dashed bond () or a wavy line (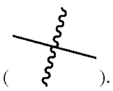).

For example, the straight solid bond in $—OCH_3$ means that it is linked to other groups through the oxygen atom in the group; the straight dashed bonds in

means that it is linked to other groups through the two ends of nitrogen atom in the group; the wave lines in

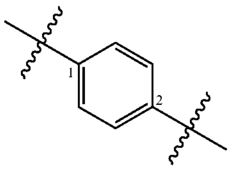 [SMILES: *c1ccc(*)cc1]

means that the phenyl group is linked to other groups through carbon atoms at position 1 and position 2;

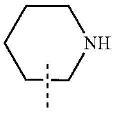

means that it can be linked to other groups through any linkable sites on the piperidinyl by one chemical bond, including at least four types of linkage, including

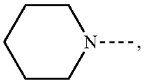, 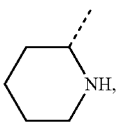, 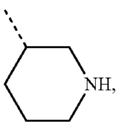,

-continued

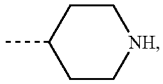,

Even though the H atom is drawn on the —N—,

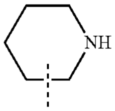

still includes the linkage of

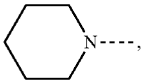, merely when one chemical bond was connected, the H of this site will be reduced by one to the corresponding monovalent piperidinyl.

Unless otherwise specified, the number of atoms on a ring is usually defined as the number of atoms of the ring. For example, "5- to 7-membered ring" refers to a "ring" that surrounds 5-7 atoms.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-3}$ alkylamino" refers to an alkyl group containing 1 to 3 carbon atoms that are connected to the rest of the molecule through an amino group. The $C_{1-3}$ alkylamino includes $C_{1-2}$, $C_3$ and $C_2$ alkylamino, etc. Examples of $C_{1-3}$ alkylamino include, but are not limited to $—NHCH_3$, $—N(CH_3)_2$, $—NHCH_2CH_3$, $—N(CH_3)CH_2CH_3$, $—NHCH_2CH_2CH_3$ and $—NHCH_2(CH_3)_2$, etc.

Unless otherwise specified, "$C_{3-5}$ cycloalkyl" refers to a saturated cyclic hydrocarbon group consisting of 3 to 5 carbon atoms, which is a monocyclic system, and the $C_{3-5}$ cycloalkyl includes $C_{3-4}$ and $C_{4-5}$ cycloalkyl, etc.; it can be monovalent, divalent or polyvalent. Examples of $C_{3-5}$ cycloalkyl include, but are not limited to, cyclopropyl, cyclobutyl, cyclopentyl, etc.

The term "protecting group" includes, but is not limited to "amino protecting group", "hydroxyl protecting group" or "mercapto protecting group". The term "amino protecting group" refers to a protecting group suitable for preventing the side reactions occurring at the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl)methyl; silyl, such as trimethylsilyl (TMS) and tert-butyldimethylsilyl (TBS), etc. The term "hydroxyl protecting group" refers to a protecting group suitable for preventing the side reactions of hydroxyl. Representative hydroxyl protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS), etc.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvents used in the present disclosure are commercially available.

The present disclosure adopts the following abbreviations: aq represents water, eq represents equivalent; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; Cbz represents benzyloxycarbonyl, which is an amine protection group; BOC represents tert-butoxycarbonyl, which is an amine protection group; HOAc represents acetic acid; r.t. represents room temperature; O/N represents overnight; THF represents tetrahydrofuran; $Boc_2O$ represents di-tert-butyl dicarbonate; TFA represents trifluoroacetic acid; DIPEA represents diisopropylethylamine; TEA represents triethylamine; iPrOH represents 2-propanol; mp represents melting point, and AcOH represents acetic acid.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
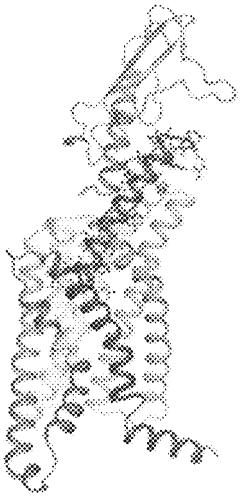
FIG. 1 is the three-dimensional structure of GLP-1/GLP-1 receptor complex.

The present disclosure is described in detail by the embodiments below, but it does not mean that there are any adverse restrictions on the present disclosure. The present disclosure has been described in detail herein, and its specific embodiments have also been disclosed; for one skilled in the art, it is obvious to make various modifications and improvements to the embodiments of the present disclosure without departing from the spirit and scope of the present disclosure.

Reference Embodiment 2: Segment B-2

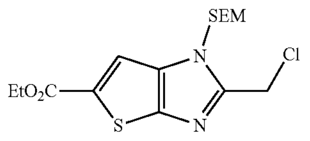 [SMILES: CCOC(=O)c1cc2c(nc(CCl)n2COCC[Si](C)(C)C)s1]

Synthetic Route:

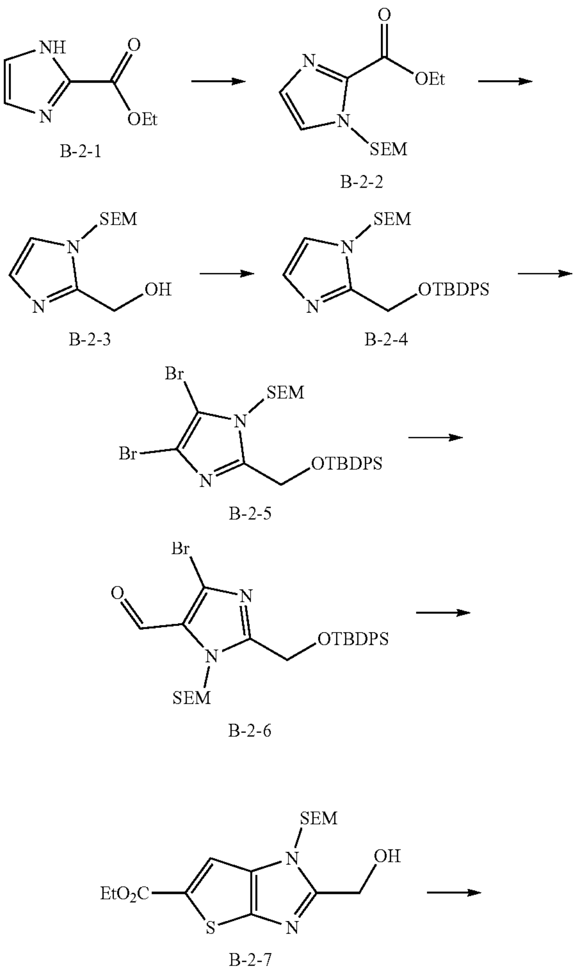

B-2-1 B-2-2 B-2-3 B-2-4 B-2-5 B-2-6 B-2-7

-continued

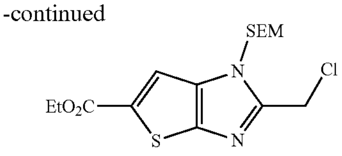

B-2

Step 1: Synthesis of Compound B-2-2

Under the protection of nitrogen, at 0° C., sodium hydride (9.85 g, 246.18 mmol, content of 60%, 1.5 eq) was added to a solution of compound B-2-1 (23 g, 164.12 mmol, 1 eq) in DMF (115 mL). 2-(Trimethylsilyl)ethoxymethyl chloride (41.04 g, 246.18 mmol, 43.57 mL, 1.5 eq) was added dropwise thereto. After the dropwise addition was completed, the reaction was heated to 25° C. and reacted for 12 hours. After the reaction was completed, the reaction was quenched with ice water (500 mL), extracted with ethyl acetate (200 mL*3), and the organic phases were combined, washed with saturated brine (200 mL*2), dried with anhydrous sodium sulfate, and concentrated under reduced pressure to obtain a crude product. The crude product was separated and purified by column chromatography (PE:EA=1:0 to 1:1) to obtain B-2-2. $^1$H NMR (400 MHz, $CDCl_3$) δ ppm −0.07--0.04 (m, 9H), 0.86-0.93 (m, 2H), 1.40 (t, J=7.13 Hz, 3H), 3.49-3.56 (m, 2H), 4.39 (q, J=7.13 Hz, 2H), 7.17 (s, 1H), 5.76 (s, 2H), 7.24 (d, J=0.63 Hz, 1H).

Step 2: Synthesis of Compound B-2-3

Lithium aluminum hydride (6.04 g, 159.21 mmol, 1.5 eq) was dispersed into anhydrous tetrahydrofuran (1000 mL) in batches, cooled to 0° C. under the protection of nitrogen, stirred for 15 minutes, and then compound B-2-2 (28.7 g, 106.14 mmol, 1 eq) was added thereto in batches at 0° C. After the addition was completed, the temperature was raised to 25° C., and the mixture was reacted for 0.5 hours. After the reaction was completed, the mixture was cooled to 0° C., then added with 6 mL of water, 6 mL of 15% sodium hydroxide aqueous solution and 18 mL of water in turn to quench the reaction. The mixture was heated to 25° C. and stirred for 15 minutes, then anhydrous magnesium sulfate was added thereto and stirred for 15 minutes, then filtered. The filtrate was washed with saturated brine (500 mL), dried with anhydrous sodium sulfate and concentrated under reduced pressure to obtain compound B-2-3. $^1$H-NMR (400 MHz, $CDCl_3$) δ ppm −0.02--0.01 (m, 9H), 0.89-0.95 (m, 2H), 3.52 (dd, J=8.76, 7.75 Hz, 2H), 4.72 (s, 2H), 5.37 (s, 2H), 6.93 (d, J=1.13 Hz, 1H), 6.98 (d, J=1.13 Hz, 1H).

Step 3: Synthesis of Compound B-2-4

Under the protection of nitrogen, a mixed solution of compound B-2-3 (18.81 g, 82.37 mmol, 1 eq), tert-butylchlorodiphenylsilane (27.17 g, 98.84 mmol, 25.39 mL, 1.2 eq) and imidazole (14.02 g, 205.92 mmol, 2.5 eq) in DMF (188 mL) was reacted for 16 hours at 25° C. After the reaction was completed, the reaction solution was poured into water (1000 mL) to quench the reaction, and ethyl acetate (200 mL*3) was added for extraction. The organic phases were combined, washed with saturated brine (200 mL*3), dried with anhydrous sodium sulfate, and then concentrated under reduced pressure to obtain a crude product. The crude product was separated and purified by column chromatography (PE:EA=1:0 to 1:1) to obtain B-2-4. $^1$H NMR (400 MHz, $CDCl_3$) δ ppm 0.03 (s, 9H), 0.85-0.91 (m, 2H), 1.06 (s, 9H), 3.41-3.48 (m, 2H), 4.84 (s, 2H), 5.41 (s, 2H), 6.96-7.02 (m, 2H), 7.37-7.46 (m, 6H), 7.66-7.72 (m, 4H).

Step 4: Synthesis of Compound B-2-5

Under the protection of nitrogen, N-bromosuccinimide (25.17 g, 141.40 mmol, 44.18 μL, 3 eq) was added to an anhydrous tetrahydrofuran (440 mL) solution of compound B-2-4 (22 g, 47.13 mmol, 1 eq) in batches, and after the addition was completed, the mixture was heated to 25° C. and reacted for 12 hours. After the reaction was completed, the mixture was added with water (440 mL) to quench, and extracted with ethyl acetate (2200 mL*2). After the organic phases were combined, the organic phase was washed with saturated brine (2200 mL), dried with anhydrous sodium sulfate, and concentrated under reduced pressure to obtain a crude product. The crude product was separated and purified by column chromatography (PE:EA=1:1 to 2:1) to obtain B-2-5. $^1$H NMR (400 MHz, $CDCl_3$) δ ppm 0.02 (s, 9H), 0.85-0.90 (m, 2H), 1.07 (s, 9H), 3.45-3.51 (m, 2H), 4.80 (s, 2H), 5.44 (s, 2H), 7.37-7.48 (m, 6H), 7.64-7.67 (m, 4H).

Step 5: Synthesis of Compound B-2-6

Under the protection of nitrogen, i-PrMgCl—LiCl (1.3 M, 8.13 mL, 1.1 eq) was added dropwise to an anhydrous tetrahydrofuran (60 mL) solution of compound B-2-5 (6 g, 9.61 mmol, 1 eq) at −40° C. stirred for 1.5 hours after the dropwise addition was completed, and then DMF (61.62 g, 843.09 mmol, 64.86 mL, 87.76 eq) was added dropwise thereto. The reaction temperature was raised to 25° C. and the mixture was continued to stir for 30 minutes. After the reaction was completed, water (120 mL) was added to quench the reaction, and the mixture was extracted with ethyl acetate (50 mL*2). The organic phase was washed with saturated brine (100 mL) after the organic phases were combined, and dried with anhydrous sodium sulfate. The organic phase was concentrated under reduced pressure to obtain a crude product. The crude product was separated and purified by column chromatography (PE:EA=1:0 to 10:1) to obtain B-2-6. $^1$H NMR (400 MHz, $CDCl_3$) δ ppm −0.03 (s, 9H), 0.84-0.88 (m, 2H), 1.07 (s, 9H), 3.49-3.54 (m, 2H), 4.86 (s, 2H), 5.85 (s, 2H), 7.38-7.42 (m, 5H), 7.64-7.68 (m, 5H), 9.76 (s, 1H).

Step 6: Synthesis of Compound B-2-7

Compound B-2-6 (1.23 g, 2.14 mmol, 1 eq) was dissolved in ethanol (61.5 mL), and then sodium ethoxide (2.19 g, 6.43 mmol, content of 20%, 3 eq) and ethyl thioglycolate (273.10 mg, 2.57 mmol, 233.42 μL, 1.2 eq) were added thereto in turn, and the reaction was stirred at 20° C. for 2 hours, then heated to 80° C. and stirred for 12 hours. After the reaction was completed, the mixture was added with water (50 mL) to quench, and extracted with ethyl acetate (25 mL*2). After the organic phases were combined, the organic phase was washed with saturated brine (50 mL), and dried with anhydrous sodium sulfate, and then concentrated under reduced pressure to obtain a crude product. The crude product was separated and purified by column chromatography (PE:EA=1:0 to 10:1) to obtain compound B-2-7. $^1$H NMR (400 MHz, $CDCl_3$) δ ppm −0.02 (s, 9H), 0.91-0.96 (m, 2H), 1.40 (t, J=7.13 Hz, 3H), 2.30-2.64 (m, 1H), 3.55-3.61 (m, 2H), 4.39 (q, J=7.13 Hz, 2H), 4.91 (s, 2H), 5.54 (s, 2H), 7.72 (s, 1H).

Step 7: Synthesis of Compound B-2

Under the protection of nitrogen, methanesulfonyl chloride (57.84 mg, 504.89 μmol, 39.08 μL, 1.5 eq) was added to a solution of compound B-2-7 (120 mg, 336.59 μmol, 1 eq) and triethylamine (102.18 mg, 1.01 mmol, 140.55 μL, 3 eq) in dichloromethane (2 mL) in batches, and the temperature was raised to 25° C. and the mixture was reacted for 12 hours. After the reaction was completed, the mixture was concentrated under reduced pressure to obtain a crude product. The crude product was separated and purified by preparative thin layer chromatography (DCM:MeOH=20:1) to obtain compound B-2. $^{1}H$ NMR (400 MHz, $CDCl_3$) δ ppm −0.02 (s, 9H), 0.92-0.97 (m, 2H), 1.40 (t, J=7.13 Hz, 3H), 3.56-3.61 (m, 2H), 4.39 (q, J=7.13 Hz, 2H), 4.85 (s, 2H), 5.57 (s, 2H), 7.72 (s, 1H)

Reference Embodiment 3: Segments B-3 and B-4

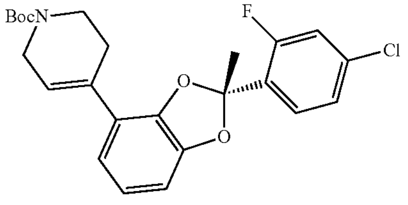

B-3 or B-4

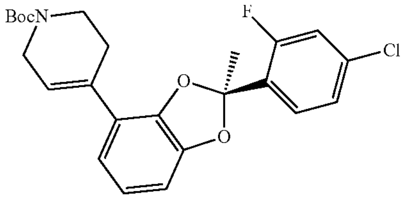

B-4 or B-3

Synthetic Route:

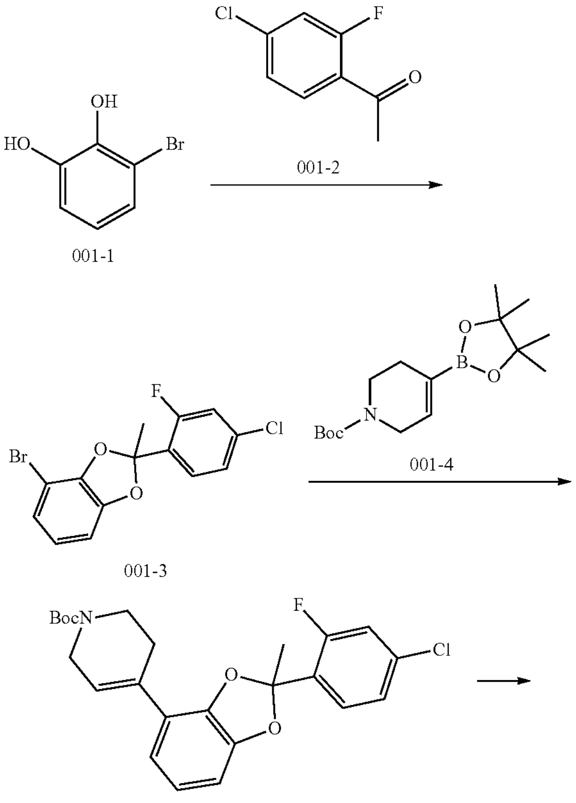

-continued

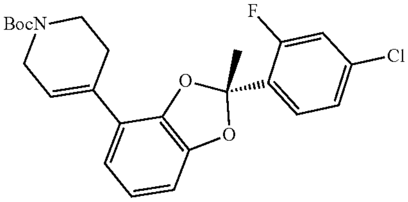

+

B-3 or B-4

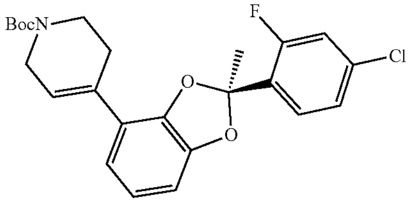

B-4 or B-3

Step 1: Synthesis of Compound 001-3

001-1 (4 g, 21.16 mmol, 1 eq), toluene (60 mL), 001-2 (3.84 g, 22.25 mmol, 1.05 eq), p-toluenesulfonic acid monohydrate (200.00 mg, 1.05 mmol, 0.05 eq) were added to a reaction flask, and water segregator was used to build a water separator, and the mixture was refluxed at 140-145° C. for 60 hours. After the reaction was completed, the reaction solution was evaporated to dryness by rotary evaporation to obtain a crude product. The crude product was purified by column chromatography (petroleum ether) to obtain 001-3. $^{1}H$ NMR (400 MHz, $CDCl_3$) δ ppm 2.12 (d, J=1.2 Hz, 3H), 6.68-6.79 (m, 2H), 6.96 (dd, J=8.0, 1.6 Hz, 1H), 7.12-7.19 (m, 2H), 7.52-7.59 (m, 1H).

Step 2: Synthesis of Compound 001-5

001-3 (0.68 g, 1.98 mmol, 1 eq), 001-4 (660 mg, 2.13 mmol, 1.08 eq), trakis(triphenylphosphine)palladium (114.35 mg, 98.96 μmol, 0.05 eq), potassium carbonate (547.07 mg, 3.96 mmol, 2 eq), water (1.4 mL) and 1,4-dioxane (7 mL) were added to a reaction flask, and the system was replaced with nitrogen, and the mixture was reacted for 16 hours at 100° C. under the protection of nitrogen. After the reaction was completed, the reaction solution was evaporated to dryness by rotary evaporation obtain a crude product. The crude product was purified by column chromatography (PE:EA=27:1) to obtain 001-5. $^{1}H$ NMR (400 MHz, $CDCl_3$) δ ppm 1.50 (s, 9H), 2.08 (s, 3H), 2.46-2.66 (m, 2H), 3.57-3.70 (m, 2H), 4.09-4.13 (m, 2H), 6.37 (br s, 1H), 6.72-6.78 (m, 1H), 6.78-6.84 (m, 2H), 7.10-7.18 (m, 2H), 7.51 (t, J=8.4 Hz, 1H).

Step 3: Synthesis of Compound B-3 and B-4

001-5 was purified and separated by supercritical fluid separation (chromatographic column: DAICEL CHIRALCEL OJ (250 mm*50 mm, 10 μm); mobile phase: phase A was $CO_2$; phase B was [0.1% ammonia water—isopropanol]; B %: 15%-15%) to obtain B-3 (retention time: 2.474 min) and B-4 (retention time: 2.771 min).

Reference Embodiment 4: Segment B-5

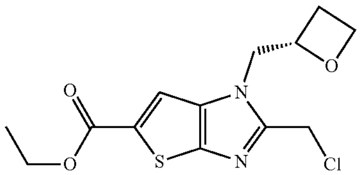

B-5

Synthetic Route:

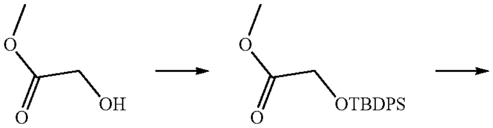

B-5-1

B-5-2

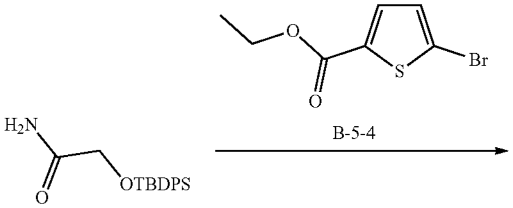

B-5-4

B-5-3

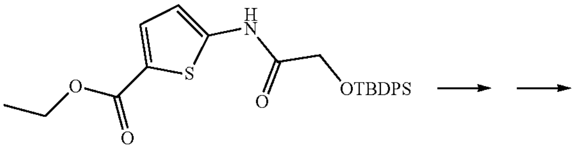

B-5-5

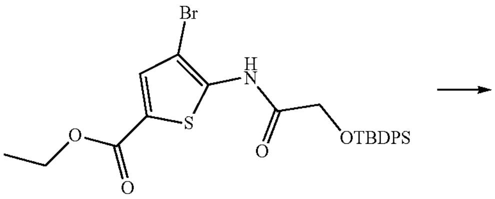

B-5-6

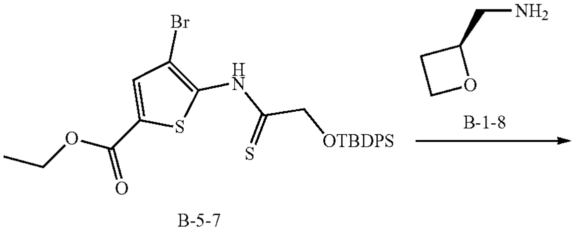

B-1-8

B-5-7

-continued

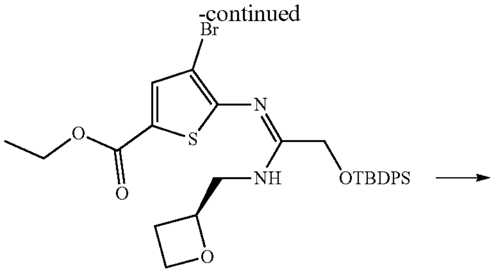

B-5-8

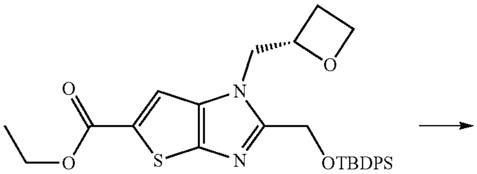

B-5-9

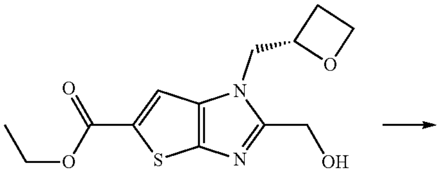

B-5-10

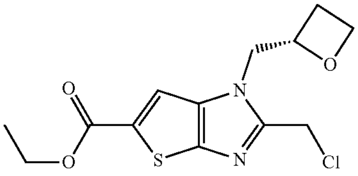

B-5

Step 1: Synthesis of compound B-5-2

B-5-1 (10.00 g, 111.02 mmol, 8.55 mL, 1 eq), tert-butylchlorodiphenylsilane (36.62 g, 133.22 mmol, 34.22 mL, 1.2 eq), imidazole (8.92 g, 131.00 mmol, 1.18 eq), anhydrous DMF (150.00 mL) were added to a reaction flask, and the reaction system was stirred at 0° C. for 3 hours. The reaction solution was concentrated to obtain a crude product, dissolved with ethyl acetate (200 mL). The mixture was washed with water (200 mL*2) and saturated brine (30 mL) in turn, dried with anhydrous sodium sulfate, filtered, and the filtrate was concentrated to obtain a crude product. The crude product was separated and purified by column chromatography (PE:EA=1:0 to 10:1) to obtain compound B-5-2. $^1$H NMR (400 MHz, $CDCl_3$) δ ppm 1.10 (s, 9H), 3.69 (s, 3H), 4.26 (s, 2H), 7.37-7.45 (m, 6H), 7.69 (dd, J=7.88, 1.38 Hz, 4H).

Step 2: Synthesis of Compound B-5-3

In a dry reaction flask, B-5-2 (220 g, 669.76 mmol, 12.82 mL, 1 eq) was added to a methanol solution of ammonia (7 M, 1.58 L, 16.5 eq), and the mixture was stirred at 50° C. for 10 hours. The reaction solution was concentrated, and then separated and purified by column chromatography (PE: EA=1:0 to 3:1) to obtain compound B-5-3. $^1$H NMR (400 MHz, DMSO-$d_6$) δ ppm 1.02 (s, 9H), 3.94 (s, 2H), 7.11 (br s, 1H), 7.40 (br s, 1H), 7.42-7.52 (m, 6H), 7.64 (dd, J=7.91, 1.63 Hz, 4H).

Step 3: Synthesis of Compound B-5-5

B-5-4 (68.5 g, 291.37 mmol, 1 eq), B-5-3 (100.47 g, 320.51 mmol, 1.1 eq), cesium carbonate (142.4 g, 437.06 mmol, 1.5 eq), anhydrous 1,4-dioxane (1 L) were added to a reaction flask, and then tris(dibenzylideneacetone)dipalladium (26.68 g, 29.14 mmol, 0.1 eq), 4,5-bis(diphenylphosphino)-9,9-dimethylxanthene (16.86 g, 29.14 mmol, 0.1 eq) were added thereto under nitrogen atmosphere, and the reaction system was stirred at 110° C. for 1 hour. Water (1 L) was added for dilution, and the mixture was extracted with ethyl acetate (1 L*3). After the phases were separated, the organic phase was collected, washed with saturated brine solution (1 L*3) in turn, dried with anhydrous sodium sulfate, and concentrated under reduced pressure to obtain a product. The product was purified by column chromatography (PE:EA=1:0 to 10:1) to obtain compound B-5-5.

Step 4: Synthesis of Compound B-5-6

In a dry reaction flask, B-5-5 (25 g, 53.46 mmol, 1 eq) was added to tetrahydrofuran (250 mL), and then N-bromosuccinimide (9.99 g, 56.13 mmol, 1.05 eq) was added thereto, and stirred at 20° C. for 2 hours. The reaction solution was poured into 1.2 L of sodium bicarbonate aqueous solution, added with ethyl acetate (1.2 L*2) for extraction. The organic phases were combined, washed with saturated brine (1.2 L*2), and after the phases were separated, the organic phase was dried with anhydrous sodium sulfate, filtered, and the filtrate was evaporated to dryness by rotary evaporation under reduced pressure. Compound B-5-6 was obtained.

Step 5: Synthesis of Compound B-5-7

In a dry reaction flask, B-5-6 (100 g, 182.97 mmol, 1 eq) was added to 1,4-dioxane (11 L), and Lawesson reagent (74.00 g, 182.97 mmol, 1 eq) was added thereto, and the mixture was heated to 110° C. and stirred for 3 hours. The reaction solution was concentrated, and then separated and purified by column chromatography (PE:EA=1:0 to 3:1) to obtain compound B-5-7. $^1H$ NMR (400 MHz, $CDCl_3$) δ ppm 1.20 (s, 9H), 1.39 (t, J=7.15 Hz, 3H), 4.37 (q, J=7.11 Hz, 2H), 4.63 (s, 2H), 7.39-7.52 (m, 6H), 7.67 (dd, J=8.03, 1.25 Hz, 4H), 7.73 (s, 1H), 11.24 (br s, 1H).

Step 6: Synthesis of Compound B-5-8

In a dry reaction flask, B-5-7 (5 g, 8.89 mmol, 1 eq) was added to DMF (1 mL), and then silver acetate (2.97 g, 17.77 mmol, 910.03 μL, 2 eq) and B-1-8 (1.55 g, 17.77 mmol, 2 eq) was added thereto, and the mixture was stirred at 30° C. for 10 hours. The reaction solution was filtered, added with water (100 mL) to dilute the filtrate, and then ethyl acetate (100 mL*3) was added for extraction. After the phases were separated, the organic phase was collected, washed with saturated brine solution (100 mL*3) in turn, dried with anhydrous sodium sulfate, and concentrated under reduced pressure. The residue was separated and purified by column chromatography (PE:EA=1:0 to 3:1) to obtain compound B-5-8. LCMS, m/z=617.0 [M+1]+.

Step 7: Synthesis of Compound B-5-9

In a dry reaction flask, B-5-8 (3.8 g, 6.17 mmol, 1 eq) was added to DMF (40 mL), and then cuprous iodide (352.66 mg, 1.85 mmol, 0.3 eq), N,N'-dimethylethylenediamine (326.45 mg, 3.70 mmol, 398.60 μL, 0.6 eq), cesium carbonate (2.01 g, 6.17 mmol, 1 eq) were added thereto, and the mixture was stirred at 60° C. for 10 hours. Additional cuprous iodide (352.66 mg, 1.85 mmol, 0.3 eq), N,N'-dimethylethylenediamine (326.46 mg, 3.70 mmol, 398.61 μL, 0.6 eq) were added thereto, and the mixture was continued to stir for 4 hours. Water (100 mL) was added for dilution, and ethyl acetate (100 mL*3) was added for extraction. After the phases were separated, the organic phase was collected, washed with saturated brine solution (100 mL*3) in turn, dried with anhydrous sodium sulfate, and concentrated under reduced pressure. Compound B-5-9 was obtained. LCMS, m/z=535.3 [M+1]+.

Step 8: Synthesis of Compound B-5-10

In a dry reaction flask, B-5-9 (2 g, 3.15 mmol, purity of 84.334%, 1 eq) was added to tetrahydrofuran (20 mL), and then triethylamine trihydrofluoride (2.54 g, 15.77 mmol, 2.57 mL, 5 eq) was added thereto, and the mixture was stirred at 20° C. for 10 hours. Water (30 mL) was added for dilution, and ethyl acetate (30 mL*3) was added for extraction. After the phases were separated, the organic phase was collected, washed with saturated sodium bicarbonate aqueous solution (30 mL), saturated brine solution (30 mL*3) in turn, dried with anhydrous sodium sulfate, and concentrated under reduced pressure. tert-Butyl methyl ether (10 mL) and ethyl acetate (1 mL) were added to slurry, filtered, and the filter cake was washed with tert-butyl methyl ether (10 mL), and the filter cake was concentrated under reduced pressure. Compound B-5-10 was obtained. LCMS, m/z=297.1 [M+1]+.

Step 9: Synthesis of Compound B-5-11

B-5-10 (0.8 g, 2.70 mmol, 1 eq), dichloromethane (10 mL) and triethylamine (819.51 mg, 8.10 mmol, 1.13 mL, 3 eq) were added to a dry reaction flask, and the system was replaced with nitrogen, cooled to 0° C., and added with methanesulfonyl chloride (463.86 mg, 4.05 mmol, 313.42 μL, 1.5 eq), then the mixture was stirred at 20° C. for 3 hours. The reaction solution was poured into water (20 mL) for quenching, added with dichloromethane (20 mL*3) for extraction. After the phases were separated, the organic phase was collected, washed with saturated brine solution (20 mL*3) in turn, dried with anhydrous sodium sulfate, concentrated under reduced pressure, and separated and purified by column chromatography (PE:EA=1:0 to 3:1). Compound B-5 was obtained. LCMS, m/z=315.1 [M+1]$^+$.

Reference Embodiment 5: Segment B-6

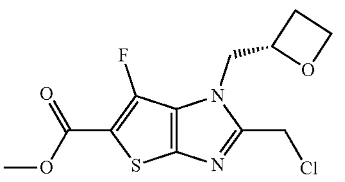

Synthetic Route:

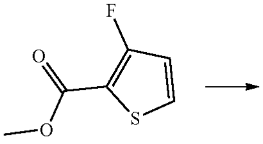

B-6-1

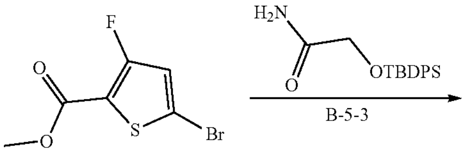

B-6-2

-continued

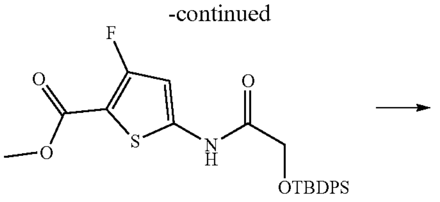

B-6-3

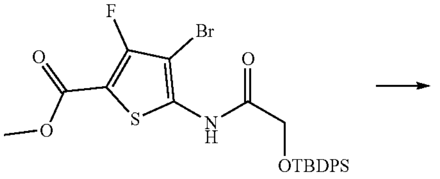

B-6-4

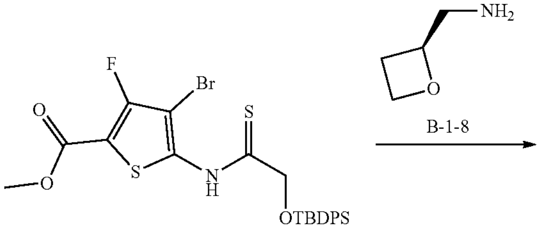

B-1-8

B-6-5

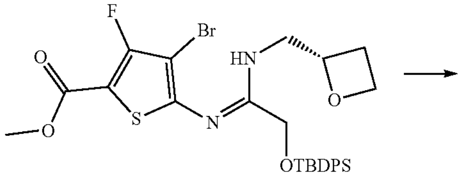

B-6-6

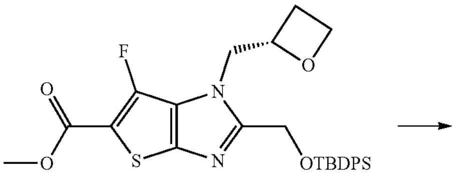

B-6-7

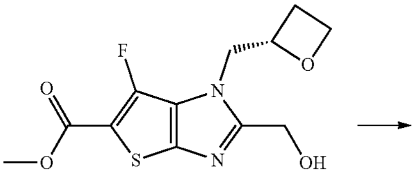

B-6-8

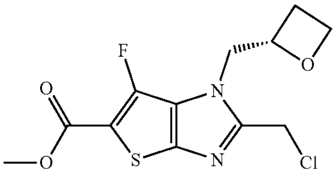 [SMILES: COC(=O)c1sc2nc(CCl)n(C[C@@H]3CCO3)c2c1F]

B-6

Step 1: Synthesis of Compound B-6-2

B-6-1 (2.00 g, 12.49 mmol, 1 eq) and anhydrous tetrahydrofuran (100 mL) were added to a reaction flask, and then 2,2,6,6-tetramethylpiperidinylmagnesium chloride lithium chloride complex (1 M, 24.00 mL, 1.92 eq) was added thereto at −40° C., and the reaction system was stirred at −40° C. for 0.5 hours. Carbon tetrabromide (4.14 g, 12.49 mmol, 1 eq) was added thereto, and the reaction system was stirred at −40° C. for 0.5 hours, and the reaction system was stirred at 20° C. for 11 hours. Hydrochloric acid (0.5 M, 10 mL) was added to the reaction solution to quench the reaction, and the mixture was extracted with ethyl acetate (50 mL*3). The organic phases were combined, washed with saturated brine (50 mL), dried over anhydrous sodium sulfate, filtered, and the filtrate was concentrated to obtain a crude product. The crude product was separated and purified by column chromatography (PE:EA=1:0-20:1) to obtain compound B-6-2. $^1$H NMR (400 MHz, $CDCl_3$) δ ppm 3.88 (s, 3H), 6.89 (s, 1H).

Step 2: Synthesis of Compound B-6-3

B-6-2 (1.70 g, 7.11 mmol, 1 eq), B-5-3 (2.23 g, 7.11 mmol, 1.0 eq), potassium carbonate (1.97 g, 14.22 mmol, 2 eq), anhydrous toluene (50 mL) were added to a reaction flask, and then tris(dibenzylideneacetone)dipalladium (0.65 g, 709.82 μmol, 0.10 eq), 4,5-bis(diphenylphosphino)-9,9-dimethylxanthene (0.82 g, 1.42 mmol, $1.99e^{-1}$ eq) were added thereto under nitrogen atmosphere, and then the reaction system was stirred at 100° C. for 12 hours. The reaction solution was filtered, and water (50 mL) was added to the filtrate, and the mixture was extract with ethyl acetate (50 mL*3). The organic phases were combined, washed with saturated brine (50 mL), dried with anhydrous sodium sulfate, filtered, and the filtrate was concentrated to obtain a crude product. The crude product was separated and purified by column chromatography (PE:EA=1:0-4:1) to obtain compound B-6-3. $^1$H NMR (400 MHz, $CDCl_3$) δ ppm 1.16 (s, 9H), 3.87 (s, 3H), 4.31 (s, 2H), 6.42 (s, 1H), 7.41-7.47 (m, 5H), 7.57-7.68 (m, 5H), 9.28 (br s, 1H).

Step 3: Synthesis of Compound B-6-4

B-6-3 (2.60 g, 2.84 mmol, purity of 51.53%, 1 eq), N-bromosuccinimide (1.00 g, 5.62 mmol, 1.98 eq) and anhydrous THF (50 mL) were added to a reaction flask, and the reaction system was stirred at 20° C. for 12 hours. Saturated sodium bicarbonate solution (50 mL) was added to the reaction solution, and the mixture was extracted with ethyl acetate (50 mL*3). The organic phases were combined, washed with saturated brine (50 mL), dried with anhydrous sodium sulfate, filtered, and the filtrate was concentrated to obtain a crude product. The crude product was separated and purified by column chromatography (PE:EA=1:0-10:1) to obtain compound B-6-4. $^1$H NMR (400 MHz, $CDCl_3$) δ ppm 1.19 (s, 9H), 3.89 (s, 3H), 4.31 (s, 2H), 7.42-7.50 (m, 6H), 7.66 (br d, J=6.78 Hz, 4H), 9.65 (br s, 1H).

Step 4: Synthesis of Compound B-6-5

B-6-4 (1.80 g, 3.27 mmol, 1 eq), Lawesson reagent (1.35 g, 3.34 mmol, 1.02 eq) and anhydrous dioxane (30 mL) were added to a reaction flask, and the reaction system was stirred at 110° C. for 6 hours. The reaction solution was cooled to room temperature and concentrated to obtain a crude product. The crude product was separated and purified by column chromatography (PE:EA=1:0-10:1) to obtain compound B-6-5. $^1$H NMR (400 MHz, $CDCl_3$) δ ppm 1.20 (s, 9H), 3.91 (s, 3H), 4.60 (s, 2H), 7.40-7.51 (m, 6H), 7.66 (dd, J=7.91, 1.38 Hz, 4H), 11.18 (br s, 1H).

Step 5: Synthesis of Compound B-6-6

B-6-5 (1.50 g, 2.65 mmol, 1 eq), B-1-8 (0.60 g, 6.89 mmol, 2.60 eq), silver acetate (0.90 g, 5.39 mmol, 276.07 μL, 2.04 eq), anhydrous DMF (20 mL) were added to a reaction flask, and the reaction system was stirred at 20° C. for 16 hours. The reaction solution was filtered, and water (50 mL) was added to the filtrate, and the mixture was extracted with ethyl acetate (50 mL*3). The organic phases were combined, washed with saturated brine (50 mL*3), dried with anhydrous sodium sulfate, filtered, and the filtrate was concentrated to obtain a crude product. The crude product was separated and purified by column chromatography (PE:EA=1:0-5:1) to obtain compound B-6-6. $^1$H NMR (400 MHz, $CDCl_3$) δ ppm 1.10 (s, 9H), 2.55-2.66 (m, 1H), 2.67-2.78 (m, 1H), 3.56-3.66 (m, 1H), 3.77-3.88 (m, 4H), 4.31-4.45 (m, 2H), 4.53 (dt, J=9.22, 5.93 Hz, 1H), 4.68-4.78 (m, 1H), 5.05-5.17 (m, 1H), 6.95 (br s, 1H), 7.39-7.52 (m, 6H), 7.63 (br t, J=5.65 Hz, 4H).

Step 6: Synthesis of Compound B-6-7

B-6-6 (0.80 g, 1.29 mmol, 1 eq), N,N'-dimethylethylenediamine (0.16 g, 1.82 mmol, 195.36 μL, 1.41 eq), acetonitrile (10 mL) were added to a reaction flask, and cuprous iodide (0.16 g, 840.12 μmol, 0.65 eq) was added thereto under nitrogen atmosphere, and the reaction system was stirred at 80° C. for 10 hours. The reaction solution was filtered, added with water (20 mL), and extracted with ethyl acetate (20 mL*3). The organic phases were combined, washed with saturated brine (20 mL*3), dried with anhydrous sodium sulfate, filtered, and the filtrate was concentrated to obtain a crude product. The crude product was separated and purified by thin layer chromatography silica gel plate (PE:EA=3:1) to obtain compound B-6-7.

Step 7: Synthesis of Compound B-6-8

B-6-7 (0.40 g, 742.52 μmol, 1 eq) and anhydrous tetrahydrofuran (5 mL) were added to a reaction flask, then tetrabutylammonium fluoride (1 M, 1.00 mL, 1.35 eq) was added thereto, and the reaction system was stirred at 20° C. for 1 hour. The reaction solution was added with water (20 mL) and extracted with ethyl acetate (20 mL*3). The organic phases were combined, washed with saturated brine (20 mL*3), dried with anhydrous sodium sulfate, filtered, and the filtrate was concentrated to obtain a crude product. The crude product was separated and purified by column chromatography (PE:EA=1:0-0:1) to obtain compound B-6-8. $^1$H NMR (400 MHz, $CDCl_3$) δ ppm 2.48-2.58 (m, 1H), 2.78-2.89 (m, 1H), 3.91 (s, 3H), 4.40-4.56 (m, 3H), 4.67-4.74 (m, 1H), 4.80-4.90 (m, 2H), 5.19 (qd, J=6.90, 2.89 Hz, 1H).

Step 8: Synthesis of Compound B-6

B-6-8 (30 mg, 99.90 μmol, 1 eq) and anhydrous dichloromethane (2 mL) were added to a reaction flask, and methanesulfonyl chloride (30 mg, 261.89 μmol, 20.27 μL, 2.62 eq) and triethylamine (30 mg, 296.47 μmol, 41.27 μL, 2.97 eq) were added thereto at 0° C., then the reaction system was stirred at 20° C. for 1 hour. Saturated sodium bicarbonate solution (0.5 mL) was added to the reaction solution for quenching the reaction, and the mixture was concentrated to obtain compound B-6. LCMS: m/z=318.8 $[M+1]^+$.

Reference Embodiment 6: Segments B-7 and B-8

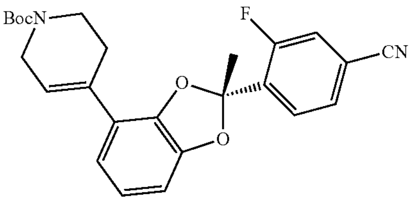

B-7 or B-8

-continued

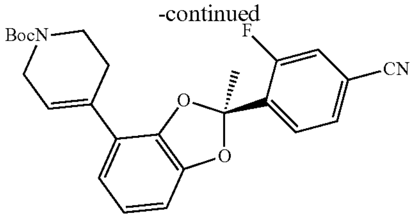

B-8 or B-7

Synthetic Route:

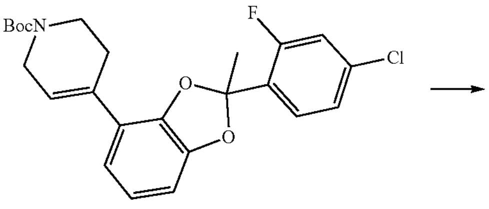

001-5

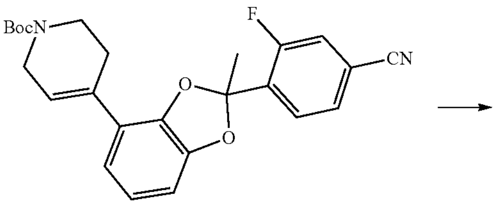

001-6

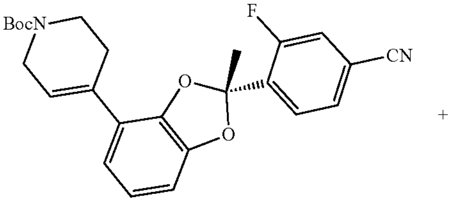

B-7 or B-8

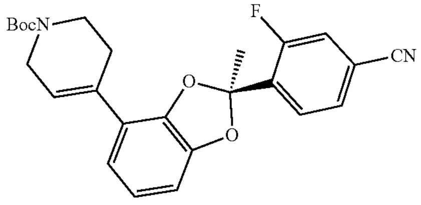

B-8 or B-7

Step 1: Synthesis of Compound 001-6

001-5 (0.76 g, 1.70 mmol, 1 eq), $Zn(CN)_2$ (340 mg, 2.90 mmol, 183.78 μL, 1.70 eq), tetrakis(triphenylphosphine) palladium (197 mg, 170.48 μmol, 0.1 eq), DMF (8 mL) were added to a reaction flask, reacted for 16 hours at 120° C. under the protection of nitrogen. After the reaction was completed, the reaction solution was filtered, and the filtrate was added with 25 mL of water, extracted with ethyl acetate (25 mL*3). The organic phases were combined, washed with 25 mL of saturated brine, dried with anhydrous sodium sulfate, filtered and evaporated to dryness by rotary evaporation to obtain a crude product. The crude product was purified by column chromatography (PE:EA=19:1) to obtain 001-6.

Step 2: Synthesis of Compounds B-7 and B-8

001-6 (520 mg, 1.19 mmol, 1 eq) was separated by supercritical fluid (chromatographic column: DAICEL CHIRALPAK AD (250 mm*30 mm, 10 m); mobile phase: phase A was $CO_2$, phase B was [0.1% $NH_3H_2O$ EtOH]; B %: 15%-15%) to obtain compound B-7 (the retention time was 0.742 min) and compound B-8 (the retention time was 0.846 min). LCMS: m/z=381.0 $[M-55]^+$.

Embodiment 4

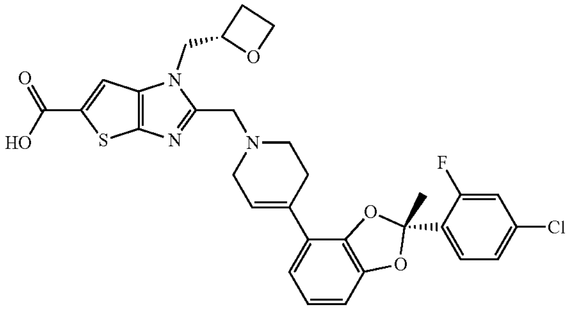

003A or 003B or 003C or 003D

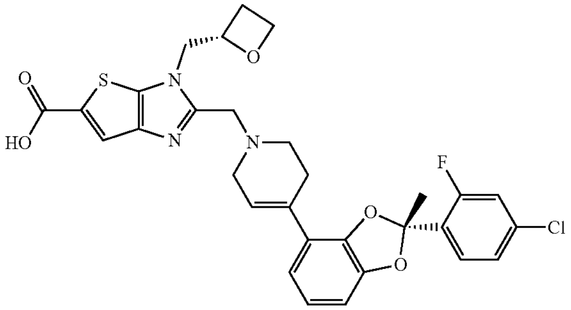

003B or 003A or 003D or 003C

-continued

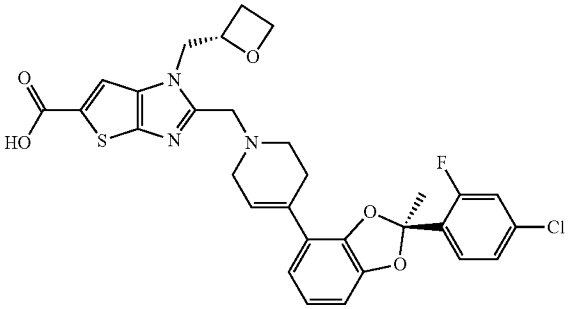

003C or 003D or 003A or 003B

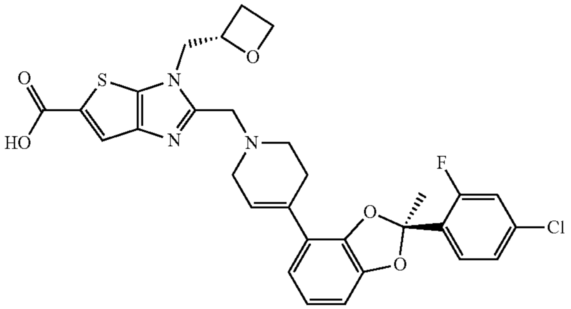

003D or 003C or 003B or 003A

Synthetic Route:

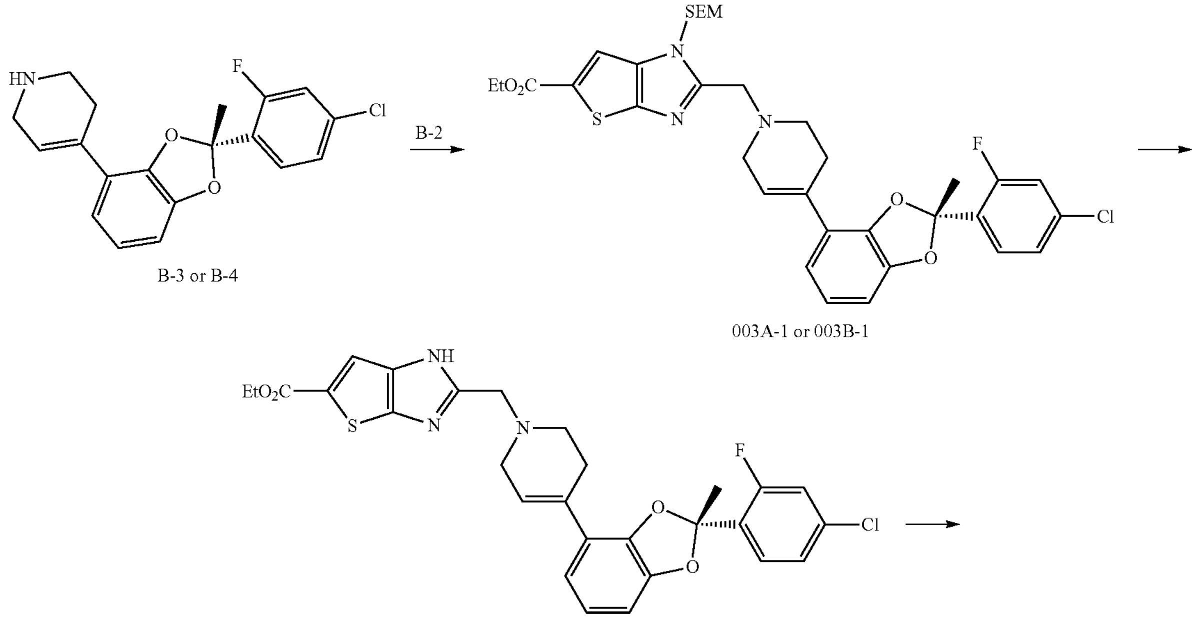

B-3 or B-4

003A-1 or 003B-1

003A-2 or 003B-2

-continued
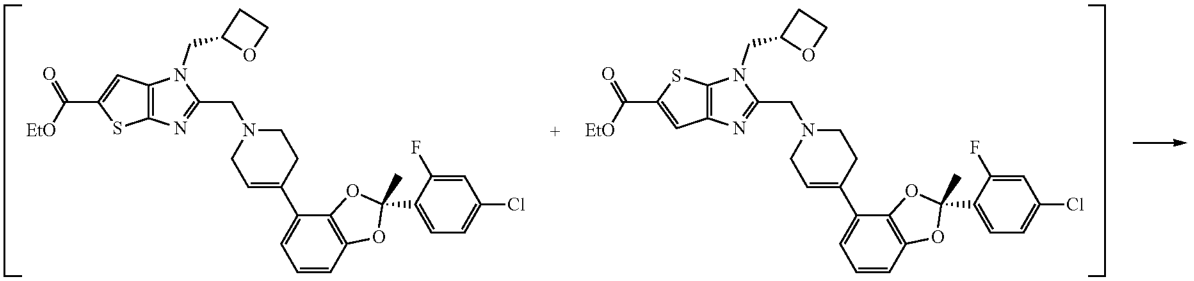
Mixture of 003A-3 or 003B-3 and 003C-3 or 003D-3
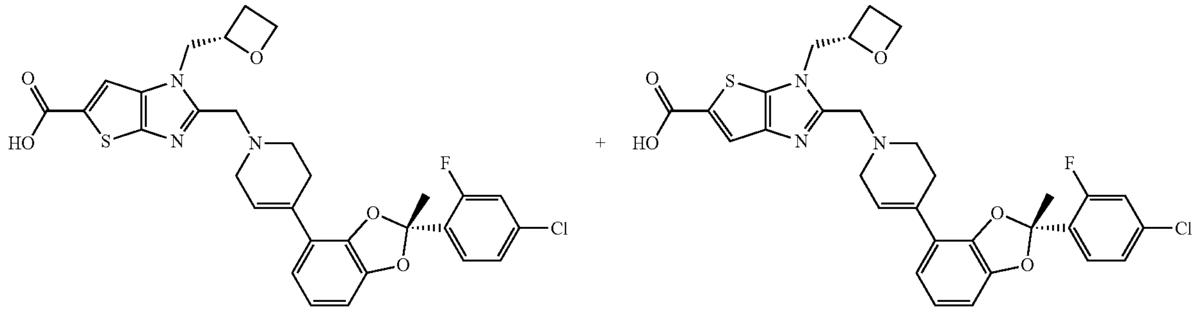
003A or 003B or 003C or 003D
003B or 003A or 003D or 003C
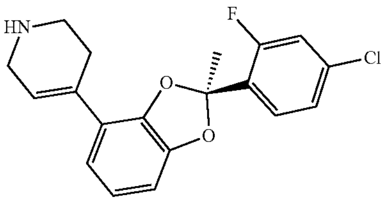
B-4 or B-3
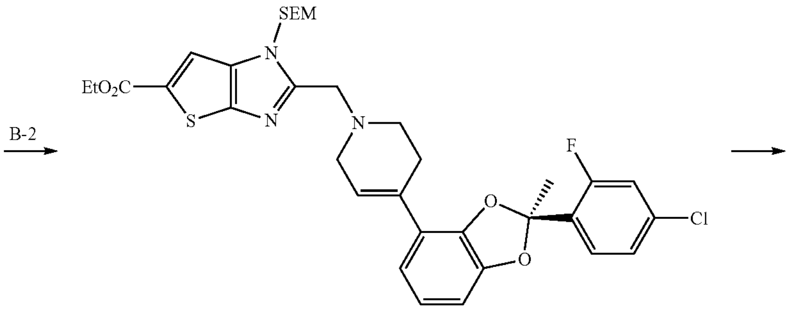
003B-1 or 003A-1
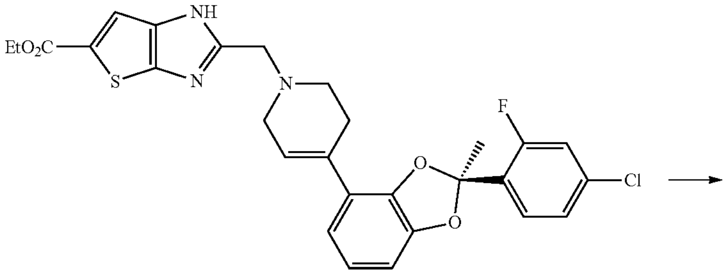
003B-2 or 003A-2
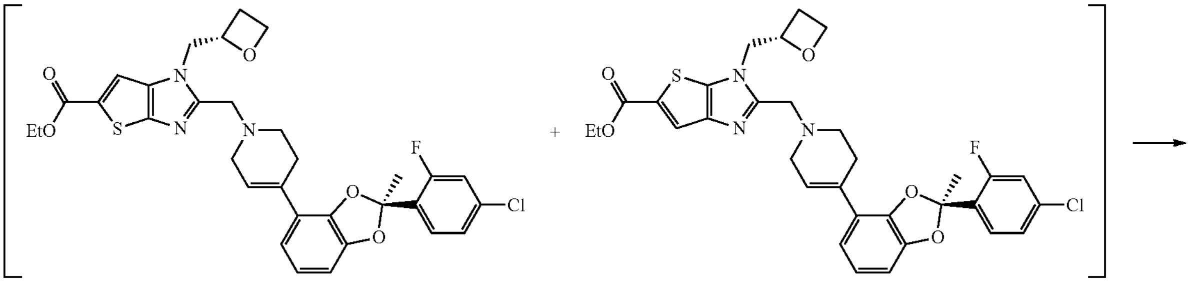
Mixture of 003C-3 or 003D-3 and 003A-3 or 003B-3

-continued

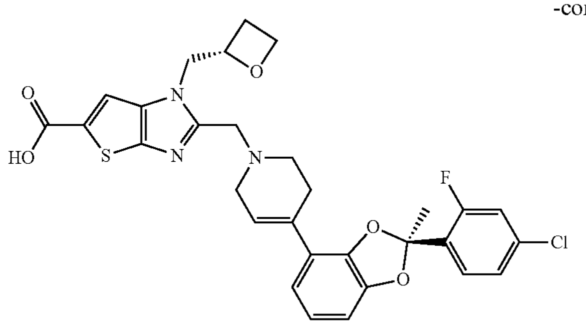

003C or 003D or 003A or 003B

+

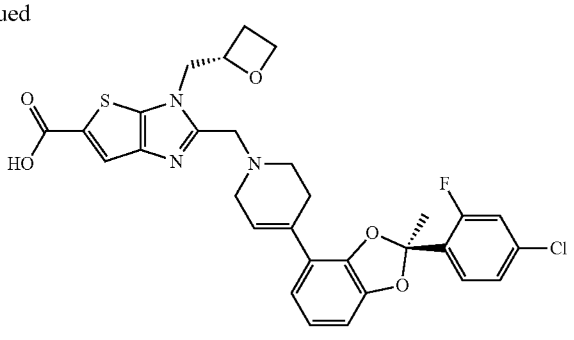

003D or 003C or 003B or 003A

Step 1: Synthesis of Compounds 003A-1 and 003B-1

Compound B-3 (130 mg, 346.71 μmol, 1 eq), compound B-2 (150 mg, 433.78 μmol, 1.25 eq), potassium carbonate (143.00 mg, 1.03 mmol, 2.98 eq) and acetonitrile (4 mL) were added to a reaction flask, heated to 50° C. and stirred for 16 hours. After the reaction was completed, the reaction solution was filtered, and the filter cake was washed with dichloromethane (10 mL*2), and then the filtrate was concentrated under reduced pressure to obtain a crude product. The crude product was purified and separated by preparative thin layer chromatography silica gel plate separation (PE:EA=3:1) to obtain compound 003A-1. LCMS: m/z=684.3 $[M+1]^+$.

Compound B-4 (140 mg, 373.38 μmol, 1 eq), compound B-2 (160 mg, 462.70 μmol, 1.24 eq), potassium carbonate (155 mg, 1.12 mmol, 3.00 eq) and acetonitrile (3 mL) were added to a reaction flask, heated to 50° C. and stirred for 3 hours. After the reaction was completed, the reaction solution was filtered, and the filter cake was washed with dichloromethane (10 mL*2), and the filtrate was concentrated under reduced pressure to obtain a crude product. The crude product was purified and separated by preparative thin layer chromatography silica gel plate separation (PE:EA=3:1) to obtain compound 003B-1. LCMS: m/z=684.3 $[M+1]^+$.

Step 2: Synthesis of Compounds 003A-2 and 003B-2

Compound 003A-1 (140 mg, 204.59 μmol, 1 eq), tetrabutylammonium fluoride (1 M, 1.02 mL, 5 eq) and tetrahydrofuran (4 mL) were added to a reaction flask, stirred at 50° C. for 24 hours. After the reaction was completed, the reaction solution was concentrated under reduced pressure to obtain a crude product. The crude product was purified and separated by preparative thin layer chromatography silica gel plate (EA:PE=10/90-60/40) to obtain compound 003A-2. LCMS: m/z=554.1 $[M+1]^+$.

Compound 003B-1 (180.00 mg, 263.05 μmoL 1 eq), tetrabutylammonium fluoride (1 M, 2.5 mL, 9.50 eq) and tetrahydrofuran (3 mL) were added to a reaction flask, stirred at 60° C. for 24 hours. After the reaction was completed, the reaction solution was concentrated under reduced pressure. The residue was added with water (10 mL), and then extracted with ethyl acetate (20 mL*3). The organic phases were combined and washed with saturated brine (10 mL), and concentrated under reduced pressure to obtain a crude product. The crude product was purified and separated by preparative thin layer chromatography silica gel plate (PE:EA=1:1) to obtain compound 003B-2. LCMS: m/z=554.3 $[M+1]^+$.

Step 3: Synthesis of Compounds 003A-3, 003B-3, 003C-3 and 003D-3

Compound 003A-2 (120 mg, 216.59 μmol, 1 eq), (S)-oxetan-2-yl methanesulfonate (108.00 mg, 649.84 μmol, 3 eq), cesium carbonate (211.71 mg, 649.78 μmol, 3 eq) and acetonitrile (1.5 mL) were added to a reaction flask, stirred at 80° C. for 16 hours. After the reaction was completed, the reaction solution was concentrated under reduced pressure. The residue was added with water (10 mL), and then extracted with ethyl acetate (10 mL*3). The organic phases were combined and concentrated under reduced pressure to obtain a crude product. The crude product was purified and separated by preparative thin layer chromatography silica gel plate (DCM:MeOH=20:1) to obtain a mixture of compounds 003A-3 and 003C-3. LCMS: m/z=624.1 $[M+1]^+$.

Compound 003B-2 (107.00 mg, 193.13 μmol, 1 eq), (S)-oxetan-2-yl methanesulfonate (96.30 mg, 579.39 μmol, 3 eq), cesium carbonate (188.78 mg, 579.39 μmol, 3 eq) and acetonitrile (2 mL) were added to a reaction flask, stirred at 80° C. for 11 hours. After the reaction was completed, the reaction solution was filtered, and the filter cake was washed with ethyl acetate (20 mL), then the filtrate and the washing solution were combined, and concentrated under reduced pressure to obtain a crude product. The crude product was purified and separated by preparative thin layer chromatography silica gel plate (DCM:MeOH=20:1) to obtain a mixture of compounds 003D-3A and 003B-3. LCMS: m/z=624.3 $[M+1]^+$.

Step 4: Synthesis of Compounds 003A, 003B, 003C and 003D

The mixture of compounds 003A-3 and 003C-3 (82 mg, 131.38 μmol, 1 eq), 1,5,7-triazabicyclo[4.4.0]dec-5-ene (37 mg, 265.81 μmol, 2.02 eq), acetonitrile (1 mL) and water (0.2 mL) were added to a reaction flask, stirred at 25° C. for 16 hours. After the reaction was completed, the pH was adjusted to about 6 by adding citric acid, and the mixture was concentrated under reduced pressure to obtain a crude product. The crude product was purified and separated by preparative thin layer chromatography silica gel plate (DCM:MeOH=10:1) to collect a crude product, and the crude product was purified and separated by preparative chiral separation (chromatographic column: DAICEL CHIRALPAK IG (250 mm*30 mm, 10 μm); mobile phase: phase A was $CO_2$, phase B was [0.1% $NH_3H_2O$-EtOH]; B %: 50%-50%) to obtain 003A (retention time: 2.282 min) and 003C (retention time: 2.818 min).

003A: LCMS: m/z=596.1 $[M+1]^+$; $^1H$ NMR (400 MHz, $CDCl_3$) δ ppm 2.05 (s, 3H), 2.38 (br s, 2H), 2.60-2.62 (m, 1H), 2.66 (br s, 1H), 3.05 (br s, 2H), 3.52 (br s, 2H), 4.02-4.19 (m, 2H), 4.35 (br s, 1H), 4.47-4.66 (m, 3H), 5.11 (br s, 1H), 6.42 (br s, 1H), 6.68-6.84 (m, 3H), 7.04-7.17 (m, 2H), 7.43-7.63 (m, 2H).

003C: LCMS: m/z=596.1 $[M+1]^+$; $^1H$ NMR (400 MHz, $CDCl_3$) δ ppm 2.04 (s, 3H), 2.43 (br s, 1H), 2.52-2.66 (m, 4H), 2.90 (br s, 1H), 3.36 (br s, 2H), 4.01 (br s, 2H), 4.43 (br d, J=16.31 Hz, 2H), 4.55 (br d, J=18.32 Hz, 2H), 5.18 (br s, 1H), 6.39 (br s, 1H), 6.65-6.83 (m, 3H), 7.02-7.18 (m, 2H), 7.48 (t, J=8.28 Hz, 1H), 7.82 (br s, 1H).

The mixture of compounds 003D-3 and 003B-3 (90 mg, 144.20 μmol, 1 eq), 1,5,7-triazabicyclo[4.4.0]dec-5-ene (40.61 mg, 291.74 μmol, 2.02 eq), acetonitrile (2 mL) and water (0.4 mL) were added to a reaction flask, stirred at 25° C. for 15 hours. After the reaction was completed, the pH was adjusted to about 6 by adding citric acid, and the mixture was concentrated under reduced pressure to obtain a crude product. The crude product was purified and separated by preparative thin layer chromatography silica gel plate (DCM:MeOH=20:1) to collect a crude product, and the crude product was purified and separated by preparative chiral separation (chromatographic column: DAICEL CHIRALPAK IG (250 mm*30 mm, 10 μm); mobile phase: phase A was $CO_2$; phase B was [0.1% $NH_3H_2O$-EtOH]; B %: 50%-50%) to obtain 003D (retention time: 2.236 min) and 003B (retention time: t=2.679 min).

003D: LCMS: m/z=596.1 $[M+1]^+$; $^1H$ NMR (400 MHz, $CDCl_3$) δ ppm 2.05 (s, 3H), 2.40 (br s, 1H), 2.65 (br s, 3H), 2.94 (br s, 2H), 3.41 (br s, 2H), 4.02 (br s, 2H), 4.34 (br s, 1H), 4.54 (br s, 3H), 5.13 (br s, 1H), 6.41 (br s, 1H), 6.70-6.82 (m, 3H), 7.05-7.16 (m, 2H), 7.44-7.54 (m, 1H), 7.63 (br s, 1H).

003B: LCMS: m/z=596.1 $[M+1]^+$; $^1H$ NMR (400 MHz, $CDCl_3$) δ ppm 2.05 (br s, 3H), 2.35-2.75 (m, 4H), 2.86 (br s, 2H), 3.32 (br s, 2H), 3.97 (br s, 2H), 4.27-4.74 (m, 4H), 5.20 (br s, 1H), 6.39 (br s, 1H), 6.69-6.86 (m, 3H), 7.04-7.17 (m, 2H), 7.49 (t, J=8.28 Hz, 1H), 7.85 (br s, 1H).

With reference to the synthetic steps of embodiment 4, the starting material in step 1 was replaced with B-7/B-8, and the following compounds 011A, 011B, 011C and 011D were synthesized.

| Embodiment 12 | Structure | Spectrogram |
|---|---|---|
| 011A | 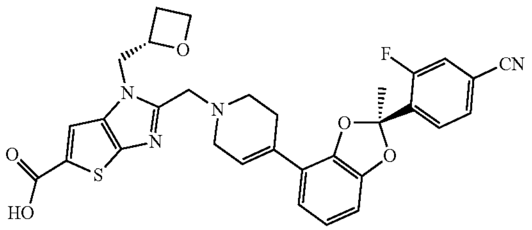 [SMILES: C[C@]1(c2ccc(C#N)cc2F)Oc2cccc(C3=CCN(Cc4nc5sc(C(=O)O)cc5n4C[C@@H]4CCO4)CC3)c2O1] | LCMS: m/z = 587.1 $[M + 1]^+$; $^1H$ NMR (400 MHz, $CDCl_3$) δ ppm 2.08 (s, 3 H) 2.34-2.48 (m, 1 H) 2.60-2.77 (m, 3 H) 3.04 (br d, J = 4.4 Hz, 2 H) 3.51 (br s, 2 H) 4.04-4.16 (m, 2 H) 4.32-4.43 (m, 1 H) 4.50-4.66 (m, 3 H) 5.14 (br s, 1 H) 6.42 (br s, 1 H) 6.73-6.84 (m, 3 H) 7.41 (t, J = 7.2 Hz, 2 H) 7.58 (s, 1 H) 7.66-7.73 (m, 1 H); the retention time was 2.145 min. |
| 011B | 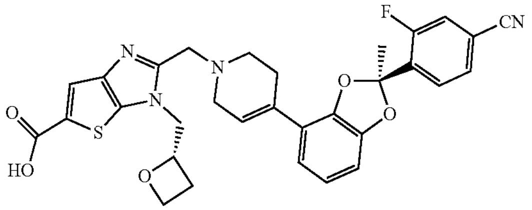 [SMILES: C[C@]1(c2ccc(C#N)cc2F)Oc2cccc(C3=CCN(Cc4nc5cc(C(=O)O)sc5n4C[C@@H]4CCO4)CC3)c2O1] | LCMS: m/z = 587.1 $[M + 1]^+$; $^1H$ NMR (400 MHz, $CDCl_3$) δ ppm 2.08 (s, 3 H) 2.40-2.79 (m, 4 H) 2.88 (br s, 2 H) 3.35 (br s, 2 H) 4.00 (s, 2 H) 4.38-4.70 (m, 4 H) 5.23 (br s, 1 H) 6.40 (br s, 1 H) 6.72-6.85 (m, 3 H) 7.36-7.47 (m, 2 H) 7.70 (t, J = 7.6 Hz, 1 H) 7.86 (s, 1 H); the retention time was 4.335 min. |
| 011C | 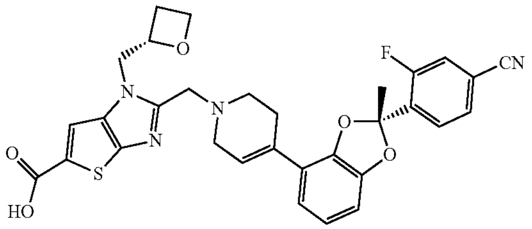 [SMILES: C[C@@]1(c2ccc(C#N)cc2F)Oc2cccc(C3=CCN(Cc4nc5sc(C(=O)O)cc5n4C[C@@H]4CCO4)CC3)c2O1] | LCMS: m/z = 587.1 $[M + 1]^+$; $^1H$ NMR (400 MHz, $CDCl_3$) δ ppm 2.07 (s, 3 H) 2.31-2.45 (m, 1 H) 2.59-2.74 (m, 3 H) 3.09 (br s, 2 H) 3.56 (br s, 2 H) 4.08-4.22 (m, 2 H) 4.29-4.42 (m, 1 H) 4.47-4.69 (m, 3 H) 5.12 (br s, 1 H) 6.41 (br s, 1 H) 6.70-6.85 (m, 3 H) 7.33-7.45 (m, 2 H) 7.51 (s, 1 H) 7.69 (t, J = 8.0 Hz, 1 H); the retention time was 0.754 min. |
| 011D | 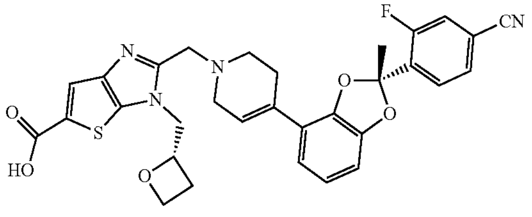 [SMILES: C[C@@]1(c2ccc(C#N)cc2F)Oc2cccc(C3=CCN(Cc4nc5cc(C(=O)O)sc5n4C[C@@H]4CCO4)CC3)c2O1] | LCMS: m/z = 587.1 $[M + 1]^+$; $^1H$ NMR (400 MHz, $CDCl_3$) δ ppm 2.08 (s, 3 H) 2.40-2.77 (m, 4 H) 2.88 (br s, 2H) 3.35 (br s, 2 H) 4.00 (br s, 2 H) 4.38-4.69 (m, 4 H) 5.22 (br s, 1 H) 6.40 (br s, 1 H) 6.70-6.86 (m, 3 H) 7.41 (br t, J = 8.0 Hz, 2 H) 7.70 (br t, J = 7.2 Hz, 1 H) 7.86 (br s, 1 H); the retention time was 1.304 min. |

Embodiment 5

004

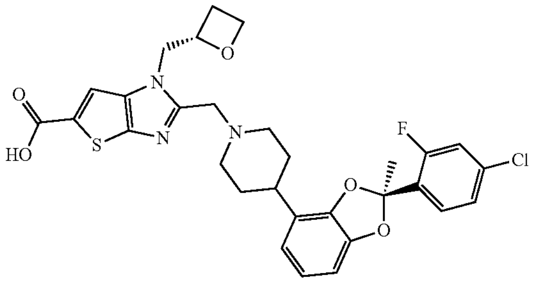

or

-continued

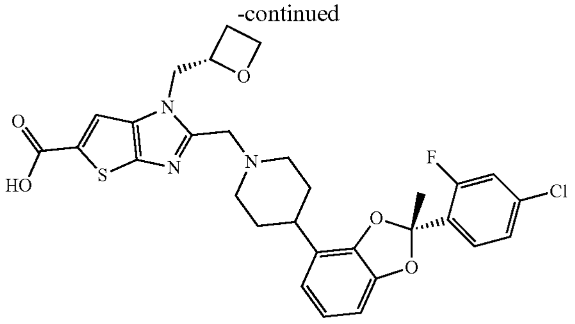

Synthetic Route:

B-3

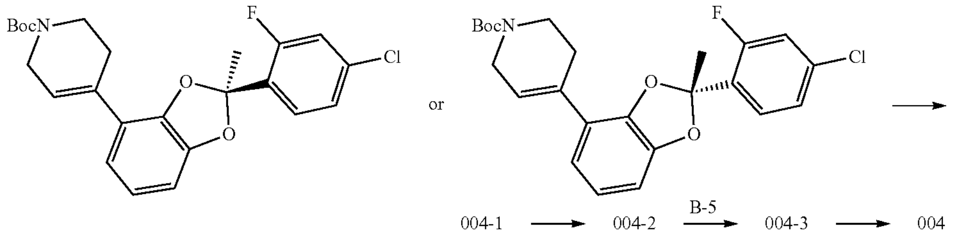

Step 1: Synthesis of Compound 004-1

004-1

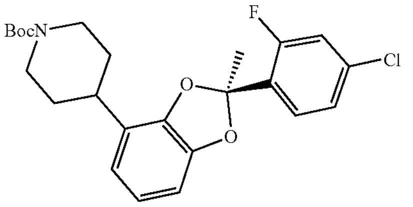

or

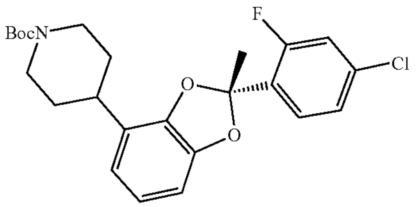

Under the protection of nitrogen, wet palladium carbon (0.2 g, purity of 10%) was added to a solution of B-3 (retention time: 2.474 min) (2 g, 4.49 mmol, 1 eq) in ethyl acetate (40 mL), and reacted at 25° C. for 18 hours under hydrogen atmosphere (15 psi). The reaction solution was filtered, and the filter cake was washed with ethyl acetate (5 mL*3), and then the filtrate was combined and evaporated to dryness by rotary evaporation to obtain a crude product. The crude product was purified and separated by column chromatography (EA/PE=0-5%) to obtain compound 004-1. LCMS: m/z=392.2 [M-55]$^+$.

Step 2: Synthesis of Compound 004-2

004-2

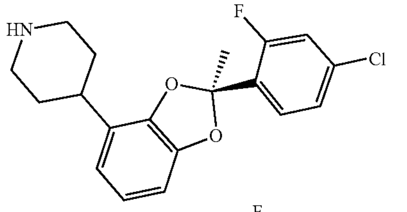

or

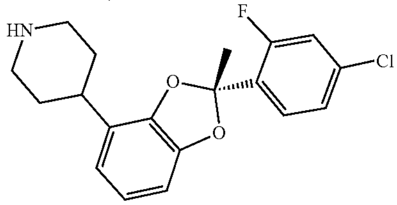

004-1 (0.5 g, 1.12 mmol, 1 eq) was dissolved in ethyl acetate (10 mL), and then added with p-toluenesulfonic acid monohydrate (0.25 g, 1.31 mmol, 1.18 eq), protected by nitrogen, and reacted at 50° C. for 18 hours. Saturated sodium bicarbonate aqueous solution (25 mL) was added to the reaction solution, stirred for 2 minutes. The phases were separated, and the organic phase was washed with water (25 mL) and saturated brine (25 mL) respectively, dried with anhydrous sodium sulfate, filtered, and evaporated to dryness by rotary evaporation to obtain compound 004-2. LCMS: m/z=347.9 $[M+1]^+$.

Step 3: Synthesis of Compound 004-3

004-3

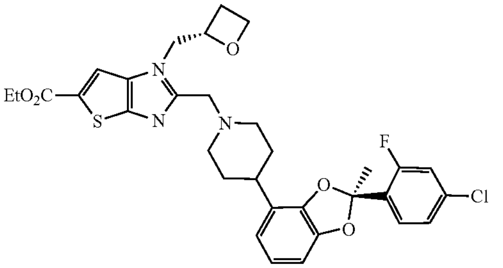

or

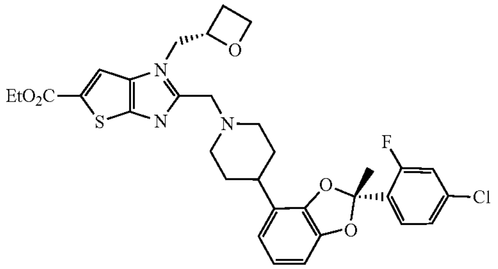

004-2 (80 mg, 230.01 μmol, 1.19 eq) and B-5 (61 mg, 193.78 μmol, 1 eq) were dissolved in acetonitrile (2 mL), and then added with potassium carbonate (80 mg, 578.85 μmol, 2.99 eq), protected by nitrogen atmosphere, and reacted at 50° C. for 16 hours. The reaction solution was filtered, and the filtrate was concentrated to obtain a crude product. The crude product was purified by preparative thin layer chromatography silica gel plate (DCM:MeOH=20:1) to obtain compound 004-3. LCMS, m/z=626.2 $[M+1]^+$.

Step 4: Synthesis of Compound 004

004

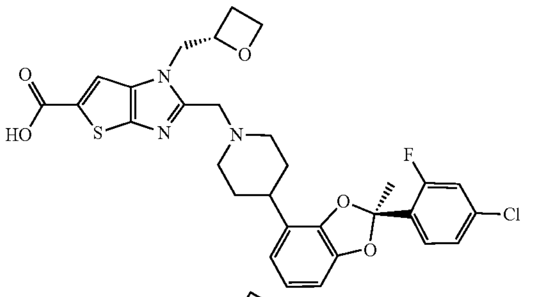

or

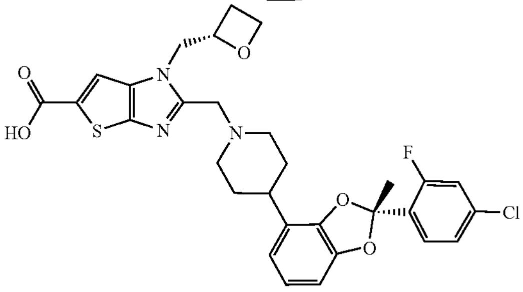

004-3 (40 mg, 63.88 μmol, 1 eq) was dissolved in a mixture of tetrahydrofuran (0.25 mL), methanol (0.25 mL) and water (0.5 mL), and added with lithium hydroxide (7.65 mg, 319.42 μmol, 5 eq), protected by nitrogen atmosphere, and reacted at 25° C. for 1 hour. The pH was adjusted to about 6 by adding citric acid to the reaction solution, and the mixture was concentrated to obtain a crude product. The crude product was separated by preparative high performance liquid chromatography (chromatographic column: Phenomenex Gemini-NX 80*40 mm*3 m; mobile phase: [water (0.05% ammonia water)-acetonitrile]; B (acetonitrile) %: 21%-51%, 8 min) to obtain 004. LCMS, m/z=598.1 $[M+1]^+$; $^1H$ NMR (400 MHz, DMSO-$d_6$) δ ppm 7.55 (t, J=8.4 Hz, 1H), 7.45-7.51 (m, 2H), 7.30 (br d, J=7.0 Hz, 1H), 6.73-6.78 (m, 2H), 6.67-6.73 (m, 1H), 5.08 (br d, J=3.5 Hz, 1H), 4.52-4.59 (m, 1H), 4.43-4.50 (m, 2H), 4.32-4.39 (m, 1H), 3.73-3.79 (m, 1H), 3.67 (br d, J=13.6 Hz, 1H), 2.97 (br d, J=10.5 Hz, 1H), 2.87 (br d, J=10.5 Hz, 1H), 2.58-2.71 (m, 2H), 2.43 (br d, J=8.8 Hz, 1H), 2.13 (br d, J=11.5 Hz, 2H), 2.01 (s, 3H), 1.65-1.78 (m, 4H).

Embodiment 6

005A

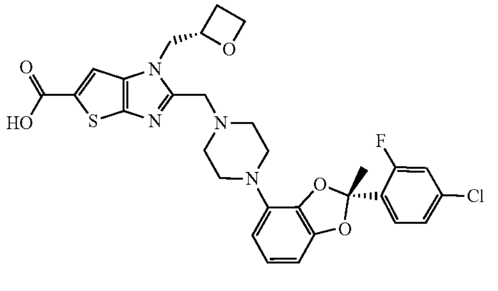

or

-continued
005B
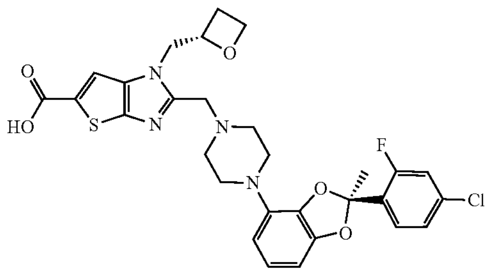
Synthetic Route:
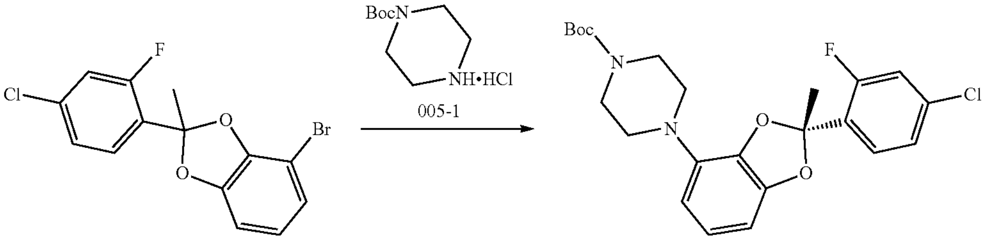
001-3
005A-2 or 005B-2
+
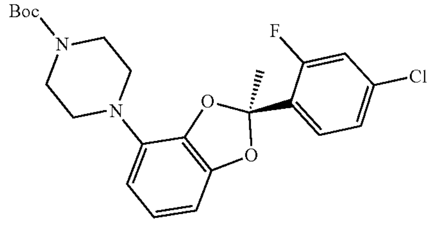
005B-2 or 005A-2
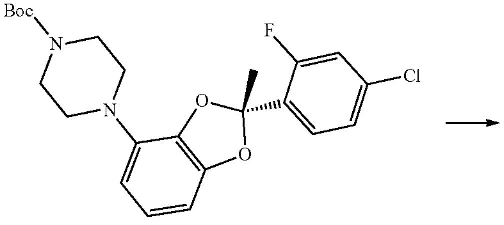
005A-2 or 005B-2
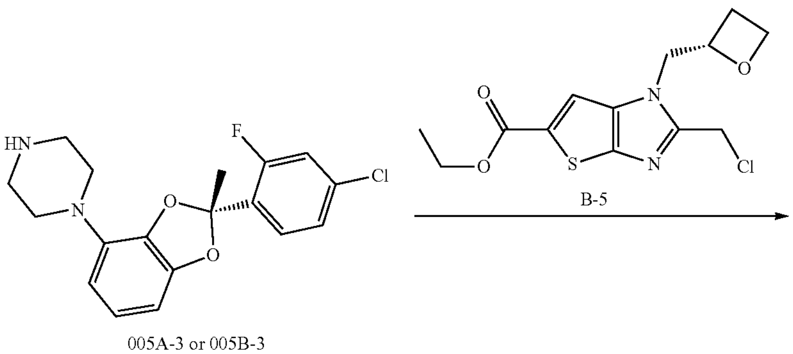
005A-3 or 005B-3

-continued
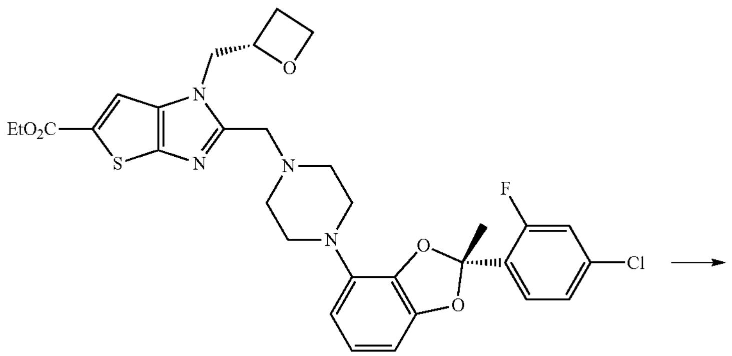
005A-4 or 005B-4
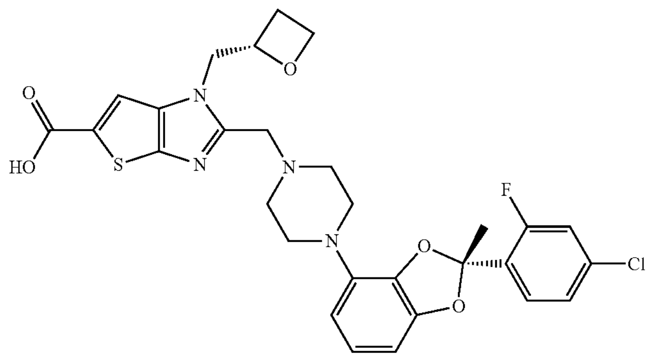
005A or 005B
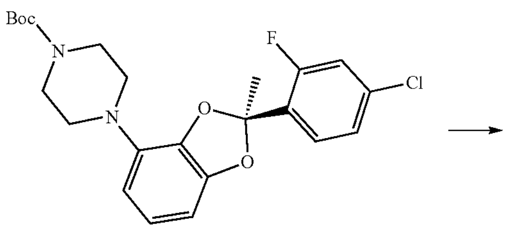
005B-2 or 005A-2
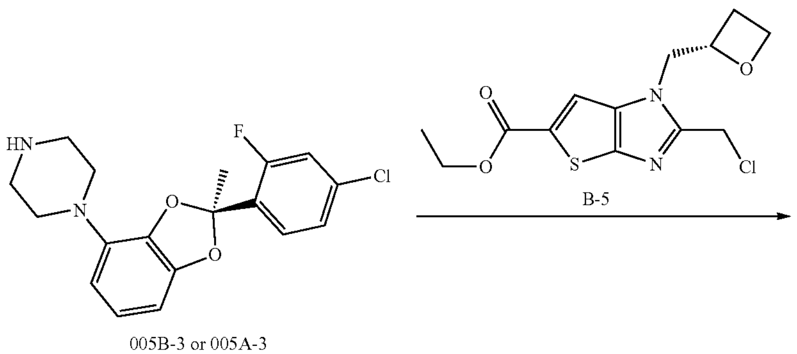
005B-3 or 005A-3

-continued

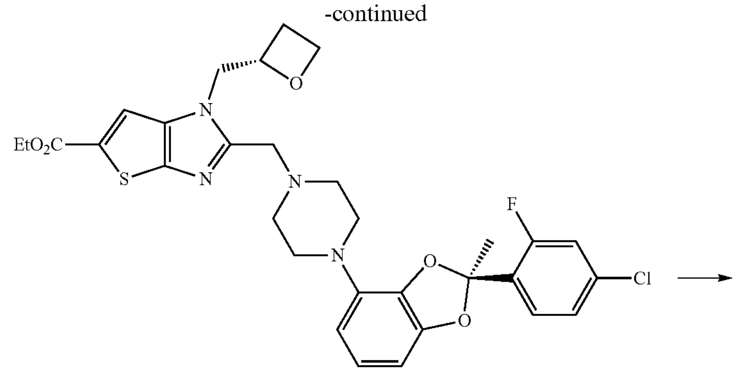

005B-4 or 005A-4

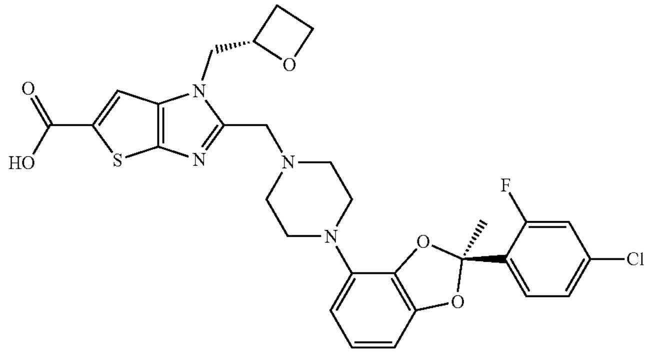

005B or 005A

Step 1: Synthesis of Compounds 005A-2 and 005B-2

001-3 (0.61 g, 1.78 mmol, 1 eq), 005-1 (436.51 mg, 1.96 mmol, 1.1 eq), cesium carbonate (852.18 mg, 2.62 mmol, 1.47 eq), 2,2-bis(diphenylphosphino)-1,1-binaphthyl (83.21 mg, 133.64 μmol, 7.51e$^{-2}$ eq) and palladium acetate (20.05 mg, 89.31 μmol, 0.05 eq) were suspended in toluene (20 mL), protected by nitrogen atmosphere, reacted at 100° C. for 16 hours. The solvent was evaporated to dryness by rotary evaporation, then dichloromethane (40 mL) was added to fully dissolve the residue, and the mixture was filtered, and the filtrate was evaporated to dryness by rotary evaporation to obtain a crude product. The crude product was separated by column chromatography (PE:EA=20:1) to obtain a racemate. The racemate was separated and purified by supercritical fluid chromatography (DAICEL CHIRALPAK AD (250 mm*30 mm, 10 μm): mobile phase: phase A was $CO_2$, phase B was [0.1% ammonia water-ethanol]; B %: 15%-15%) to obtain 005A-2 (retention time: 2.836 min), LCMS: m/z=449.0 $[M+1]^+$; and 005B-2 (retention time: 2.664 min), LCMS: m/z=449.0 $[M+1]^+$.

Step 2: Synthesis of Compounds 005A-3 and 005B-3

005A-2 (210.00 mg, 467.80 μmol, 1 eq) was added to ethyl acetate (5 mL), and added with p-toluenesulfonic acid monohydrate (0.1 g, 525.72 μmol, 1.12 eq), protected by nitrogen atmosphere, reacted at 50° C. for 18 hours. The reaction solution was washed with saturated sodium carbonate aqueous solution (5 mL), water (10 mL) and saturated brine (10 mL) respectively. The organic phase was dried with anhydrous sodium sulfate, filtered, and evaporated to dryness by rotary evaporation to obtain compound 005A-3. LCMS: m/z=348.9 $[M+1]^+$.

005B-2 (180.00 mg, 400.97 μmol, 1 eq) was dissolved in ethyl acetate (5 mL), and added with p-toluenesulfonic acid monohydrate (0.1 g, 525.72 μmol, 1.31 eq), protected by nitrogen atmosphere, reacted at 50° C. for 34 hours. The reaction solution was washed with saturated sodium carbonate aqueous solution (5 mL), water (10 mL) and saturated brine (10 mL) respectively. The organic phase was dried with anhydrous sodium sulfate, filtered, and evaporated to dryness by rotary evaporation to obtain compound 005B-3. LCMS: m/z=348.9 $[M+1]^+$.

Step 3: Synthesis of Compounds 005A-4 and 005B-4

005A-3 (150.00 mg, 430.05 μmol, 1.2 eq), B-5 (0.11 g, 349.41 μmol, 0.98 eq) and potassium carbonate (0.15 g, 1.09 mmol, 3.03 eq) were suspended in acetonitrile (4 mL), protected by nitrogen atmosphere, and reacted at 50° C. for 16 hours. The reaction solution was filtered, and the filtrate was evaporated to dryness by rotary evaporation to obtain a crude product. The crude product was separated by column chromatography (DCM:MeOH=20:1) to obtain compound 005A-4. LCMS: m/z=627.1 $[M+1]^+$.

005B-3 (100 mg, 286.70 μmol, 1.2 eq), B-5 (75 mg, 238.20 μmol, 1.00 eq) and potassium carbonate (0.1 g, 723.56 μmol, 3.03 eq) were suspended in acetonitrile (3 mL), protected by nitrogen, and reacted at 50° C. for 16 hours. The reaction solution was filtered, and the filtrate was evaporated to dryness by rotary evaporation to obtain a crude product. The crude product was separated by column chromatography (DCM:MeOH=40:1) to obtain compound 005B-4. LCMS: m/z=627.0 $[M+1]^+$.

Step 4: Synthesis of Compounds 005A and 005B 005A-4 (0.18 g, 287.02 μmol, 1 eq) was dissolved in tetrahydrofuran (2 mL), and then lithium hydroxide monohydrate (60.00 mg, 1.43 mmol, 4.98 eq), water (1 mL) and methanol (1 mL) were added thereto, and the mixture was stirred at 25° C. for 1 hour. The pH was adjusted to about 6 by adding citric acid to the reaction solution, and the mixture was concentrated to obtain a crude product. The crude product was separated by preparative high performance liquid chromatography (chromatographic column: Phenomenex Gemini-NX 80*40 mm*3 m: mobile phase: [water (0.05% ammonia water)—acetonitrile]; B (acetonitrile) %:

23%-53%, 8 min) to obtain compound 005A. ee %=97.08%; LCMS: m/z=599.1 $[M+1]^+$; $^1H$ NMR (400 MHz, DMSO-$d_6$) δ ppm 7.51-7.58 (m, 2H), 7.33 (dd, J=8.5, 2.0 Hz, 1H), 7.22 (s, 1H), 6.72-6.78 (m, 1H), 6.54 (d, J=7.8 Hz, 1H), 6.43 (d, J=8.3 Hz, 1H), 5.00-5.09 (m, 1H), 4.40-4.55 (m, 3H), 4.33-4.40 (m, 1H), 3.78 (d, J=13.3 Hz, 1H), 3.65 (d, J=13.3 Hz, 1H), 3.15 (br s, 2H), 3.05 (br s, 2H), 2.63-2.70 (m, 1H), 2.54 (br s, 4H), 2.34-2.43 (m, 1H), 2.01 (s, 3H).

005B-4 (0.12 g, 191.35 μmol, 1 eq) was dissolved in tetrahydrofuran (2 mL), and then lithium hydroxide monohydrate (40.00 mg, 953.21 μmol, 4.98 eq), water (1 mL) and methanol (1 mL) were added thereto, and the mixture was stirred at 25° C. for 1 hour. The pH was adjusted to about 6 by adding citric acid to the reaction solution, and the mixture was concentrated to obtain a crude product. The crude product was separated by preparative high performance liquid chromatography (chromatographic column: Phenomenex Gemini-NX 80*40 mm*3 μm: mobile phase: [water (0.05% ammonia water)—acetonitrile]; B (acetonitrile) %: 23%-53%, 8 min) to obtain compound 005B. ee %=100%; LCMS: m/z=599.1 $[M+1]^+$; $^1H$ NMR (400 MHz, DMSO-$d_6$) δ ppm 7.51-7.58 (m, 2H), 7.33 (dd, J=8.5, 1.8 Hz, 1H), 7.28 (s, 1H), 6.71-6.78 (m, 1H), 6.54 (d, J=7.5 Hz, 1H), 6.43 (d, J=8.3 Hz, 1H), 5.02-5.09 (m, 1H), 4.40-4.55 (m, 3H), 4.34 (dt, J=9.1, 6.0 Hz, 1H), 3.69-3.77 (m, 2H), 3.13 (br s, 2H), 3.04 (br d, J=11.0 Hz, 2H), 2.62-2.70 (m, 1H), 2.55 (br s, 4H), 2.35-2.43 (m, 1H), 2.00 (s, 3H).

Embodiment 7

006

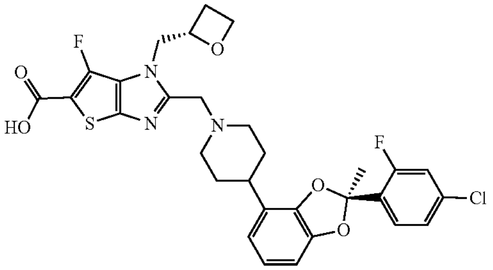

or

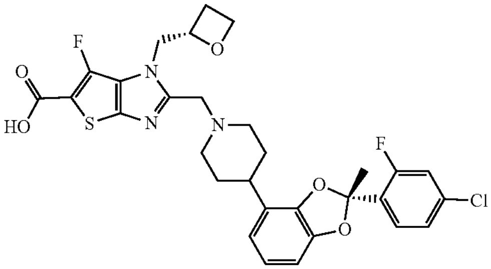

Synthetic Route:

004-2

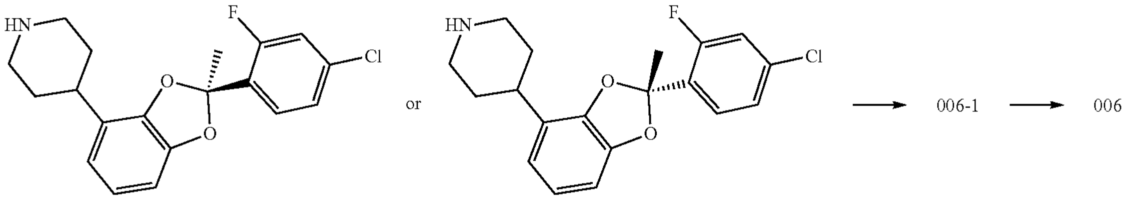

Step 1: Synthesis of Compound 006-1

006-1

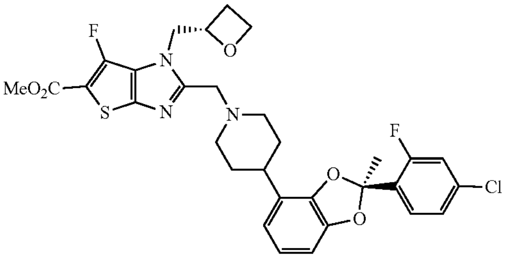

or

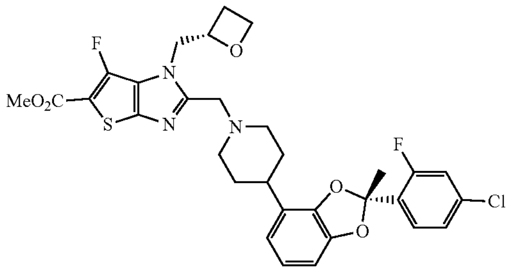

004-2 (60.00 mg, 172.51 μmol, 1.10 eq) and B-6 (50 mg, 156.86 μmol, 1 eq) were dissolved in acetonitrile (2 mL), and added with potassium carbonate (64.29 mg, 465.13 μmol, 2.97 eq), protected by nitrogen atmosphere, reacted at 50° C. for 16 hours. The reaction solution was filtered and the filtrate was concentrated to obtain a crude product. The crude product was purified by column chromatography (DCM:MeOH=10:1) to obtain compound 006-1. LCMS: m/z=630.0 $[M+1]^+$ Step 2: Synthesis of Compound 006

006

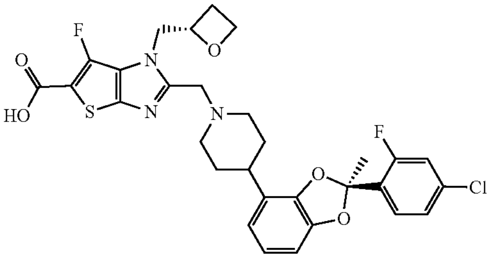

or

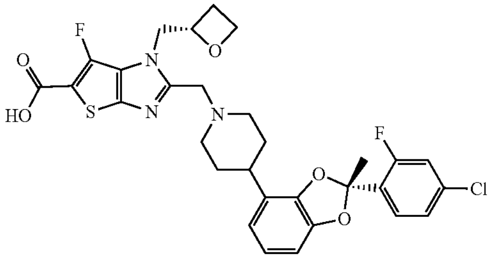

006-1 (50 mg, 79.35 μmol, 1 eq) was dissolved in a mixture of tetrahydrofuran (1 mL), methanol (0.5 mL) and water (0.5 mL), and added with lithium hydroxide (9.50 mg, 396.76 mol, 5 eq), protected by nitrogen atmosphere, reacted at 25° C. for 1 hour. The pH was adjusted to about 6 by adding citric acid to the reaction solution, and the mixture was concentrated to obtain a crude product. The crude product was separated by preparative high performance liquid chromatography (chromatographic column: Phenomenex Gemini-NX 80*40 mm*3 m: mobile phase: [water (0.05% ammonia water)—acetonitrile]; B (acetonitrile) %: 24%-54%, 8 min) to obtain compound 006. LCMS, m/z=616.0 $[M+1]^+$; $^1$H NMR (400 MHz, DMSO-$d_6$) δ ppm 7.53-7.59 (m, 2H), 7.34 (dd, J=8.4, 1.9 Hz, 1H), 6.79 (d, J=4.3 Hz, 2H), 6.71-6.76 (m, 1H), 5.02-5.10 (m, 1H), 4.45-4.63 (m, 3H), 4.39 (dt, J=9.0, 6.1 Hz, 1H), 3.82 (br d, J=13.6 Hz, 1H), 3.69 (br d, J=13.6 Hz, 1H), 2.98 (br d, J=11.0 Hz, 1H), 2.88 (br d, J=11.3 Hz, 1H), 2.58-2.76 (m, 2H), 2.39-2.46 (m, 1H), 2.09-2.23 (m, 2H), 2.02 (s, 3H), 1.66-1.79 (m, 4H).

Embodiment 8

007

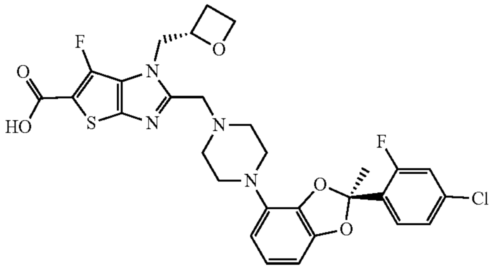

or

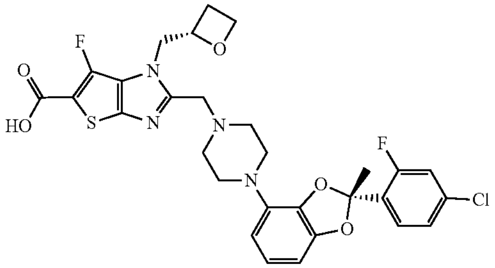

Synthetic Route:

005-3

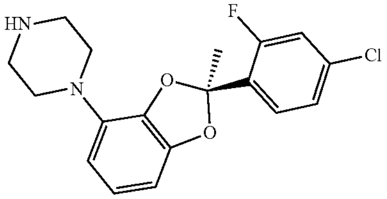

or

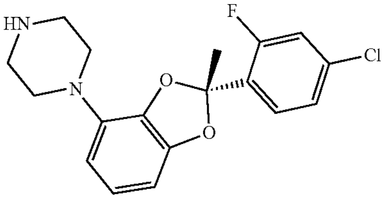

007-1

007

Step 1: Synthesis of Compound 007-1
007-1
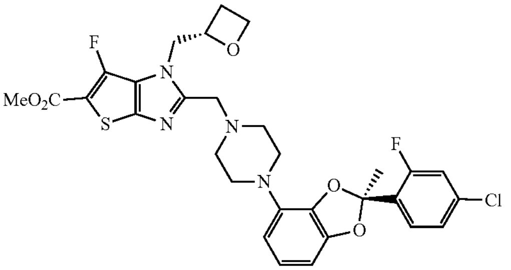
or
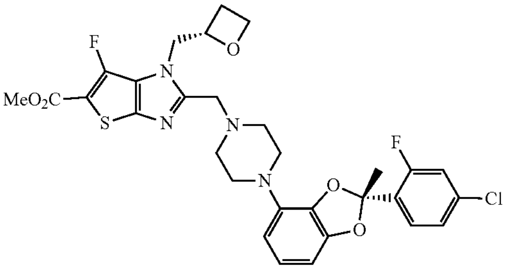
Step 2: Synthesis of Compound 007
007
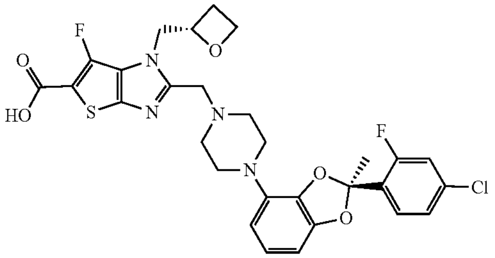
or
-continued
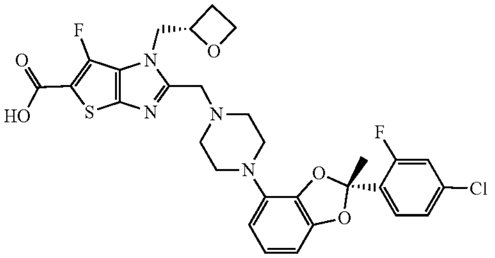
Embodiment 9
008
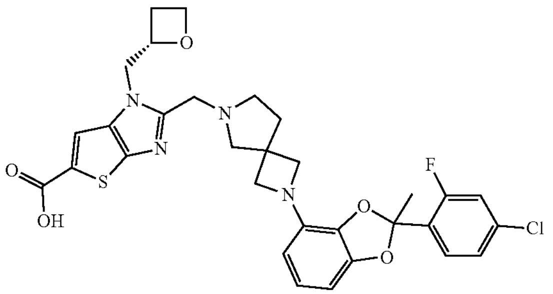
Synthetic Route:
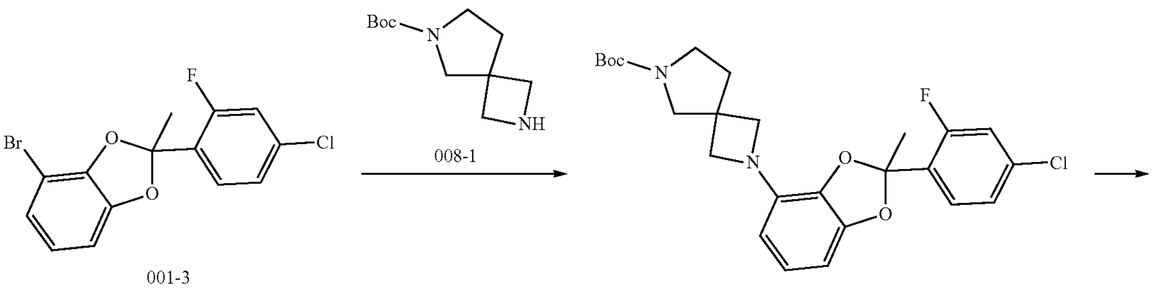
001-3
008-2

-continued

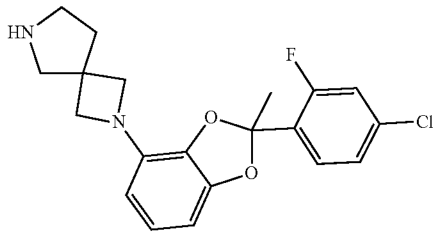

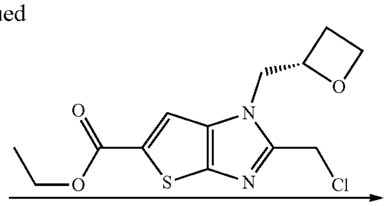

B-5

008-3

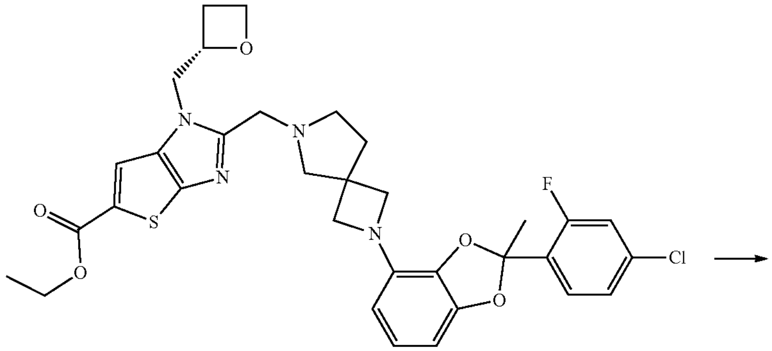

008-4

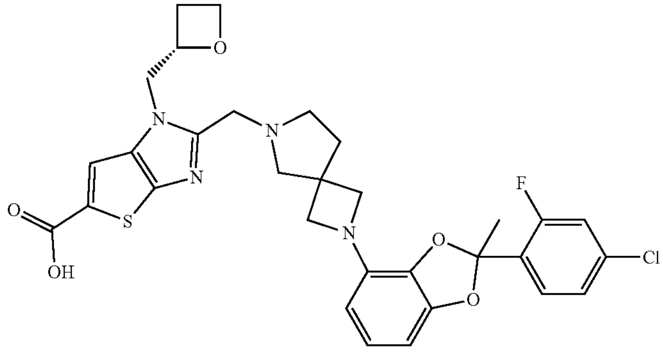

008

Step 1: Synthesis of Compound 008-2

001-3 (140.00 mg, 407.48 μmol, 1 eq), 008-1 (98.61 mg, 464.53 μmol, 1.14 eq), toluene (3 mL) and cesium carbonate (195.16 mg, 599.00 μmol, 1.47 eq) were added to a dry reaction flask in turn, and the system was replaced with nitrogen atmosphere, then palladium acetate (4.57 mg, 20.37 μmol, 0.05 eq) and 2,2'-bis(diphenylphosphino)-1,1'-binaphthyl (17.76 mg, 28.52 μmol, 0.07 eq) were added thereto, and then the system was replaced with nitrogen again. The temperature was raised to 100° C., and the mixture was stirred for 10 hours. The mixture was diluted with water (20 mL), extracted with ethyl acetate (20 mL*3). After the phases were separated, the organic phases were collected, washed with saturated brine solution (20 mL*3) in turn, dried with anhydrous sodium sulfate, and concentrated under reduced pressure. The residue was purified by thin layer chromatography silica gel plate (DCM:MeOH=20:1) to obtain compound 008-2. $^1$H NMR (400 MHz, $CDCl_3$) δ ppm 7.52 (t, J=8.3 Hz, 1H), 7.17-7.09 (m, 2H), 6.72 (t, J=8.0 Hz, 1H), 6.39 (br d, J=7.9 Hz, 1H), 6.04 (br d, J=7.8 Hz, 1H), 3.97-3.81 (m, 4H), 3.53 (s, 2H), 3.47-3.35 (m, 2H), 2.20-2.08 (m, 2H), 2.04 (s, 3H), 1.48 (s, 9H).

Step 2: Synthesis of Compound 008-3

008-2 (100.00 mg, 210.55 μmol, 1 eq), dichloromethane (1 mL) and trifluoroacetic acid (0.1 mL) were added to a dry reaction flask, stirred at 20° C. for 1 hour. Sodium bicarbonate aqueous solution (20 mL) was added for neutralization, and ethyl acetate (20 mL*3) was added for extraction. After the phases were separated, the organic phases were collected, washed with saturated brine solution (20 mL*3) in turn, dried with anhydrous sodium sulfate, and concentrated under reduced pressure to obtain compound 008-3. LCMS: m/z=375.0 $[M+1]^+$.

Step 3: Synthesis of Compound 008-4

008-3 (92.38 mg, 293.46 μmol, 1 eq), acetonitrile (3 mL) and potassium carbonate (60.84 mg, 440.19 μmol, 1.5 eq) were added to a dry reaction flask, stirred at 60° C. for 10 hours. Water (10 mL) was added for dilution, and ethyl acetate (10 mL*3) was added for extraction. After the phases were separated, the organic phases were collected, washed with saturated brine solution (10 mL*3) in turn, dried with anhydrous sodium sulfate, and concentrated under reduced pressure. The residue was purified by thin layer chromatography silica gel plate (DCM:MeOH=20:1) to obtain compound 008-4. LCMS: m/z=653.3 $[M+1]^+$.

Step 4: Synthesis of Compound 008

008-4 (10 mg, 15.31 μmol, 1 eq), water (0.5 mL), methanol (0.5 mL), tetrahydrofuran (0.5 mL) and lithium hydroxide monohydrate (1.93 mg, 45.93 μmol, 3 eq) were added to a dry reaction flask, stirred at 20° C. for 1 hour. The reaction solution was directly concentrated under reduced pressure. The residue was separated by high performance liquid chromatography (chromatographic column: Phenomenex C18 75*30 mm*3 m; mobile phase: [water (ammonia water+ammonium bicarbonate) acetonitrile]; B (acetonitrile) %: 30%-60%, 8 min) to obtain compound 008. LCMS: m/z=625.1 $[M+1]^+$; $^1H$ NMR (400 MHz, $CD_3OD$) δ 7.68 (s, 1H), 7.56 (t, J=8.3 Hz, 1H), 7.29-7.23 (m, 1H), 7.19 (dd, J=1.5, 8.5 Hz, 1H), 6.69 (t, J=8.0 Hz, 1H), 6.35 (d, J=7.8 Hz, 1H), 6.07 (d, J=8.1 Hz, 1H), 5.17 (dq, J=2.6, 7.0 Hz, 1H), 4.68-4.60 (m, 2H), 4.55 (d, J=2.6 Hz, 1H), 4.45-4.38 (m, 1H), 4.27-4.14 (m, 2H), 3.95-3.92 (m, 1H), 3.88 (s, 2H), 3.82 (d, J=7.4 Hz, 1H), 3.23-3.15 (m, 2H), 3.02-2.96 (m, 2H), 2.83-2.72 (m, 1H), 2.51-2.43 (m, 1H), 2.23 (t, J=7.1 Hz, 2H), 1.99 (s, 3H).

Embodiment 10

009

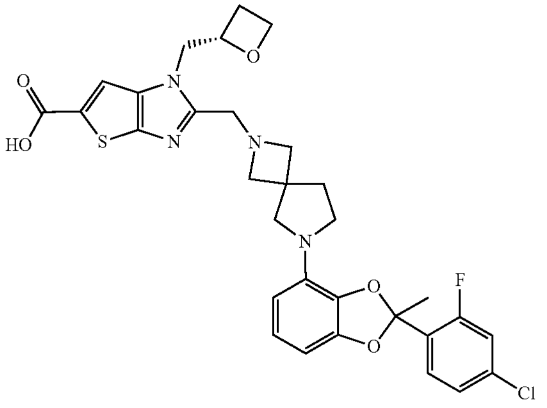

Synthetic Route:

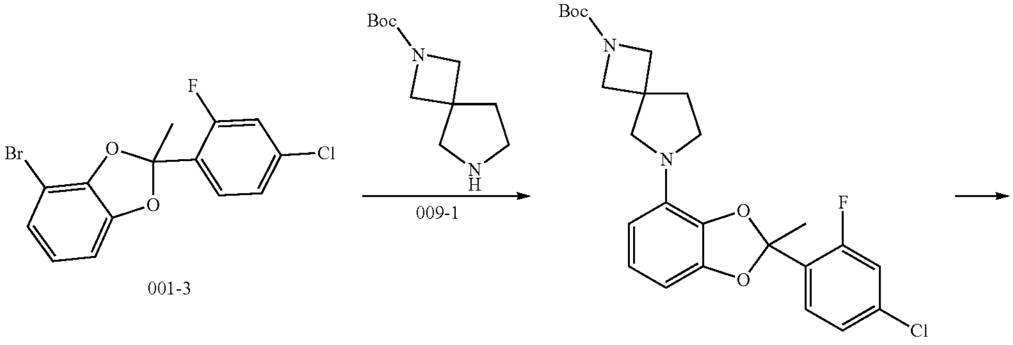

001-3

009-2

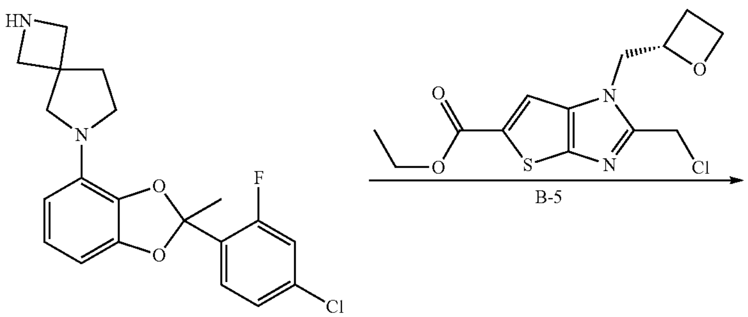

009-3

-continued

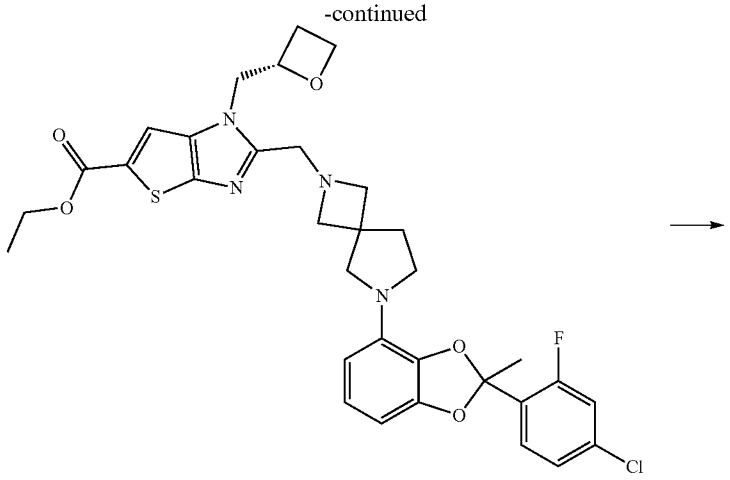

009-4

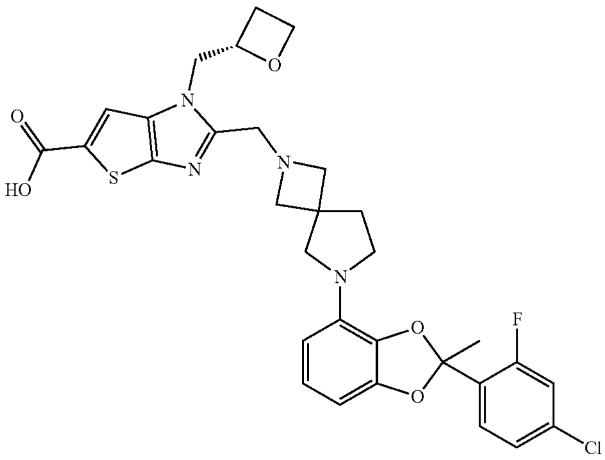

009

Step 1: Synthesis of Compound 009-2

001-3 (300 mg, 873.17 μmol, 1.0 eq), 009-1 (203.90 mg, 960.49 μmol, 1.1 eq), 2,2'-bis(diphenylphosphino)-1,1'-binaphthyl (38.06 mg, 61.12 μmol, 0.07 eq), palladium acetate (9.80 mg, 43.66 μmoL, 0.05 eq) and cesium carbonate (426.74 mg, 1.31 mmol, 1.5 eq) were added to toluene (10 mL), and reacted for 12 hours at 100° C. under the protection of nitrogen atmosphere. The reaction solution was added with water (20 mL) and ethyl acetate (20 mL*3). After the phases were separated, the organic phases were collected, washed with saturated brine solution (20 mL*3) in turn, dried with anhydrous sodium sulfate, and concentrated under reduced pressure to obtain a crude product. The crude product was purified by thin layer chromatography silica gel plate (DCM:MeOH=20:1) to obtain compound 009-2. LCMS: m/z=475.1 $[M+1]^+$.

Step 2: Synthesis of Compound 009-3

009-2 (230 mg, 484.26 μmol, 1 eq) was dissolved in dichloromethane (5 mL), added with trifluoroacetic acid (924.00 mg, 8.10 mmol, 0.6 mL, 16.73 eq), protected by nitrogen atmosphere, reacted for 0.5 hours at 25° C. The reaction solution was directly evaporated to dryness by rotary evaporation to obtain compound 009-3. LCMS: m/z=375.1 $[M+1]^+$.

Step 3: Synthesis of Compound 009-4

009-3 (170 mg, 453.53 μmol, 1 eq) and B-5 (142.77 mg, 453.53 μmol, 1 eq) were dissolved in acetonitrile (4 mL), added with potassium carbonate (94.02 mg, 680.30 μmol, 1.5 eq) and reacted at 60° C. for 4 hours. The reaction solution was poured into saturated ammonium chloride (20 mL) aqueous solution, and ethyl acetate (20 mL*3) was added for extraction. The organic phases were combined, washed with saturated brine solution (20 mL*2) in turn, dried with anhydrous sodium sulfate, and evaporated to dryness by rotary evaporation under reduced pressure to obtain compound 009-4. LCMS: m/z=653.3 $[M+1]^+$.

Step 4: Synthesis of Compound 009

009-4 (230 mg, 352.13 μmol, 1 eq), tetrahydrofuran (2 mL), methanol (2 mL) and lithium hydroxide monohydrate (44.33 mg, 1.06 mmol, 3 eq) were added to a dry reaction flask, stirred at 20° C. for 2 hours. The reaction solution was directly concentrated under reduced pressure to obtain a crude product. The crude product was separated and purified by high performance liquid chromatography separation (chromatographic column: Phenomenex C18 75*30 mm*3 m; mobile phase: [water (ammonia water+ammonium bicarbonate) acetonitrile]; B (acetonitrile) %: 30%-60%) to obtain 009. LCMS: m/z=625.2 $[M+1]^+$; $^1H$ NMR (400 MHz, $CD_3OD$) δ 7.58-7.48 (m, 1H), 7.27-7.23 (m, 1H), 7.17-7.06 (m, 2H), 6.80-6.63 (m, 1H), 6.35 (d, J=7.5 Hz, 1H), 6.13 (br d, J=8.0 Hz, 1H), 5.10-4.96 (m, 1H), 4.61-4.53 (m, 2H), 4.50-4.40 (m, 2H), 4.38-4.29 (m, 2H), 4.04 (br s, 4H), 3.72-3.63 (m, 2H), 3.54-3.47 (m, 1H), 3.45-3.39 (m, 1H), 2.72-2.55 (m, 1H), 2.36-2.17 (m, 3H), 2.03 (s, 3H).

Embodiment 11
010A
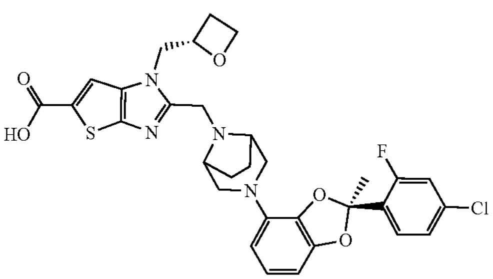
-continued
010B
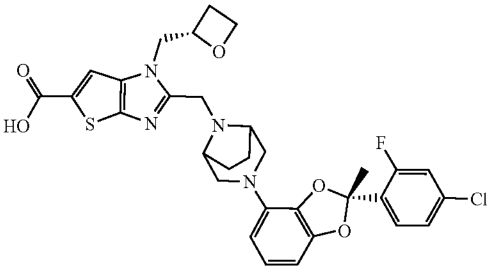
Synthetic Route:
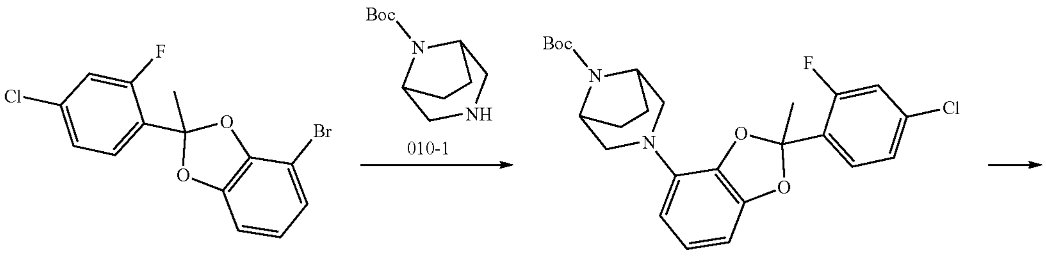
001-3 010-1 010-2
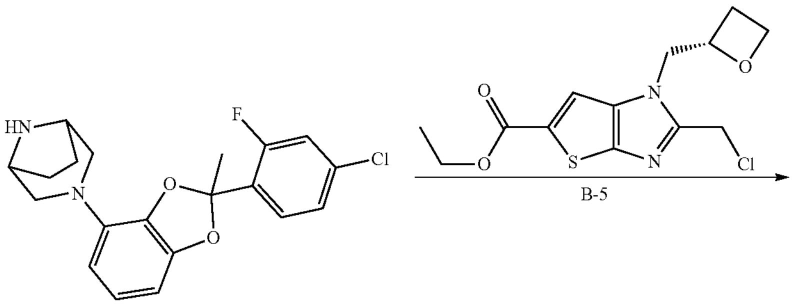
010-3 B-5
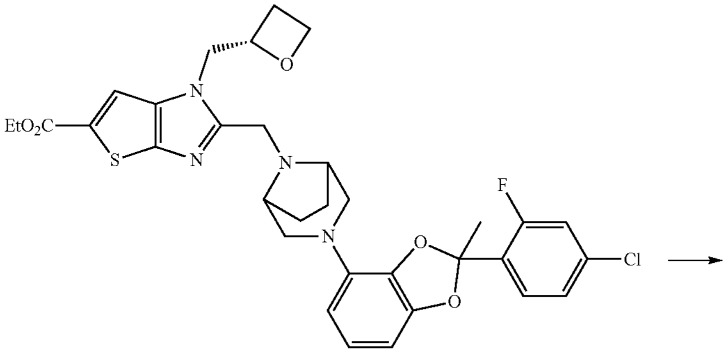
010-4

-continued

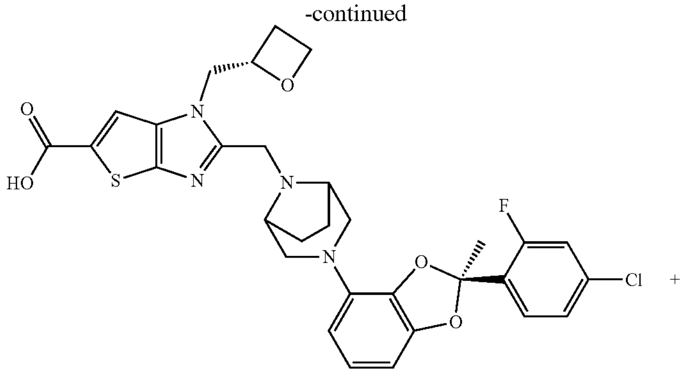

+

010A or 010B

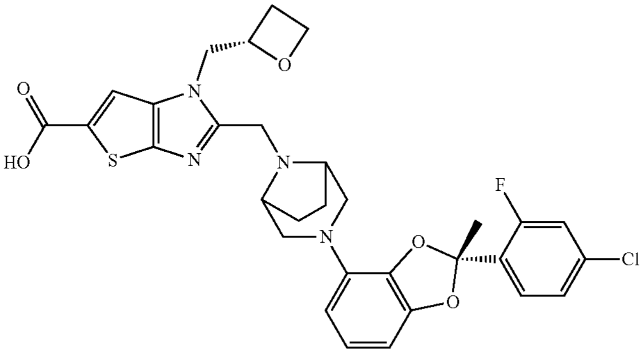

010B or 010A

Step 1: Synthesis of Compound 010-2

001-3 (0.20 g, 582.11 μmol, 1.00 eq), 010-1 (135.93 mg, 640.33 μmol, 1.10 eq), 2,2-bis(diphenylphosphino)-1,1-binaphthyl (18.12 mg, 29.11 μmol, 0.05 eq), palladium acetate (6.53 mg, 29.11 μmol, 0.05 eq) and cesium carbonate (284.50 mg, 873.17 mmol, 1.50 eq) were suspended in toluene (4 mL) and reacted for 4 hours at 100° C. under the protection of nitrogen. The reaction solution was added with water (5 mL) and ethyl acetate (5 mL) for extraction, and the organic phase was concentrated under reduced pressure to obtain a crude product. The crude product was separated by column chromatography (PE:EA=3:1) to obtain 010-2. LCMS: m/z=475.1 $[M+1]^+$.

Step 2: Synthesis of Compound 010-3

010-2 (90.00 mg, 189.49 μmol, 1.00 eq) was added to ethyl acetate (3.6 mL), and added with p-toluenesulfonic acid monohydrate (39.65 mg, 208.44 μmol, 1.10 eq), reacted at 60° C. for 6 hours. Water and ethyl acetate (2 mL) were added thereto, and the mixture was stirred for 5 min, then the pH was adjusted to 8 by adding sodium bicarbonate solid, and the mixture was stood for phase separation. The aqueous phase was extracted once with ethyl acetate (2 mL). The organic phases were combined, and dried with anhydrous sodium sulfate, filtered, and concentrated to obtain 010-3. LCMS: m/z=375.0 $[M+1]^+$.

Step 3: Synthesis of Compound 010-4

B-5 (60.00 mg, 110.49 μmol, 1.00 eq), 010-3 (38.26 mg, 121.54 μmol, 1.10 eq) and potassium carbonate (45.81 mg, 331.46 μmol, 3.00 eq) were suspended in acetonitrile (1.5 mL), reacted at 50° C. for 5 hours. The mixture was filtered, and the filtrate was concentrated to obtain compound 010-4. LCMS: m/z=653.3 $[M+1]^+$.

Step 4: Synthesis of Compounds 010A and 010B 010-4 (0.10 g, 153.10 μmol, 1.00 eq) was dissolved in a mixture of tetrahydrofuran (0.5 mL), methanol (0.5 mL) and water (0.5 mL), and added with lithium hydroxide (18.33 mg, 765.50 μmol, 5.00 eq), reacted at 20° C. for 24 hours. The pH was adjusted to about 5 by adding citric acid, and the mixture was concentrated to obtain a crude product. The crude product was separated by preparative high performance liquid chromatography (chromatographic column: Waters Xbridge Prep OBD C18 150*40 mm*10 m: mobile phase: [water (0.05% ammonia water+10 mM ammonium bicarbonate)—acetonitrile]; B (acetonitrile) %: 10%-65%, 8 min) to obtain a racemate. The racemate was separated and purified by prep-SFC (chromatographic column: DAICEL CHIRALPAK IG (250 mm*30 mm, m); mobile phase: phase A was supercritical $CO_2$, phase B was [0.1% ammonia water-methanol]; B %: 45%-45%, 10 min) to obtain 010A (retention time: 1.307 min), ee %=99.42%; 010B (retention time: 1.657 min), ee %=93.36%.

010A: LCMS: m/z=625.1 $[M+1]^+$; $^1H$ NMR (400 MHz, DMSO-$d_6$) δ ppm 7.8 (br s, 1H), 7.5-7.6 (m, 2H), 7.3-7.4 (m, 1H), 6.7-6.8 (m, 1H), 6.5 (d, J=7.8 Hz, 1H), 6.3 (d, J=8.5 Hz, 1H), 5.2 (br d, J=4.3 Hz, 1H), 4.7-4.7 (m, 1H), 4.6-4.7 (m, 1H), 4.5-4.5 (m, 1H), 4.4 (dt, J=8.9, 6.0 Hz, 1H), 3.7-3.8 (m, 2H), 3.4 (br d, J=10.4 Hz, 2H), 2.7-2.9 (m, 2H), 2.3-2.4 (m, 2H), 2.0 (m, 5H), 1.8 (br d, J=8.4 Hz, 2H), 1.1-1.3 (m, 2H)

010B: LCMS: m/z=625.1 $[M+1]^+$; $^1H$ NMR (400 MHz, DMSO-$d_6$) δ ppm 7.7 (br s, 1H), 7.5-7.6 (m, 2H), 7.3 (dd, J=8.4, 1.9 Hz, 1H), 6.7-6.7 (m, 1H), 6.5 (d, J=7.8 Hz, 1H), 6.3 (d, J=8.4 Hz, 1H), 5.1-5.2 (m, 1H), 4.7-4.8 (m, 1H), 4.5-4.6 (m, 1H), 4.4-4.5 (m, 1H), 4.4 (dt, J=8.9, 6.1 Hz, 1H), 3.7-3.8 (m, 2H), 3.4 (br d, J=10.9 Hz, 2H), 2.7-2.9 (m, 2H), 2.3-2.4 (m, 2H), 2.0 (s, 5H), 1.8 (br d, J=7.5 Hz, 2H), 1.1-1.3 (m, 2H).

Experimental Embodiment 1

Binding simulation of compounds 3-6 to GLP-1 receptor:

Compound 3

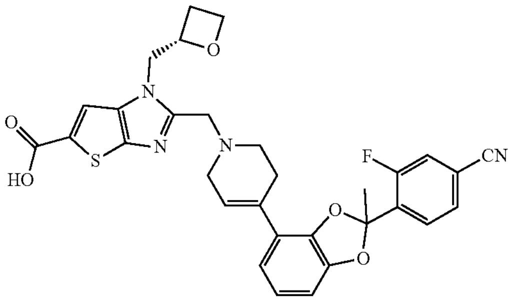

Compound 4

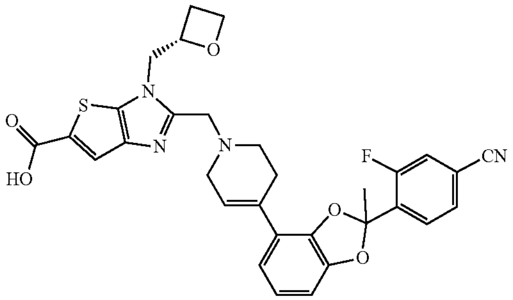

Compound 5

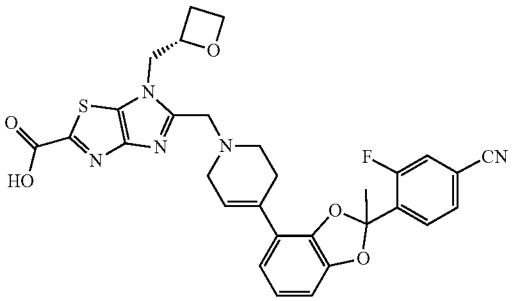

Compound 6

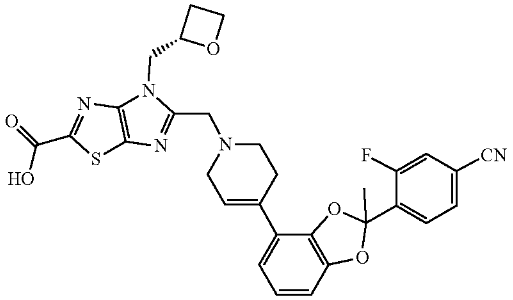

The molecular docking process was carried out by using the Glide SP [1] and a default option in Maestro (Schrödinger version 2017-2). A co-crystal structure of GLP-1R (PDBID code: 5NX2) was selected as a docking template. To prepare proteins, a hydrogen atom was added using a protein preparation guide module of Maestro [2], and an OPLS3 force field was used. For the preparation of ligands, LigPrep was used to generate the three-dimensional structure of the molecule, and the energy minimization [3] was performed. Using a ligand in a 5NX2 crystal structure as a center of mass, a cubic docking grid with a side length of 30 Å was generated. The ligand was then removed and the embodiment compound was placed during molecular docking process. The interaction type between protein receptor and ligand was analyzed, and then the reasonable docking conformation was selected and saved according to the calculated binding mode and docking score. The binding mode of compound 3-compound 6 to GLP-1 receptor is shown in FIG. 4 to FIG. 7 of the drawings.

[1] Glide, Schrödinger, LLC, New York, NY, 2017.
[2] Maestro, Schrödinger, LLC, New York, NY, 2017.
[3] LigPrep, Schrödinger, LLC, New York, NY, 2017.

Figure 2:
FIG. 2 is binding site between agonist and GLP-1 receptor.

GLP-1 receptor three-dimensional structure (FIG. 1 GLP-1-GLP-1r complex);

GLP-1 binding site of the agonist (FIG. 2 Polypeptide agonist-GLP-1r complex); the protein has a larger flexibility.

Figure 3:
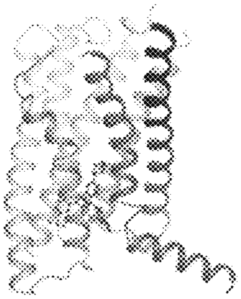
FIG. 3 is binding site between antagonist and GLP-1 receptor.
Figure 4:
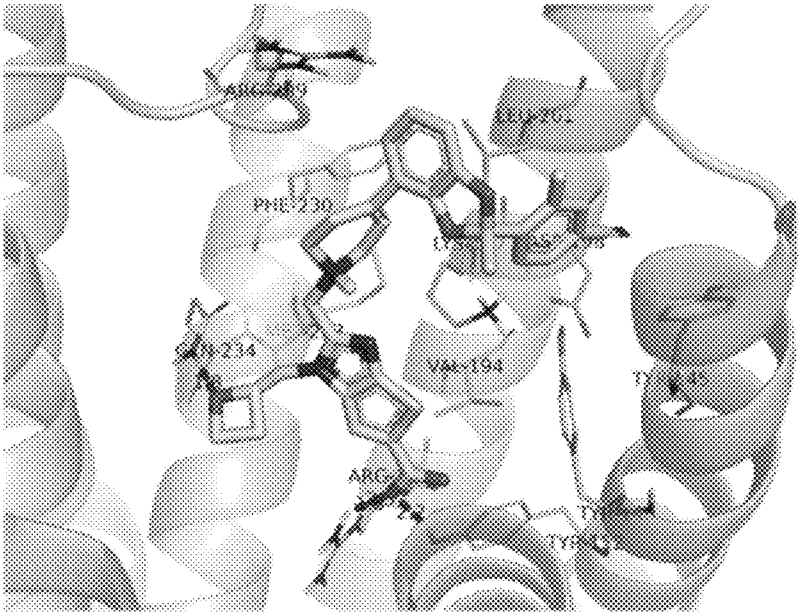
FIG. 4 is prediction of the binding mode of compound 3.
Figure 5:
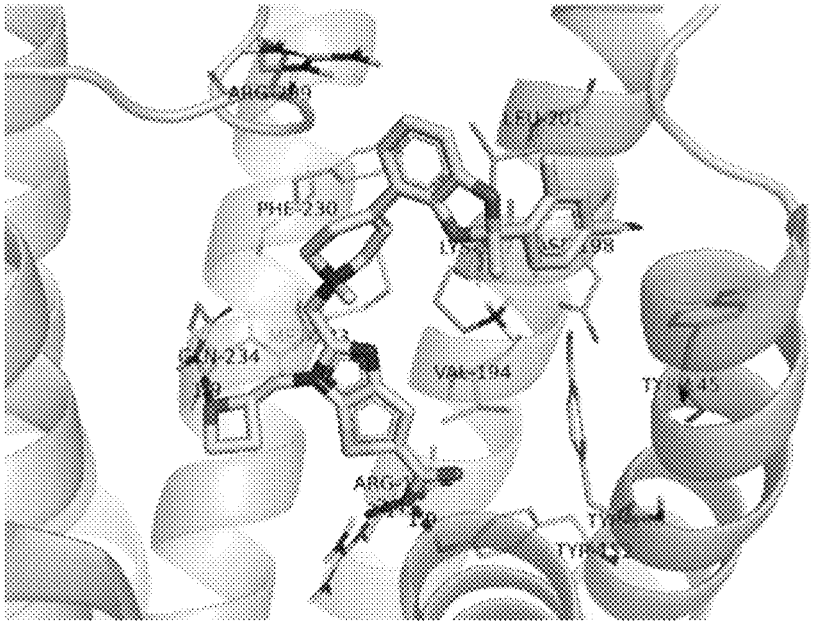
FIG. 5 is prediction of the binding mode of compound 4.
Figure 6:
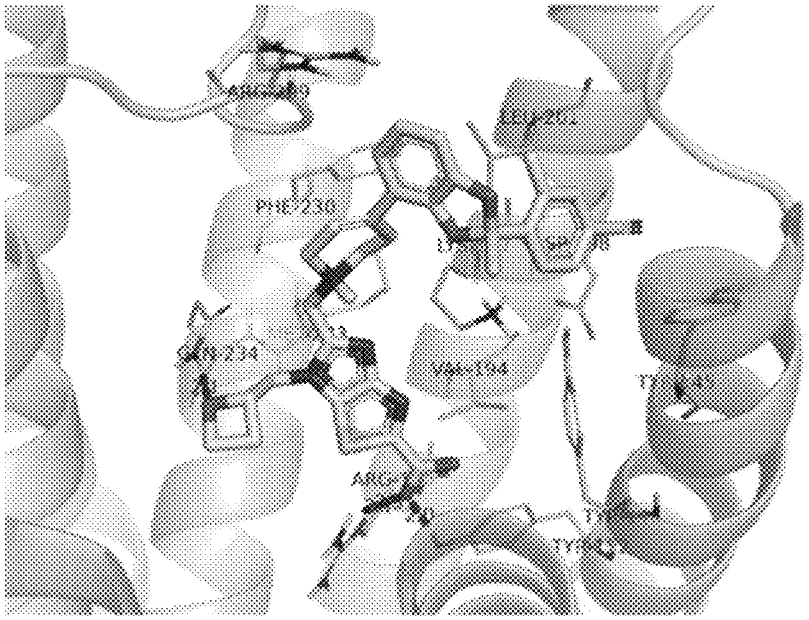
FIG. 6 is prediction of the binding mode of compound 5.
Figure 7:
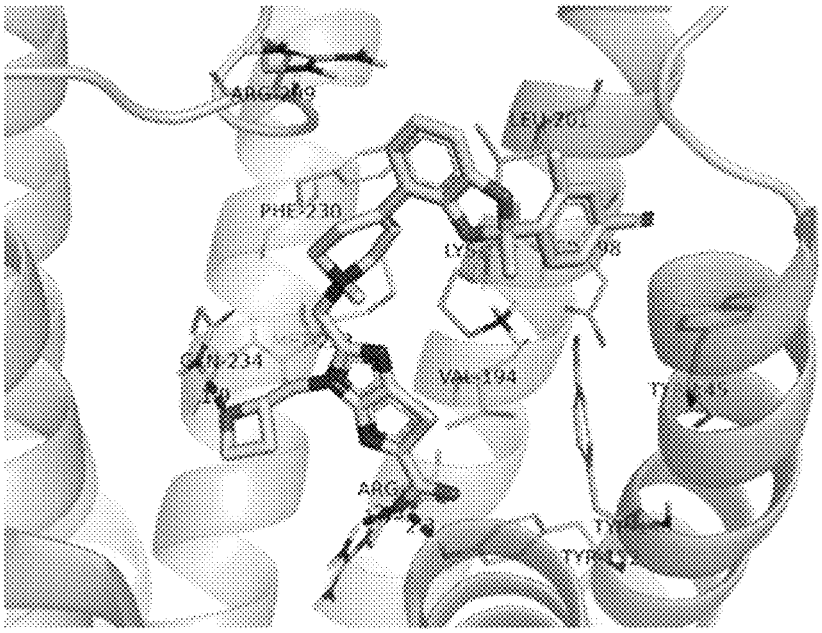
FIG. 7 is prediction of the binding mode of compound 6.

Antagonist binds to the extracellular regions of the 5th, 6th and 7th helical protein surfaces (FIG. 3 Antagonist binds to the 5th, 6th and 7th helical protein surfaces).

Experimental Embodiment 2: Cell Activity Test In Vitro

1. Material

1) Cell Line

The cells were constructed by Wuxi New Drug Development Co., Ltd. Shanghai. Details are shown in the following table.

| Target | Host cell |
|---|---|
| GLP-1 | HEK293 |

2) Reagent

| |
|---|
| cAMP Detection Kit, Cisbio (Cat # 62AM4PEJ) |
| 1M HEPES, Invitrogen (Cat # 15630-106) |
| 1X HBSS, Invitrogen (Cat # 14025) |
| BSA, Sigma (Cat # B2064) |
| IBMX, Sigma (Cat # I5879) |
| Exenatide, Hao Yuan (HY-13443A) |

3) Equipment

OptiPlate-384, White, PerkinElmer (Cat #6007290); 384 well plate for Echo, Labcyte (Cat #P-05525); EnVision, PerkinElmer; Vi-cell counter, Beckman (Cat #Vi-CELL™ XR Cell Viability Analyzer)

4) Compound Information

The compound was formulated with DMSO to a working concentration of 30 μM. In this test, the usage amount of each sample was 5 μL.

2. Method

1) Experimental Material

Experimental Buffer

| Volume | Final concentration |
|---|---|
| 24.5 mL of Hanks Buffer Saline Solution (HBSS) | 1x |
| 125 μL of HEPES 1M | 5 mM |
| 333 μL of 7.5% BSA Solution | 0.1% |
| 25 μL of IBMX 500 mmol/L | 0.5 mmol/L |

The pH was adjusted to 7.4 and the volume was fixed to 25 mL with HBSS 1×.

Preparation of Detection Reagent

Preparation of cAMP detection reagent: 250 μL of cAMP-D2 and 250 μL of anti-cAMP cryptate reagent were added to 4 mL of lysis buffer, and mixed gently.

2) Experimental Method a) Preparation of Compound Plates:

The test compound was diluted 3 times by 10 points with a starting concentration of 30 μM, and the dilutions were completed by Bravo.

The reference compound exenatide was diluted 3 times by 10 points with a starting concentration of 500 nM, and the dilutions were completed by Bravo.

b) Transfer of Compounds:

1) 100 nL of compound was transferred to OptiPlate-384 plate using Echo.
2) OptiPlate-384 plate was centrifuged at 1000 rpm for 5 seconds.

c) Preparation of cell suspension

1) A GLP-1 cell cryopreservation tube was quickly thawed in 37° C. warm water.
2) The cell suspension was transferred to a Transfer 15 mL of centrifuge tube and gently rinsed with 10 mL of HBSS.
3) The centrifuge tube was centrifuged at 1000 rpm at room temperature for 1 minute.
4) The supernatant was discarded.
5) The cells at the bottom were gently dispersed and gently rinsed with 10 mL of HBSS, then the cells were centrifuged for sedimentation, and finally the cells were re-suspended in experimental buffer.
6) Cell density and activity were measured by using Vi-cell.
7) The concentration of GLP-1 cells was diluted to $2.0*10^5$/mL with the experimental buffer.
8) 100 nL of diluted cell suspension was transferred into OptiPlate-384 plate.
9) The cells were incubated at room temperature for 30 minutes.

d) Addition of detection reagents:

1) 10 μL of 800 nM gradient diluted cAMP standard was added to the empty well of OptiPlate-384 plate.
2) 10 μL of cAMP detection reagent was added.
3) OptiPlate-384 plate was covered with TopSeal-A film and incubated for 60 min at room temperature.

The TopSeal-A was removed, and the EnVision reading was performed.

The experimental results are shown in Table 1:

TABLE 1

In vitro cell activity test results

| Compound | Human-GLP 1, $EC_{50}$ (nM) |
|---|---|
| 003A | 1.16 |
| 003C | 8.63 |

TABLE 1-continued

In vitro cell activity test results

| Compound | Human-GLP 1, $EC_{50}$ (nM) |
|---|---|
| 004 | 0.20 |
| 005A | 0.15 |
| 006 | 0.39 |
| 011A | 0.33 |
| 0011B | 1.52 |

Conclusion: The compound of the present disclosure shows a better agonistic ability to GLP-1 receptor.

Experimental Embodiment 3: Cytochrome P450 Isoenzyme Inhibitory Research Test 1. Test Purpose To test the inhibitory effects of the test compounds on the activities of human liver microsomal cytochrome P450 isoenzymes (CYP1A2, CYP2C9, CYP2C19, CYP2D6 and CYP3A4).

2. Experimental Method

Firstly, the test compound (10.0 mM) was diluted in gradient to prepare a working solution (100× final concentration), and the working solution concentrations were 5.00, 1.50, 0.500, 0.150, 0.0500, 0.0150 and 0.00500 mM respectively. At the same time, the working solution of each positive inhibitor and its specific substrate mixture of P450 isoenzymes (CYP1A2, CYP2C9, CYP2C19, CYP2D6 and CYP3A4) was prepared; the human liver microsomes stored in the refrigerator below −60° C. were thawed on ice. When the human liver microsomes were completely dissolved, then diluted with potassium phosphate buffer (PB) to prepare a working solution with a certain concentration (0.253 mg/mL).

Firstly, 20.0 μL of substrate mixture was added to the reaction plate (20.0 μL of PB was added to the blank well), then 158 μL of human liver microsome working solution was added to the reaction plate, and the reaction plate was placed on ice for later use. At this time, 2.00 μL of test compound (N=1) and specific inhibitor (N=2) of each concentration were added to the corresponding well, and the group without inhibitor (test compound or positive inhibitor) was added with the corresponding organic solvent as a of control sample (control sample of test compound was dimethyl sulfoxide:methanol=1:1, positive control samples were all dimethyl sulfoxide:methanol=1:9). After pre-incubation in 37° C. water bath for 10 minutes, 20.0 μL of a coenzyme factor (NADPH) solution was added to the reaction plate and incubated in 37° C. water bath for 10 minutes. Then 400 μL of pre-cooled acetonitrile solution (internal standard containing 200 ng/mL tolbutamide and labetalol) was added to stop the reaction; the reaction plate was placed in a shaker and shaken for 10 min to mix evenly. Then the reaction plate was centrifuged at 4° C. and 4000 rpm for 20 min. 200 μL of supernatant was taken and added to 100 μL of water for sample dilution. Finally, the plate was sealed, shaken for 10 minutes to mix evenly for LC/MS/MS detection.

TABLE 2

Results of the inhibitory effect of the compound of the present disclosure on the activity of human liver microsomal cytochrome P450 isoenzymes

| | $IC_{50}$ (μM) | | | | |
|---|---|---|---|---|---|
| Compound | CYP1A2 | CYP2C9 | CYP2C19 | CYP2D6 | CYP3A4-M |
| 004 | 43.7 | 31.9 | 23.6 | >50 | 40.8 |
| 005A | >50 | 30.8 | >50 | >50 | >50 |
| 006 | 38.8 | 21.6 | >50 | >50 | 48.7 |

Conclusion: The compound of the present disclosure has a weak inhibitory effect on human liver microsomal cytochrome P450 isoenzymes and a low risk of "drug-drug interaction".

Experimental Embodiment 4: Cytochrome P450 Isoenzyme Time-Dependent Inhibitory Research Test 1. Test Purpose To test the time-dependent inhibitory effect of the test compounds on the activity of human liver microsomal cytochrome P450 isoenzyme CYP2C19.

2. Experimental Method

The experiment was divided into two groups. In the first group, human liver microsomes (HLM) were used as the incubation system, and a series of concentrations of test samples were added to the incubation system, and then coenzyme factor (NADPH) solution was added, and pre-incubated at 37° C. for 30 minutes. After pre-incubation, the probe substrate solution was added, and after incubation for a certain time, the reaction was terminated; the amount of probe substrate metabolites produced in the incubation solution was measured, and the enzyme activity was calculated. The second group of reactions was to use human liver microsomes (HLM) as the incubation system, and a series of concentrations of test samples were added to the incubation system, and then potassium phosphate buffer was added, and pre-incubated at 37° C. for 30 minutes. After pre-incubation, a mixed solution of NADPH and probe substrate was added. After incubation for a certain time, the reaction was terminated, the amount of probe substrate metabolites produced in the incubation solution was measured, and the enzyme activity was calculated.

Firstly, the test compound (10.0 mM) was diluted in gradient to prepare a working solution (100× final concentration), and the working solution concentrations were 5.00, 1.65, 0.500, 0.165, 0.0500, 0.0165 and 0.00500 mM respectively. At the same time, the positive inhibitor of P450 isoenzyme CYP2C19, probe substrate and NADPH working solution were prepared; the human liver microsomes stored in the refrigerator below −60° C. were thawed on ice. When the human liver microsomes were completely dissolved, then diluted with potassium phosphate buffer (PB) to prepare a working solution with a certain concentration (0.169 mg/mL).

Then 147.5 μL of human liver microsome working solution was added to the reaction plate, and the reaction plate was placed on ice for use. At this time, 2.50 μL of test compound (N=1) and the working solution of the positive control inhibitor (N=2) of each concentration were added to the corresponding well, and the corresponding organic solvent was added to the group without inhibitor (test compound or positive inhibitor). After incubating the reaction plate at 37° C. for 10 minutes, 50.0 μL of NADPH solution or potassium phosphate buffer solution was added to the first group or the second group of reaction wells respectively to start the reaction. The reaction plate was placed at 37° C. and pre-incubated for 30 minutes; 50 μL of substrate solution or a mixed solution of NADPH and substrate were added to the first group or the second group of reaction wells respectively to start the reaction. After 20 minutes, 250 μL of pre-cooled acetonitrile solution (internal standard containing 200 ng/mL tolbutamide and labetalol) was added to terminate the reaction. The reaction plate was placed on the shaker, shaken for 10 minutes to mix well; then centrifugated at 4° C. and 4000 rpm for 20 minutes. 200 μL of supernatant was taken and added to 200 μL of water for sample dilution; finally, the plate was sealed, shaken for 10 min to mix well for LC/MS/MS detection.

TABLE 3

Time-dependent inhibition of the compound of the present disclosure on human liver microsomal cytochrome P450 isoenzyme

| Compound | CYP | $IC_{50}$ (μM) −NADPH | $IC_{50}$ (μM) +NADPH | $IC_{50}$ offset multiple | Time-dependent inhibition (Yes or No) |
|---|---|---|---|---|---|
| 005A | CYP2C19 | 44.3 | >50 | <0.886 | No |

Conclusion: The compound of the present disclosure has no time-dependent inhibitory effect on human liver microsomal cytochrome P450 isoenzyme 2C19.

Experimental Embodiment 5: Cynomolgus Monkey In Vivo DMPK Study

1. Test Purpose

Male cynomolgus monkeys were used as test animals, and the plasma concentration of the compound was determined after a single oral administration and the pharmacokinetic behavior was evaluated.

2. Experimental Method

Two healthy male cynomolgus monkeys (fasting) were selected as the oral group. Oral vehicle was 20% hydroxypropyl-p-cyclodextrin aqueous solution. After the test compound was mixed with the vehicle, vortexed and sonicated to prepare 0.1 mg/mL approximately clear solution. The oral dosage of cynomolgus monkey was 0.5 mg/kg. After oral administration, whole blood was collected for a certain time to prepare plasma. The drug concentration was analyzed by LC-MS/MS method, and the pharmacokinetic parameters were calculated by Phoenix WinNonlin 6.3. See Table 4 for the results.

TABLE 4

PK test results of the compound of the present disclosure

| Compound | $C_{max}$ (nM) | Oral DNAUC (nM · h/mpk) | $T_{1/2}$ (h) |
|---|---|---|---|
| 004 | 132 | 1056 | 3.94 |

Note:

$C_{max}$ was the maximum concentration; DNAUC = $AUC_{PO}$/Dose, $AUC_{PO}$ was the oral exposure, Dose was the drug dose; $T_{1/2}$ was the half-life.

Conclusion: The compound of the present disclosure has a higher oral exposure in cynomolgus monkeys in vivo.

What is claimed is:

1. A compound represented by formula (I) or a pharmaceutically acceptable salt thereof, (I)

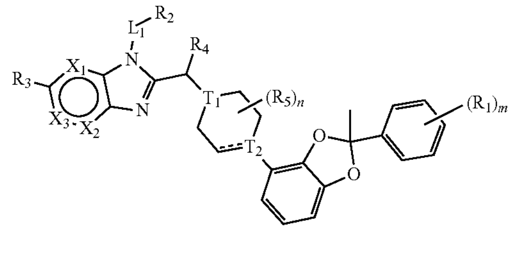

wherein, $\overline{=}$ is selected from a single bond and a double bond, and when $T_2$ is selected from N, $\overline{=}$ is a single bond;

$T_1$ and $T_2$ are selected from N and CH;

$X_1$ and $X_2$ are each independently selected from CH, N, O, and S;

$X_3$ is a single bond;

$L_1$ is selected from a single bond and —$C_{1-3}$ alkyl-;

$R_1$ is selected from F, Cl, Br, I, OH, $NH_2$, and CN;

m is selected from 0, 1, 2, 3, 4, and 5;

$R_2$ is selected from

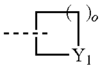 and 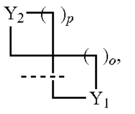, and the

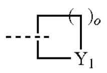 and 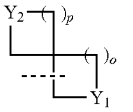

are optionally substituted by 1, 2, or 3 $R_a$;

$Y_1$ and $Y_2$ are each independently selected from CH, $CH_2$, N, NH, and O;

o and p are each independently selected from 0, 1, 2, and 3;

$R_3$ is selected from —C(=O)—NH—$R_b$, —C(=O)—$R_b$, —S(=O)$_2$—NH—$R_b$, and —S(=O)$_2$—$R_b$;

$R_5$ is selected from F, Cl, Br, I, and $C_{1-3}$ alkyl;

n is selected from 0, 1, and 2;

or the structura; moiety

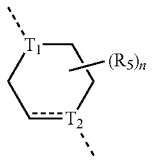

is

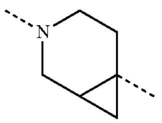 ;

$R_4$ is selected from H, F, Cl, Br, I. and $CH_3$;

$R_a$ is selected from F, Cl, Br, and I;

$R_b$ is selected from OH, CN, $C_{1-3}$ alkyl, and $C_{1-3}$ alkoxy, $C_{1-3}$ alkyl and $C_{1-3}$ alkyl and $C_{1-3}$ alkoxy are optionally substituted by 1, 2, or 3 R;

R is selected from F, Cl, and Br.

2. The compound or the pharmaceutically acceptable salt thereof according to claim 1, wherein the structural moiety

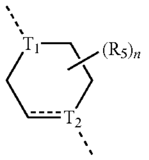

is selected from

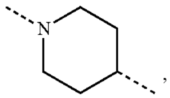, 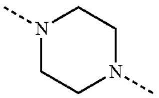, 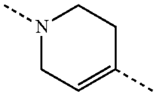 and 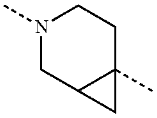.

3. The compound or the pharmaceutically acceptable salt thereof according to claim 1, wherein the structural moiety

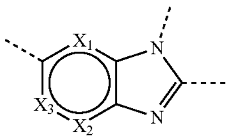

is N selected from

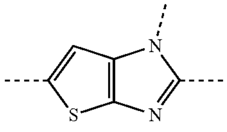, 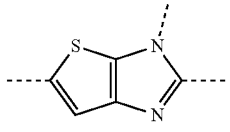, 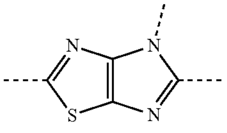 and 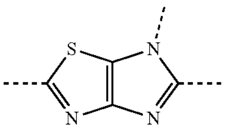.

4. The compound or the pharmaceutically acceptable salt thereof according to claim 1, which is selected from:

(I-3)

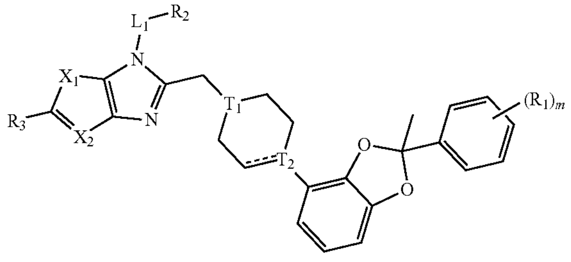

-continued (I-4)

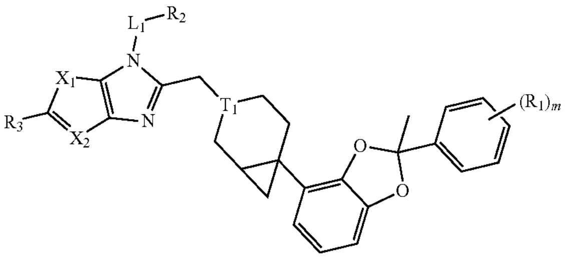

wherein,

⎓ is selected from a single bond and a double bond, and when $T_2$ is N, ⎓ is a single bond.

5. A method for activating GLP-1 receptor in a subject in need thereof, comprising: administering an effective amount of the compound or the pharmaceutically acceptable salt thereof according to claim 1 to the subject.

6. The compound or the pharmaceutically acceptable salt thereof according to claim 1, selected from

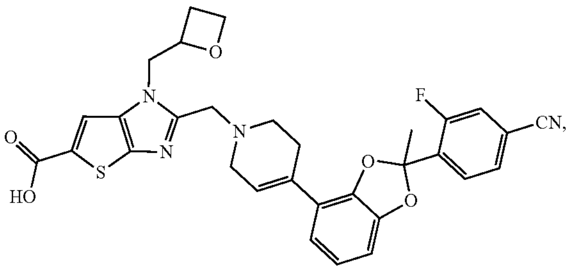

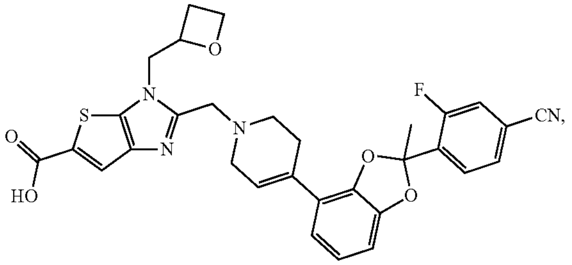

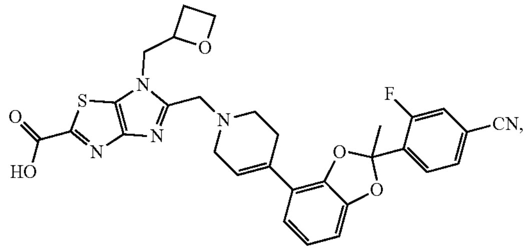

and

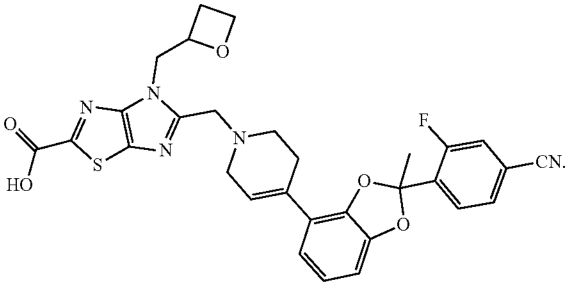

7. The compound or the pharmaceutically acceptable salt thereof according to claim 6, which is selected from:

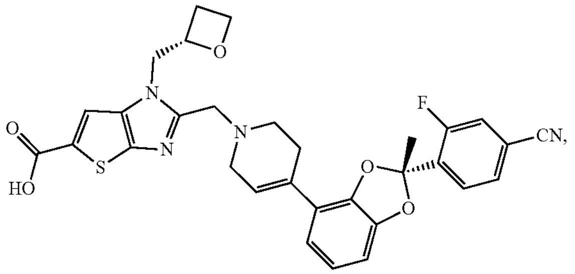

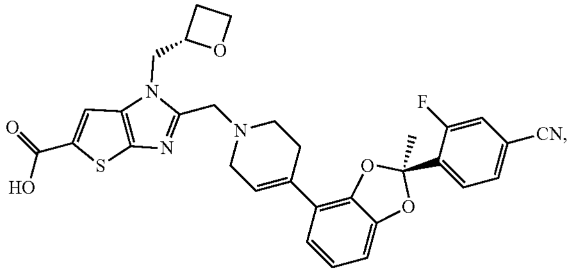

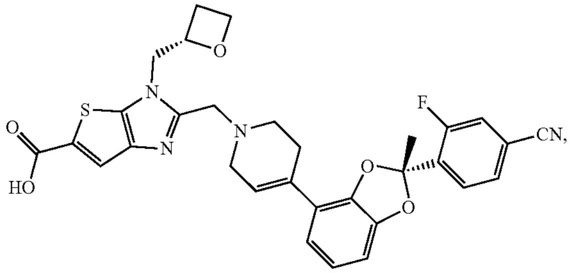

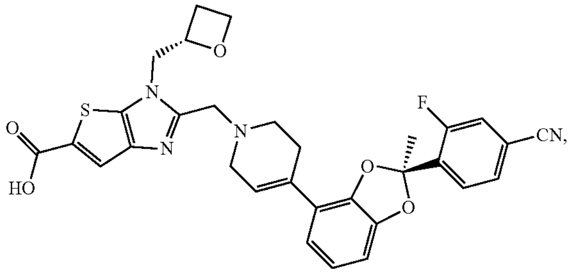

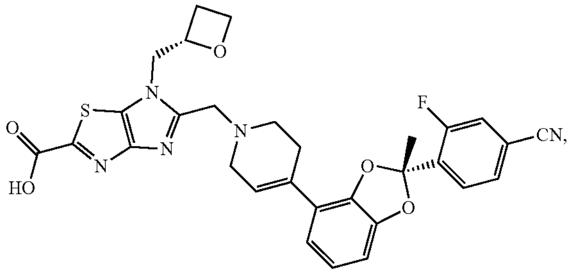

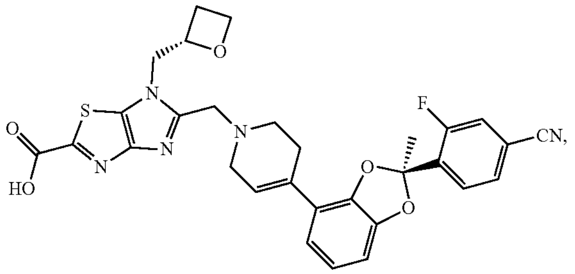

-continued
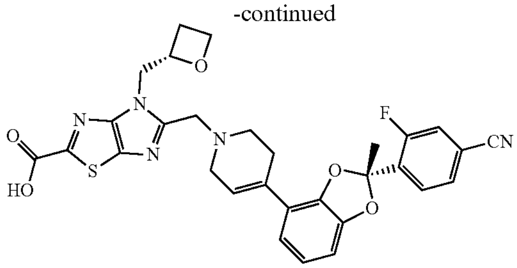
and
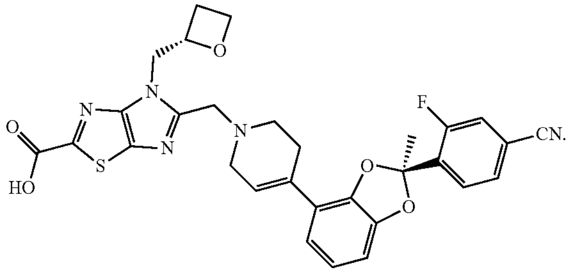
* * * * *